(12) United States Patent
Ge et al.

(10) Patent No.: US 7,759,493 B2
(45) Date of Patent: Jul. 20, 2010

(54) ANTIDIABETIC BICYCLIC COMPOUNDS

(75) Inventors: Min Ge, Edison, NJ (US); Lihu Yang, Edison, NJ (US); Changyou Zhou, Princeton, NJ (US); Songnian Lin, Monroe, NJ (US); Haifeng Tang, Metuchen, NJ (US); Eric Dean Cline, Princeton, NJ (US); Sunita Malkani, Lincoln Park, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 577 days.

(21) Appl. No.: 11/794,705

(22) PCT Filed: Jan. 30, 2006

(86) PCT No.: PCT/US2006/003255

§ 371 (c)(1),
(2), (4) Date: Jul. 3, 2007

(87) PCT Pub. No.: WO2006/083781

PCT Pub. Date: Aug. 10, 2006

(65) Prior Publication Data

US 2009/0312303 A1 Dec. 17, 2009

Related U.S. Application Data

(60) Provisional application No. 60/648,671, filed on Jan. 31, 2005, provisional application No. 60/697,038, filed on Jul. 6, 2005.

(51) Int. Cl.
| | |
|---|---|
| A61K 31/421 | (2006.01) |
| A61K 31/4245 | (2006.01) |
| A61K 31/426 | (2006.01) |
| A61K 31/4436 | (2006.01) |
| A61K 31/4725 | (2006.01) |
| A61K 31/443 | (2006.01) |
| A61K 31/4439 | (2006.01) |
| C07D 417/12 | (2006.01) |
| C07D 413/12 | (2006.01) |
| C07D 233/72 | (2006.01) |
| C07D 277/34 | (2006.01) |
| C07D 271/06 | (2006.01) |
| C07D 263/44 | (2006.01) |

(52) U.S. Cl. .................. 548/183; 548/226; 548/132; 548/317.1; 546/141; 546/269.7; 514/369; 514/309; 514/342; 514/364; 514/398; 514/376

(58) Field of Classification Search .......... 548/183, 548/226
See application file for complete search history.

(56) References Cited

FOREIGN PATENT DOCUMENTS

| EP | 1 148 054 B1 | 4/2001 |
|---|---|---|
| WO | WO 2004/033438 A1 | 4/2004 |

OTHER PUBLICATIONS

Briscoe, C.P. et al., "The Orphan G Protein-coupled Receptor GPR40 Is Activated by Medium and Long Chain Fatty Acids", The Journal of Biological Chemistry, vol. 278, No. 13, pp. 113903-11311, 2003.
Itoh, Y. et al., "Free fatty acids regulate insulin secretion from pancreatic beta cells through GPR40", Nature, vol. 422, pp. 173-176, 2003.
Kotarsky, K. et al., "A human cell surface receptor acitivated by free fatty acids and thiazolidinedione drugs", Biochemical and Biophysical Research Communications, vol. 301, pp. 406-410, 2003.

*Primary Examiner*—Laura L. Stockton
(74) *Attorney, Agent, or Firm*—Philippe L. Durette; John C. Todaro

(57) ABSTRACT

Bicyclic compounds containing a phenyl or pyridyl ring fused to a cycloalkyl or heterocyclic ring, to which is attached a 5-membered heterocyclic ring, including pharmaceutically acceptable salts and prodrugs thereof, are agonists of G-protein coupled receptor 40 (GPR40) and are useful as therapeutic compounds, particularly in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

20 Claims, No Drawings

ANTIDIABETIC BICYCLIC COMPOUNDS

CROSS REFERENCE TO RELATED APPLICATIONS

This application is the National Stage of International Application No. PCT/US2006/003255, filed 30 Jan. 2006, which claims the benefit under 35 U.S.C. 119(e) of U.S. Provisional Application No. 60/648,671, filed 31 Jan. 2005, and Application No. 60/697,038, filed 6 Jul. 2005.

FIELD OF THE INVENTION

The instant invention is concerned with bicyclic compounds containing a phenyl ring fused to a carbocyclic or heterocyclic ring, including pharmaceutically acceptable salts and prodrugs thereof, which are agonists of G-protein coupled receptor 40 (GPR40) and are useful as therapeutic compounds, particularly in the treatment of Type 2 diabetes mellitus, and of conditions that are often associated with this disease, including obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP m), National Institutes of Health, 2001, NIH Publication No. 01-3670. Patients with metabolic syndrome, whether or not they have or develop overt diabetes mellitus, have an increased risk of developing the macrovascular and microvascular complications that occur with type 2 diabetes, such as atherosclerosis and coronary heart disease.

There are several available treatments for type 2 diabetes, each of which has its own limitations and potential risks. Physical exercise and a reduction in dietary intake of calories often dramatically improve the diabetic condition and are the usual recommended first-line treatment of type 2 diabetes and of pre-diabetic conditions associated with insulin resistance. Compliance with this treatment is very poor because of well-entrenched sedentary lifestyles and excess food consumption, especially of foods containing high amounts of fat and carbohydrates. Pharmacologic treatments have focused on three areas of pathophysiology: (1) Hepatic glucose production (biguanides), (2) insulin resistance (PPAR agonists), and (3) insulin secretion.

The biguanides are a class of drugs that are widely used to treat type 2 diabetes. The two best known biguanides, phenformin and metformin, cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or an insulin secretagogues, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of type 2 diabetes, resulting in partial or complete correction of elevated plasma glucose levels without the occurrence of hypoglycemia. PPAR-gamma agonism is believed to be responsible for the improved insulin sensitization that is observed in human patients who are treated with the glitazones. New PPAR agonists are currently being developed. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) are promising because they reduce hyperglycemia and also improve lipid metabolism. The currently marketed PPAR gamma agonists are modestly effective in reducing plasma glucose and HemoglobinA1C. The currently marketed compounds do not greatly improve lipid metabolism and may actually have a negative effect on the lipid profile. Thus, the PPAR compounds represent an important advance in diabetic therapy, but further improvements are still needed.

Another widely used drug treatment involves the administration of insulin secretagogues, such as the sulfonylureas (e.g. tolbutamide and glipizide). These drugs increase the plasma level of insulin by stimulating the pancreatic β-cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules, whereas other extracellular signals act as potentiators or inhibitors of insulin secretion through GPCR's present on the plasma membrane. Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 (Itoh, Y. et al., Nature. 422: 173 [2003]; Briscoe, C. P. et al., J. Biol. Chem. 278: 11303 [2003]; Kotarsky, K. et al., Biochem. Biophys. Res. Comm. 301: 406 [2003]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat type 2 diabetic patients with daily insulin injections. By restoring or preserving islet function, GPR40 agonists may delay or prevent the diminution and loss of islet function in a type 2 diabetic patient.

SUMMARY OF THE INVENTION

The class of compounds described herein is a new class of GPR40 agonists. The compounds are useful in the treatment of diseases that are modulated by GPR40 agonists, including type 2 diabetes and hyperglycemia that may be associated with type 2 diabetes or pre-diabetic insulin resistance, and also obesity.

The present invention is directed to a compound of formula I, or a pharmaceutically acceptable salt thereof, including individual diastereomers and enantiomers thereof, and mixtures of diastereomers and/or enantiomers thereof:

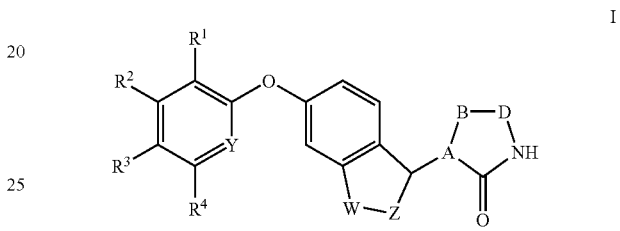

I wherein A is independently selected from the group consisting of —CH— and —N—;

B is selected from the group consisting of —S—, —O—, —NH—, —C(=O)—, and —CH$_2$—;

D is selected from the group consisting of —C(=O)—, —C(=S)—, —C(=NH)—, —O—, and —NH—;

W and Z are independently selected from —CH$_2$—, —CF$_2$—, —CH$_2$CH$_2$—, and —CH$_2$CH$_2$CH$_2$—, and one of W and Z optionally may be selected from —O—, —C(=O)—, —NR$_6$—, —S—, —SO—, and —SO$_2$—;

Y is selected from =CH— and =N—;

Heterocyle is a 5-6 membered saturated or partly saturated monocyclic heterocyclic ring having 1-3 heteroatoms independently selected from O, N and S;

Heteroaryl is a 5-6 membered monocyclic heteroaromatic ring having 1-3 heteroatoms independently selected from O, N and S;

R$^1$, R$^2$, R$^3$ and R$^4$ are each independently selected from the group consisting of H, halogen, —CN, —NO$_2$, —C$_1$-C$_6$alkyl, —OC$_1$-C$_6$alkyl, —SC$_1$-C$_6$alkyl, —S(O)$_2$C$_1$-C$_6$alkyl, —N(R$^6$)(R$^6$), N(R$^6$)C(=O)C$_1$-C$_6$alkyl, —N(R$^6$)S(O)$_2$C$_1$-C$_6$alkyl, —C(=O)H, —C(=O)OH, —C(=O)OC$_1$-C$_6$alkyl, —C(=O)C$_1$-C$_6$alkyl, —C(=O)N(R$^6$)(R$^6$), —C(=O)phenyl, —C(=O)naphthyl, —C(=O)Heterocyle, Heterocycle, Heteroaryl, C$_3$-C$_7$-cycloalkyl, phenyl and naphthyl;

wherein —C$_1$-C$_6$alkyl and the alkyl groups of —OC$_1$-C$_6$alkyl, —SC$_1$-C$_6$alkyl, —S(O)$_2$C$_1$-C$_6$alkyl, —N(R$^6$)C(=O)C$_1$-C$_6$alkyl, —N(R$^6$)S(O)$_2$C$_1$-C$_6$alkyl, —C(=O)C$_1$-C$_6$alkyl, and —C(=O)OC$_1$-C$_6$alkyl are optionally substituted with 1-5 halogens and are optionally also substituted with 1-2 groups independently selected from —OH, —OC$_1$-C$_3$alkyl which is optionally substituted with 1-5 halogens, —CF$_3$, —S(O)$_2$C$_1$-C$_3$alkyl, —C(=O)C$_1$-C$_3$alkyl, C(=O)C$_1$-C$_6$alkyl, —NHC(=O)CH$_3$, —NHC(=O)OC$_1$-C$_6$alkyl, —NHS(O)$_2$CH$_3$, —N(R$^6$)(R$^6$), Heterocycle, Heteroaryl, C$_3$-C$_7$-cycloalkyl, phenyl, and naphthyl;

wherein —C(=O)phenyl, —C(=O)naphthyl, —C(=O)Heterocyle, Heterocycle, Heteroaryl, C$_3$-C$_7$-cycloalkyl, phenyl and naphthyl either as $R^1$, $R^2$, $R^3$, $R^4$, or as substituents on $R^1$, $R^2$, $R^3$ and $R^4$ are optionally substituted with 14 substituents independently selected from halogen, —$CF_3$, —$OCF_3$, —CN, —$NO_2$, —OH, —$C_1$-$C_3$alkyl, —C(=O)$C_1$-$C_3$alkyl, —S(O)$_2C_1$-$C_3$alkyl, and —O$C_1$-$C_3$alkyl, wherein said —$C_1$-$C_3$alkyl, —O$C_1$-$C_3$alkyl, —S(O)$_2C_1$-$C_3$alkyl, and —C(=O)$C_1$-$C_3$alkyl substituents are optionally substituted with 1-3 halogens; and wherein alternatively one pair of ortho substituents selected from ($R^1$-$R^2$), ($R^2$-$R^1$), ($R^2$-$R^3$), ($R^3$-$R^2$), ($R^3$-$R^4$), and ($R^4$-$R^3$) may be connected to form a divalent bridging group having a length of 3-5 atoms, wherein said divalent bridging group is selected from —$CH_2CH_2CH_2$—, —$CH_2CH_2CH_2CH_2$—, —$CH_2CH_2CH_2CH_2CH_2$—, —$OCH_2CH_2$—, —$OCH_2CH_2CH_2$—, —$OCH_2CH_2CH_2CH_2$—, —$CH_2OCH_2$—, —$CH_2OCH_2CH_2$—, —$CH_2OCH_2CH_2CH_2$—, —$CH_2CH_2OCH_2CH_2$—, and —$SCH_2CH_2$—, wherein said bridging group is optionally substituted with 1-3 substituent groups independently selected from halogen, —OH, —CN, —$NO_2$, —$C_1$-$C_3$alkyl, —O$C_1$-$C_3$alkyl, —S$C_1$-$C_3$alkyl, —S(O)$_2C_1$-$C_3$alkyl, —$CF_3$, and —$OCF_3$; and wherein alternatively the pair of ortho substituents $R^1$-$R^2$ may be connected by the 4-carbon chain —CH=CH—CH=CH— to form a fused phenyl ring at the $R^1$ and $R^2$ positions, or by the 4-atom chain —CH=CH—CH=N—, —N=CH—CH=CH—, —CH=N—CH=CH—, —CH=CH—N=CH—, —$CH_2CH_2CH_2$C(=O), or —C(=O)$CH_2CH_2CH_2$—, to form a fused pyridinyl ring, or a fused cyclohexanone ring at the $R^1$ and $R^2$ positions, wherein said fused phenyl ring, said fused pyridinyl ring, and said fused cyclohexanone ring is optionally substituted with 1-3 substituents independently selected from halogen, —OH, —CN, —$NO_2$, —$C_1$-$C_3$alkyl, —O$C_1$-$C_3$alkyl, —S$C_1$-$C_3$alkyl, —S(O)$_2C_1$-$C_3$alkyl, —$CF_3$, and —$OCF_3$; and wherein alternatively the pair of ortho substituents $R^1$-$R^2$ may be connected by the 3-atom chain —CH=CHO—, —OCH=CH—, —CH=CH—S—, —SCH=CH—, —CH=CHN($R^6$)—, —N($R^6$)CH=CH—, —$CH_2CH_2$C(=O)—, and —C(=O)$CH_2CH_2$—, to form a five-membered ring fused to the phenyl ring at the $R^1$ and $R^2$ positions, wherein said fused five-membered ring is optionally substituted with 1-3 substituents independently selected from halogen, —OH, —CN, —$NO_2$, —$C_1$-$C_3$alkyl, —O$C_1$-$C_3$alkyl, —S$C_1$-$C_3$alkyl, —S(O)$_2C_1$-$C_3$alkyl, —$CF_3$, and —$OCF_3$; and $R^6$ is selected from the group consisting of H and —$C_1$-$C_6$alkyl.

In the above definitions and subsequent definitions, alkyl groups may be either linear or branched, unless otherwise specified.

In a closely related embodiment, $R^1$, $R^2$, $R^3$ and $R^4$ are as defined above, except that when $R^1$, $R^2$, $R^3$ or $R^4$ is $C_1$-$C_6$alkyl, —O$C_1$-$C_6$alkyl, —S$C_1$-$C_6$alkyl, —S(O)$_2C_1$-$C_6$alkyl, —N($R^6$)C(=O)$C_1$-$C_6$alkyl, —N($R^6$)S(O)$_2C_1$-$C_6$alkyl, —C(=O)O$C_1$-$C_6$alkyl, or —C(=O)$C_1$-$C_6$alkyl, then the $C_1$-$C_6$alkyl group is optionally substituted with 1-5 halogens and is optionally also substituted with 1-2 groups independently selected from —OH, —O$C_1$-$C_3$alkyl, —$CF_3$, —$OCF_3$, —S(O)$_2C_1$-$C_3$alkyl, —C(=O)$C_1$-$C_3$alkyl, —NHC(=O)$CH_3$, —NHS(O)$_2CH_3$, Heterocycle, Heteroaryl, $C_3$-$C_7$-cycloalkyl, phenyl, and naphthyl, where the substituents on Heterocycle, Heteroaryl, $C_3$-$C_7$-cycloalkyl, phenyl, and naphthyl are as defined above; and all other substituents and groups are as defined above.

In another closely related embodiment, $R^1$, $R^2$, $R^3$ and $R^4$ are each independently selected from the group consisting of H, halogen, —CN, —$NO_2$, —$C_1$-$C_6$alkyl, —O$C_1$-$C_6$alkyl, —SC 1-$C_6$alkyl, —S(O)$_2C_1$-$C_6$alkyl, —N($R^6$)($R^6$), —N($R^6$)C(=O)$C_1$-$C_6$alkyl, —N($R^6$)S(O)$_2C_1$-$C_6$alkyl, —C(=O)$C_1$-$C_6$alkyl, —C(=O)N($R^6$)($R^6$), —C(=O)phenyl, —C(=O)naphthyl, —C(=O)Heterocyle, Heterocycle, Heteroaryl, $C_3$-$C_7$-cycloalkyl, phenyl and naphthyl;

wherein —$C_1$-$C_6$alkyl and the alkyl groups of —O$C_1$-$C_6$alkyl, —S$C_1$-$C_6$alkyl, —S(O)$_2C_1$-$C_6$alkyl, —N($R^6$)C(=O)$C_1$-$C_6$allyl, —N($R^6$)S(O)$_2C_1$-$C_6$alkyl, and —C(=O)$C_1$-$C_6$alkyl are optionally substituted with 1-5 halogens and are optionally also substituted with 1-2 groups independently selected from —OH, —O$C_1$-$C_3$alkyl, —$CF_3$, —$OCF_3$, —S(O)$_2C_1$-$C_3$alkyl, —C(=O)$C_1$-$C_3$alkyl, —NHCOCH$_3$, —NHS(O)$_2CH_3$, Heterocycle, Heteroaryl, $C_3$-$C_7$-cycloalkyl, phenyl, and naphthyl;

wherein —C(=O)phenyl, —C(=O)naphthyl, —C(=O)Heterocyle, Heterocycle, Heteroaryl, $C_3$-$C_7$-cycloalkyl, phenyl and naphthyl either as $R^1$, $R^2$, $R^3$, $R^4$, or as substituents on $R^1$, $R^2$, $R^3$ and $R^4$ are optionally substituted with 1-4 substituents independently selected from halogen, —$CF_3$, —$OCF_3$, —CN, —$NO_2$, —OH, —$C_1$-$C_3$alkyl, —C(=O)$C_1$-$C_3$alkyl, —S(O)$_2C_1$-$C_3$alkyl, and —O$C_1$-$C_3$alkyl, wherein said —$C_1$-$C_3$alkyl, —O$C_1$-$C_3$alkyl, —S(O)$_2C_1$-$C_3$alkyl, and —C(=O)$C_1$-$C_3$alkyl substituents are optionally substituted with 1-3 halogens.

All other substituents in the above embodiment are the same as previously described, including alternative definitions of $R^1$, $R^2$, $R^3$ and $R^4$ in which $R^1$, $R^2$, $R^3$ and $R^4$ groups that are ortho to one another may be connected by bridging groups to create additional fused rings.

In the above description, the bridging groups as drawn that connect pairs of groups $R^1$, $R^2$, $R^3$ and $R^4$ that are ortho to one another may be attached to the ring either left-to-right or right-to-left.

DETAILED DESCRIPTION OF THE INVENTION

The invention has numerous embodiments, which are summarized below. The invention includes the compounds as shown, and also includes individual diastereomers, enantiomers, and epimers of the compounds, and mixtures of diastereomers and/or enantiomers thereof. The invention also includes pharmaceutically acceptable salts of the compounds, and pharmaceutical compositions comprising the compounds and a pharmaceutically acceptable carrier. The compounds may be especially useful in treating insulin resistance, type 2 diabetes, and dyslipidemia that is associated with type 2 diabetes and insulin resistance.

A subgroup of the compounds of Formula I comprises compounds, including pharmaceutically acceptable salts thereof, in which $R^1$, $R^2$, $R^3$, and $R^4$ are independently selected from (1) H; (2) Halogen; (3) —$NO_2$; (4) —CN; (5) —$C_{1-6}$alkyl, which is optionally substituted with 1-5 halogens and is optionally also substituted with 1-2 substituents which are independently selected from —OH, —$CF_3$, —C(=O)$C_1$-$C_3$alkyl, and —O$C_{1-3}$alkyl which is optionally substituted with 1-3 halogens; (6) —O$C_{1-6}$alkyl, which is optionally substituted with 1-5 halogens and is optionally also substituted with 1-2 groups independently selected from —$CF_3$ and —C(=O)$C_1$-$C_3$alkyl; (7) —C(=O)$C_1$-$C_3$alkyl, which is optionally substituted with 1-5 halogens and is optionally also substituted with 1-2 groups independently selected from —$CF_3$; and (8) $C_3$-$C_7$cycloalkyl, phenyl, or Heterocycle, each of which is optionally substituted with 1-3 substituents independently selected from halogen, —OH, —O$C_{1-3}$alkyl, $CF_3$, and —C(=O)$C_1$-$C_3$alkyl.

In subgroups of the compounds having Formula I, or pharmaceutically acceptable salts thereof, $R^1$, $R^2$, $R^3$, and $R^4$ are each independently selected from H, F, Br, Cl, $CH_3$, $CF_3$, —$CH_2OH$, —$CH(OH)CH_3$, —$C(=O)H$, —$C(=O)OH$, —$C(=O)CH_3$, —$CH_2CH_3$, —$CH_2CF_3$, cyclopropyl, —CN, —$OCH_3$, —$OCF_3$, —$NO_2$, —$CH(CH_3)_2$, n-$C_3H_7$, n-$C_5H_{11}$, —$C_2F_5$, —$CHFCH_3$, —$CHFCF_3$, —$CF_2CH_3$, —$CHF_2$, —$CH_2F$, —$OCHF_2$, —$OCH_2F$, —$OCH_2$-phenyl, —$C(=O)$ $OCH_3$, —$S(O)_2CH_3$, —$C(=O)NH_2$, —$CH_2OC(=O)CH_3$, —$NH_2$, —$CH_2NH_2$, —$CH_2N(CH_3)_2$, —$CH_2NHC(=O)OC(CH_3)_3$, —$CH_2$(1-pyrrolidinyl), and —$C(=O)$(3,3-difluoro-1-azetidinyl).

In subgroups of the compounds having Formula I, or pharmaceutically acceptable salts thereof, $R^1$, $R^2$, $R^3$, and $R^4$ are each independently selected from H, F, Br, Cl, $CH_3$, $CF_3$, —$CH(OH)CH_3$, —$C(=O)CH_3$, —$CH_2CH_3$, —$CH_2CF_3$, cyclopropyl, —CN, —$OCH_3$, —$OCF_3$, and —$NO_2$.

In other subgroups of the compounds having Formula I or pharmaceutically acceptable salts thereof, $R^1$, $R^2$, $R^3$, and $R^4$ are each independently selected from H, F, Br, Cl, $CH_3$, $CF_3$, —$CH_2OH$, —$CH(OH)CH_3$, —$C(=O)H$, —$C(=O)OH$, —$C(=O)CH_3$, —$CH_2CH_3$, —$CH_2CF_3$, cyclopropyl, —CN, —$OCH_3$, —$OCF_3$, and —$NO_2$.

A subgroup of compounds of Formula I includes compounds in which $R^1$ and $R^2$ are connected by the 4-carbon chain —CH=CH—CH=CH— to form a fused phenyl group at the $R^1$ and $R^2$ positions, where the fused phenyl group is optionally substituted with 1-3 substituents independently selected from halogen, —OH, —CN, —$NO_2$, —$C_1$-$C_3$alkyl, —$OC_1$-$C_3$alkyl, —$SC_1$-$C_3$alkyl, —$S(O)_2C_1$-$C_3$alkyl, —$CF_3$, and —$OCF_3$, and pharmaceutically acceptable salts thereof.

A subgroup of compounds of Formula I includes compounds in which $R^1$ and $R^2$ are connected by a 3- or 4-carbon chain selected from the group consisting of —CH=CH—CH=CH—, —$CH_2CH_2CH_2$—, —$CH_2CH_2C(=O)$—, and —$C(=O)CH_2CH_2$— to form a fused phenyl, cyclopentyl or cyclopentanone ring at the $R^1$ and $R^2$ positions, wherein the fused phenyl, cyclopentyl and cyclopentanone rings are optionally substituted with 1-3 substituents independently selected from halogen, —OH, —CN, —$NO_2$, —$C_1$-$C_3$alkyl, —$OC_1$-$C_3$alkyl, —$SC_1$-$C_3$alkyl, —$S(O)_2C_1$-$C_3$alkyl, —$CF_3$, and —$OCF_3$;

In another embodiment, the compound of Formula I, or a pharmaceutically acceptable salt thereof, has a Z group which is —$CH_2$— and a group W which is $CH_2$—, —$CF_2$—, —$CH_2CH_2$—, —O—, or —S—.

In another embodiment, the compound of Formula I, or a pharmaceutically acceptable salt thereof, has a group A which is —CH— or —N—; a group B which is —S—, —O—, —NH—, or —$CH_2$—; and a group D which is $C(=O)$—.

Additional embodiments include compounds of Formula I, and pharmaceutically acceptable salts thereof, wherein $R^1$ and $R^2$ are connected by a divalent bridging group selected from —$CH_2CH_2CH_2$—, —$CH_2CH_2CH_2CH_2$—, —$CH_2CH_2O$—, —$OCH_2CH_2$—, —$CH_2CH_2S$—, and —$SCH_2CH_2$—, forming a 5- or 6-membered ring fused to the phenyl ring at the $R^1$ and $R^2$ positions of the phenyl ring.

In a preferred embodiment of the compounds having Formula I or pharmaceutically acceptable salts thereof, $R^1$, $R^2$, $R^3$, and $R^4$ are each independently selected from the group consisting of H, F, Br, Cl, $CH_3$, $CF_3$, —$CH_2OH$, —$CH(OH)CH_3$, —$C(=O)H$, —$C(=O)OH$, —$C(=O)CH_3$, —$CH_2CH_3$, —$CH_2CF_3$, cyclopropyl, —CN, —$OCH_3$, —$OCF_3$, and —$NO_2$, wherein $R^1$ and $R^2$ alternatively may be connected by the 4-carbon chain —CH=CH—CH=CH— to form a fused phenyl group at the $R^1$ and $R^2$ positions;

Y is selected from =CH— and =N—;

W is selected from the group consisting of —O—, —S—, and $CH_2$;

Z is selected from the group consisting of —$CH_2$— and —$CH_2CH_2$—;

A is —CH— or —N—;

B is selected from the group consisting of —S—, —O—, and —$CH_2$—; and

D is —$C(=O)$.

Additional embodiments of the invention include compounds having Formula Ia, and pharmaceutically acceptable salts thereof, in which

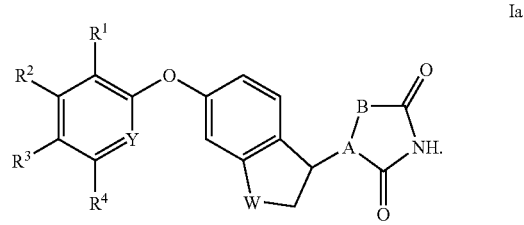

Ia $R^1$, $R^2$, $R^3$, and $R^4$ are each independently selected from H, F, Br, Cl, $CH_3$, $CF_3$, —$CH(OH)CH_3$, —$C(=O)CH_3$, —$CH_2CH_3$, —$CH_2CF_3$, cyclopropyl, —CN, —$OCH_3$, —$OCF_3$, and —$NO_2$;

or alternatively $R^1$ and $R^2$ are connected by the 4-carbon chain —CH=CH—CH=CH— to form a fused phenyl group at the $R^1$ and $R^2$ positions;

Y is selected from =CH— and =N—;

W is selected from the group consisting of —$CH_2$—, —$CF_2$—, —$CH_2CH_2$—, —O—, and —S—;

A is —CH— or —N—; and

B is selected from the group consisting of —S—, —O—, —NH—, and —$CH_2$—.

A preferred embodiment includes compounds of Formula Ia, and pharmaceutically acceptable salts thereof, in which $R^1$ is H, F, Br, Cl, $CH_3$, $CF_3$ or —$CH_2CH_3$;

$R^2$ is H, $CH_3$, $CF_3$, —$CH_2CH_3$, or —$OCF_3$;

or alternatively $R^1$ and $R^2$ are connected by the 4-carbon chain —CH=CH—CH=CH— to form a fused phenyl group at the $R^1$ and $R^2$ positions;

$R^3$ is H, Cl, $CH_3$, $CF_3$, —CN, or —$NO_2$;

$R^4$ is H or —$CH_3$;

Y is =CH— or =N—;

W is —$CH_2$—, —$CH_2CH_2$—, or —S—;

A is —CH— or —N—; and

B is —S—, —O—, or —$CH_2$—.

Other preferred embodiments have Formula Ib, including pharmaceutically acceptable salts thereof:

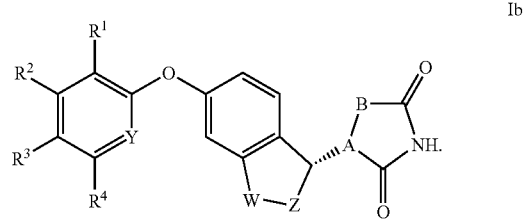

Ib

In these compounds, $R^1$, $R^2$, $R^3$, $R^4$, Y, W, Z, A, and B are as defined in earlier embodiments. Note that Formula Ib is a stereoisomer. Compounds having the stereochemistry of Formula Ib are generally more active than the epimers of the compounds. In the case where A=CH, a mixture of diastereomers results. The less active epimers have some therapeutic activity, and the less active epimers and other stereoisomers have utility as research tools to study the steric requirements of the receptor and mechanism of action of the receptor.

The compound of Formula Ib, or a pharmaceutically acceptable salt thereof, has the following definitions in more preferred embodiments:

$R^1$, $R^2$, $R^3$, and $R^4$ are each independently selected from H, F, Br, Cl, $CH_3$, $CF_3$, —CH(OH)CH$_3$, —C(=O)CH$_3$, —CH$_2$CH$_3$, —CH$_2$CF$_3$, cyclopropyl, —CN, —OCH$_3$, —OCF$_3$, and —NO$_2$;

Y is selected from =CH— and =N—;

W is selected from the group consisting of —CH$_2$—, —CF$_2$—, —CH$_2$CH$_2$—, —O—, and —S—;

Z is —CH$_2$—;

A is —CH— or —N—; and

B is selected from the group consisting of —S—, —O—, —NH—, and —CH$_2$—.

Other preferred subgroups comprise compounds having Formula Ic, or pharmaceutically acceptable salts thereof, wherein

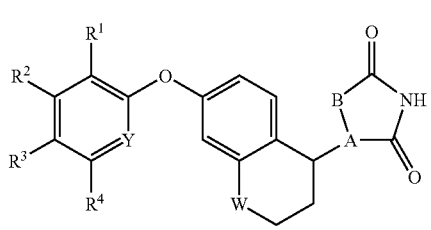

$R^1$, $R^2$, $R^3$, and $R^4$ are each independently selected from the group consisting of H, F, Br, Cl, $CH_3$, $CF_3$, —CH$_2$OH, —CH(OH)CH$_3$, —C(=O)H, —C(=O)OH, —C(=O)CH$_3$, —CH$_2$CH$_3$, —CH$_2$CF$_3$, cyclopropyl, —CN, —OCH$_3$, —OCF$_3$, and —NO$_2$; wherein $R^1$ and $R^2$ alternatively may be connected by the 4-carbon chain —CH=CH—CH=CH— to form a fused phenyl group at the $R^1$ and $R^2$ positions, wherein said fused phenyl group is optionally substituted with 1-3 substituents independently selected from halogen, —OH, CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$;

Y is selected from =CH— and =N—;

W is selected from the group consisting of —O— and —S—;

A is —CH— or —N—; and

B is selected from the group consisting of —S—, —O—, —NH—, and —CH$_2$—.

Other preferred subgroups of compounds have Formula Id, including pharmaceutically acceptable salts thereof, wherein

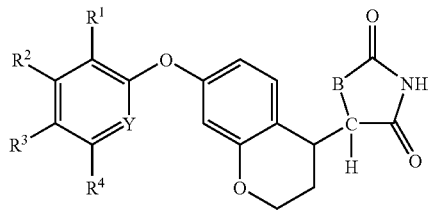

$R^1$, $R^2$, $R^3$, and $R^4$ are each independently selected from the group consisting of H, F, Br, Cl, $CH_3$, $CF_3$, —CH$_2$OH, —CH(OH)CH$_3$, —C(=O)H, —C(=O)OH, —C(=O)CH$_3$, —CH$_2$CH$_3$, —CH$_2$CF$_3$, cyclopropyl, —CN, —OCH$_3$, —OCF$_3$, and —NO$_2$, wherein $R^1$ and $R^2$ alternatively may be connected by the 4-carbon chain —CH=CH—CH=CH— to form a fused phenyl group at the $R^1$ and $R^2$ positions; and B is selected from the group consisting of —S— and —O—.

Other preferred groups of compounds, including pharmaceutically acceptable salts thereof, have the following structures, using any of the previously defined values for the substituent groups. These all have the same stereochemistry as was described above for the middle ring of Formula Ib:

(1)

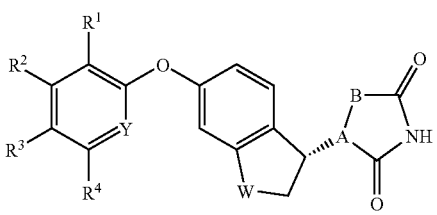

where $R^1$, $R^2$, $R^3$, $R^4$, A, B, Y, and W each are as defined previously, each being defined independently of the other groups, including pharmaceutically acceptable salts thereof.

(2)

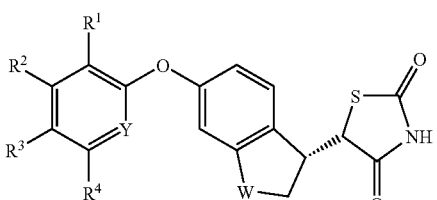

wherein $R^1$, $R^2$, $R^3$, $R^4$, and W each are as defined previously, each being defined independently of the other groups, including pharmaceutically acceptable salts thereof.

(3)

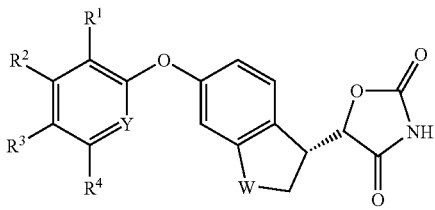

wherein $R^1$, $R^2$, $R^3$, $R^4$, and W each are as defined previously, each being defined independently of the other groups, including pharmaceutically acceptable salts thereof.

(4)

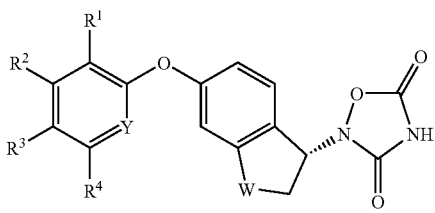

wherein $R^1$, $R^2$, $R^3$, $R^4$, Y, and W each are as defined previously, each being defined independently of the other groups, including pharmaceutically acceptable salts thereof.

(5)

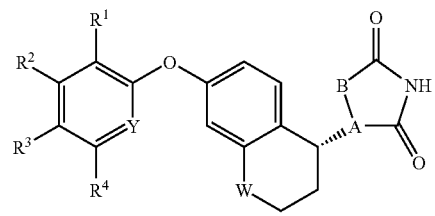

where $R^1$, $R^2$, $R^3$, $R^4$, A, B, Y, and W each are as defined previously, each being defined independently of the other groups, including pharmaceutically acceptable salts thereof. In preferred embodiments of Figure Ie and Ij, A is —CH—; and B is —S— or —O—.

In embodiments in which pairs of adjacent $R^1$, $R^2$, $R^3$, and $R^4$ groups are optionally connected by a bridging group to make a fused 5- or 6-membered ring, the bridging group is optionally substituted with 1-3 substituents independently selected from halogen, —OH, —CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$.

Although the specific stereochemistries described above are preferred, all other stereoisomers, including diastereomers, enantiomers, epimers, and mixtures of these may also have utility in treating GPR40 mediated diseases. Inactive or less active diastereoisomers and enantiomers are useful for scientific studies relating to the receptor and the mechanism of activation.

Structures of specific compounds and synthetic methods for making the compounds are disclosed in the Examples. Some of the Examples are disclosed in tables in the specification, along with analytical information. Information on how the Examples that are in the tables were made is in the specification. Where a stereochemical center is not defined (as for example A in figure I, where A is —CH—), the compound is a mixture of stereoisomers at that center. For such compounds, the individual stereoisomers, including enantiomers, diastereomers, and mixtures of these are also compounds of the invention. The compounds of the invention also include pharmaceutically acceptable salts.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of Formula I or a pharmaceutically acceptable salt thereof is the only active ingredient.

A compound of Formula I, or a pharmaceutically acceptable salt thereof, may be used in the manufacture of a medicament for the treatment of type 2 diabetes mellitus in a human or other mammalian patient.

A method of treating type 2 diabetes comprises the administration of a therapeutically effective amount of a compound of Formula I, or a pharmaceutically acceptable salt thereof, or a pharmaceutical composition comprising the compound, to a patient in need of treatment. Other medical uses of the compounds of Formula I are described hereinafter.

Definitions

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. Cycloalkenyl rings comprise a double bond in the ring.

"Aryl" is commonly used to refer to carbocyclic aromatic structures. The most common aryl groups are phenyl and naphthyl. Phenyl is generally the most preferred aryl group.

"Heterocycle" means a fully or partially saturated ring or ring system containing at least one heteroatom selected from N, S and O, wherein the number of heteroatoms and the ring size are defined herein. Examples of heterocycles include tetrahydrofuran, piperazine, piperidine, and morpholine.

"Heteroaryl" means an aromatic ring or two fused aromatic rings containing at least one ring heteroatom selected from N, O and S (including SO and $SO_2$), as defined more specifically herein. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, quinazolinyl, dibenzofuranyl, and the like.

"Halogen" includes fluorine, chlorine, bromine and iodine.

"Me" represents methyl.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, individual diastereomers, and mixtures of diastereomers and/or enantiomers. The present invention is meant to comprehend all such isomeric forms of the compounds of Formula I. Specifically, the compounds of the instant invention have at least one asymmetric center, which is on the ring that is fused to the phenyl ring at the point where the heterocyclic ring is attached. There may also a second asymmetric center in the heterocyclic ring. Additional asymmetric centers may be present depending upon the nature of the various substituents on the molecule. Each such asymmetric center will independently produce two optical isomers, and it is intended that all of the possible optical isomers, stereoisomers, and diastereomers in mixtures and as pure or partially purified compounds are included within the scope of this invention (i.e. all possible combinations of the asymmetric centers as pure compounds or in mixtures).

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, or when it has a basic substituent group in its structure, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are compounds of this invention. The claimed chemical structures of this application in some cases may themselves be prodrugs.

Utilities

Compounds of the present invention are potent agonists of the GPR40 receptor. The compounds of the invention, and pharmaceutically acceptable salts thereof, may be efficacious in the treatment of diseases that are modulated by GPR40 ligands and agonists. Many of these diseases are summarized below.

One or more of the following diseases may be treated by the administration of a therapeutically effective amount of a compound of this invention, or a pharmaceutically acceptable salt thereof, to a patient in need of treatment. Also, the compounds of the invention may be used for the manufacture of a medicament for treating one or more of these diseases:

(1) non-insulin dependent diabetes mellitus (type 2 diabetes);
(2) hyperglycemia;
(3) the metabolic syndrome;
(4) obesity;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) hyperapoBliproteinemia; and
(11) atherosclerosis.

Preferred uses of the compounds are for the treatment of one or more of the following diseases by administering a therapeutically effective amount to a patient in need of treatment. The compounds may be used for manufacturing a medicament for the treatment of one or more of these diseases:

(1) Type 2 diabetes, and specifically hyperglycemia;
(2) Metabolic syndrome;
(3) Obesity; and
(4) Hypercholesterolemia.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, and medicaments as described herein may also be effective in reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds may also be effective in delaying or preventing vascular restenosis and diabetic retinopathy.

The compounds of this invention may also have utility in improving or restoring β-cell function, so that they may be useful in treating type 1 diabetes or in delaying or preventing a patient with type 2 diabetes from needing insulin therapy.

The compounds generally may be efficacious in treating one or more of the following diseases: (1) type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure, and (19) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 25 mg, 50 mg, 100 mg, 200 mg, 300 mg, 400 mg, and 500 mg. Other oral forms may also have the same or similar dosages.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

In some instances, depending on the solubility of the compound or salt being administered, it may be advantageous to formulate the compound or salt as a solution in an oil such as a triglyceride of one or more medium chain fatty acids, a lipophilic solvent such as triacetin, a hydrophilic solvent (e.g. propylene glycol), or a mixture of two or more of these, also optionally including one or more ionic or nonionic surfactants, such as sodium lauryl sulfate, polysorbate 80, polyethoxylated triglycerides, and mono and/or diglycerides of one or more medium chain fatty acids. Solutions containing surfactants (especially 2 or more surfactants) will form emulsions or microemulsions on contact with water. The compound may also be formulated in a water soluble polymer in which it has been dispersed as an amorphous phase by such methods as hot melt extrusion and spray drying, such polymers including HPMCAS, HPMCS, and polyvinylpyrrolidinones.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. In the treatment of patients who have type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, such as sitagliptin, saxagliptin, and vildagliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, such as torcetrapib, and (viii) phenolic anti-oxidants, such as probucol;

(i) PPARα/γ dual agonists, such as muraglitazar, tesaglitazar, farglitazar, and JT-501;

(j) PPARα agonists such as those disclosed in WO97/28149;

(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $β_3$ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1, (p) GIP-1, (q) GLP-1 analogs, such as exendins, for example exenatide (Byetta), and (r) Hydroxysterol dehydrogenase-1 (HSD-1) inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Biological Assays

Generation of GPR40—Expressing Cells

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

FLIPR Assays

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 μl medium/well. The cells were incubated with 20 μl/well of the assay buffer (HBSS, 0.1% BSA, 20 mM HEPES, 2.5 mM probenecid, pH 7.4) containing 8 μM fluo-4, AM, 0.08% pluronic acid at room temperature for 100 minutes. Fluorescence output was measured using FLIPR. Compounds were dissolved in DMSO and diluted to desired concentrations with assay buffer. 13.3 μl/well of compound solution was added.

Inositol Phosphate Turnover Assay

The assay is performed in 96-well format. HEK cells stably expressing human GPR40 are plated to be 60-80% confluent within 72 hours. After 72 hours, the plates are aspirated and the cells washed with inositol-free DMEM (ICN). The wash media is replaced with 150 uL of 3H-inositol labeling media (inositol-free media containing 0.4% human albumin or 0.4% mouse albumin, 1×pen/strep antibiotics, glutamine, 25 mM HEPES to which is added 3H-myo-inositol NEN #NET114A 1 mCi/mL, 25 Ci/mmol diluted 1:150 in loading media with a final specific radioactivity of 1 uCi/150 uL). Alternatively, the human and mouse albumin can be added after the overnight labeling step before the addition of LiCl.

The assay is typically run the next day after 18 hours labeling. On the day of the assay, 5 uL of 300 mM LiCl is added to all wells and incubated at 37 degrees for 20 mins. 0.75 uL of 200× compounds are added and incubated with the cells for 60 minutes at 37 degrees. The media is then aspirated off and the assay terminated with the addition of 60 uL 10 mM formic acid. The cells are lysed for 60 mins at room temperature. 15-30 uL of lysate is mixed with 70 uL/1 mg YSi SPA beads (Amersham) in clear bottom Isoplates. The plates are shaken for 2 hours at room temperature. Beads are allowed to settle and the plates are counted in the Wallac Microbeta.

In Vivo Studies

Male C57BL/6N mice (7-12 weeks of age) are housed 10 per cage and given access to normal diet rodent chow and water ad libitum. Mice are randomly assigned to treatment groups and fasted 4 to 6 hours. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 minutes after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

EXAMPLES

The following Examples are provided to illustrate the invention and are not to be construed as limiting the invention in any manner. The scope of the invention is defined by the appended claims.

Several methods for preparing the compounds of this invention are illustrated in the following Schemes and Examples. Starting materials are either commercially available or made by known procedures in the literature or as illustrated. The present invention further provides processes for the preparation of compounds of formula I as defined above.

One general way of constructing target compounds I starting from an Intermediate of the formula (1-3) is by coupling of the phenol (1-1) and halogen substituted ketone (1-2) or haloarene (1-4) and hydroxyketone (1-5) in the presence of a base (Scheme 1).

SCHEME 1

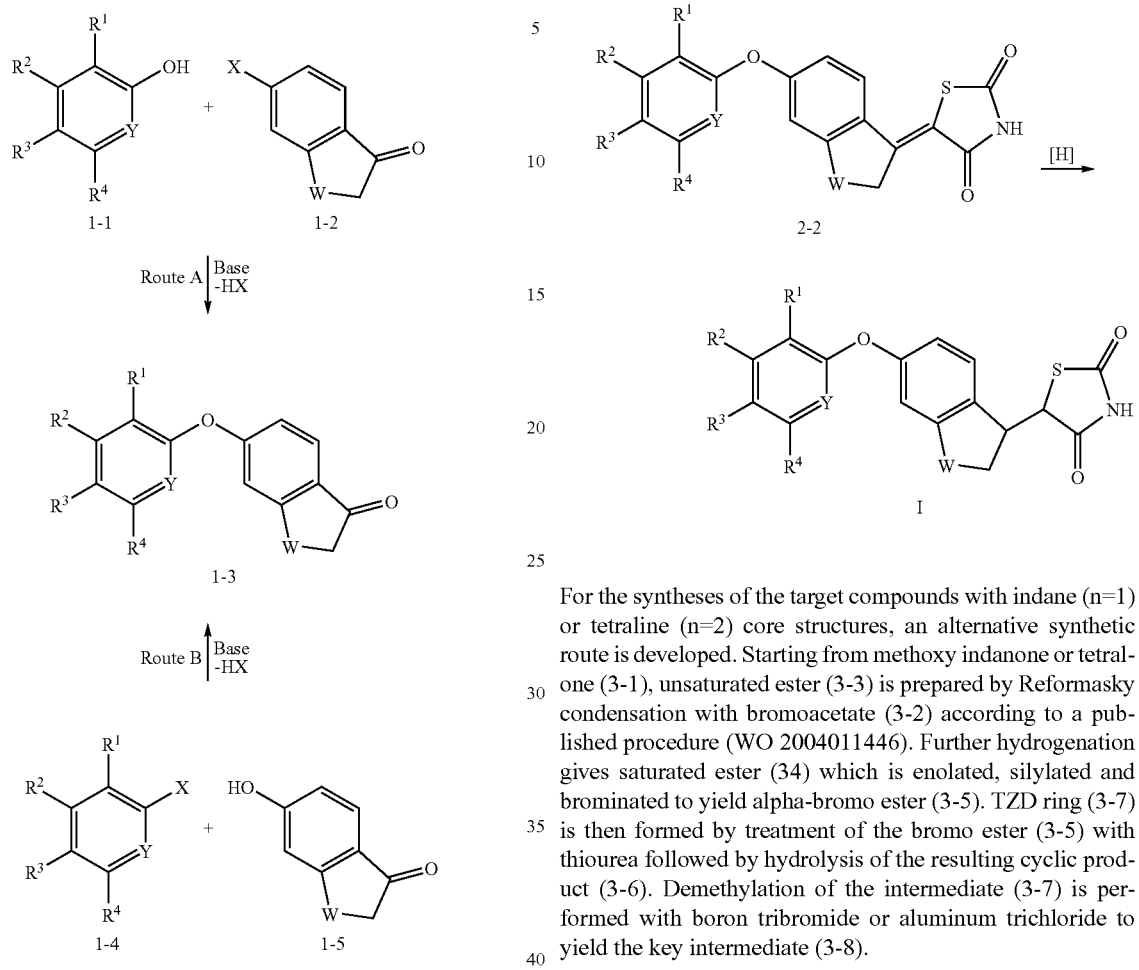

The ketone of Formula (1-3), prepared according to Scheme 1, undergoes condensation with 2,4-thiazolidinedione (2-1) in the presence of a base such as sodium acetate or pyrrolidine with or without solvent at raised temperature. The resulting unsaturated intermediate of Formula (2-2) is reduced with a reducing agent such as lithium borohydride to give the desired product of formula I as a mixture of diastereomers (Scheme 2).

SCHEME 2

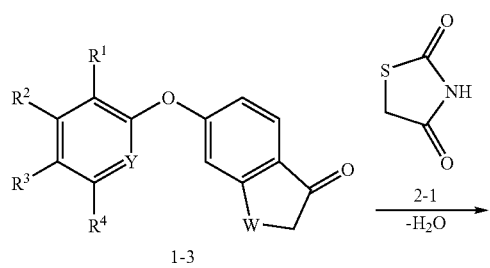

For the syntheses of the target compounds with indane (n=1) or tetraline (n=2) core structures, an alternative synthetic route is developed. Starting from methoxy indanone or tetralone (3-1), unsaturated ester (3-3) is prepared by Reformasky condensation with bromoacetate (3-2) according to a published procedure (WO 2004011446). Further hydrogenation gives saturated ester (34) which is enolated, silylated and brominated to yield alpha-bromo ester (3-5). TZD ring (3-7) is then formed by treatment of the bromo ester (3-5) with thiourea followed by hydrolysis of the resulting cyclic product (3-6). Demethylation of the intermediate (3-7) is performed with boron tribromide or aluminum trichloride to yield the key intermediate (3-8).

SCHEME 3

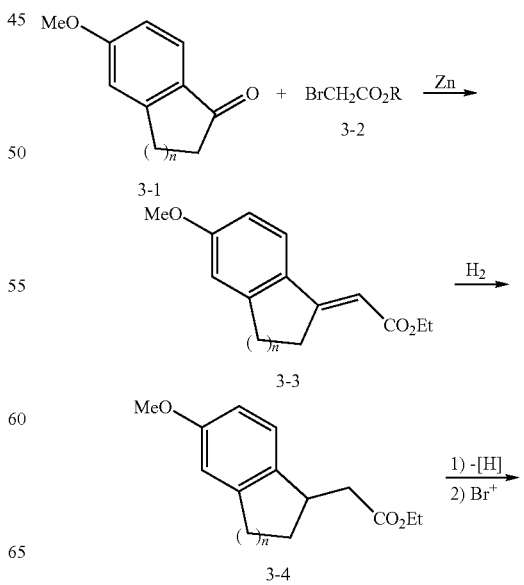

-continued

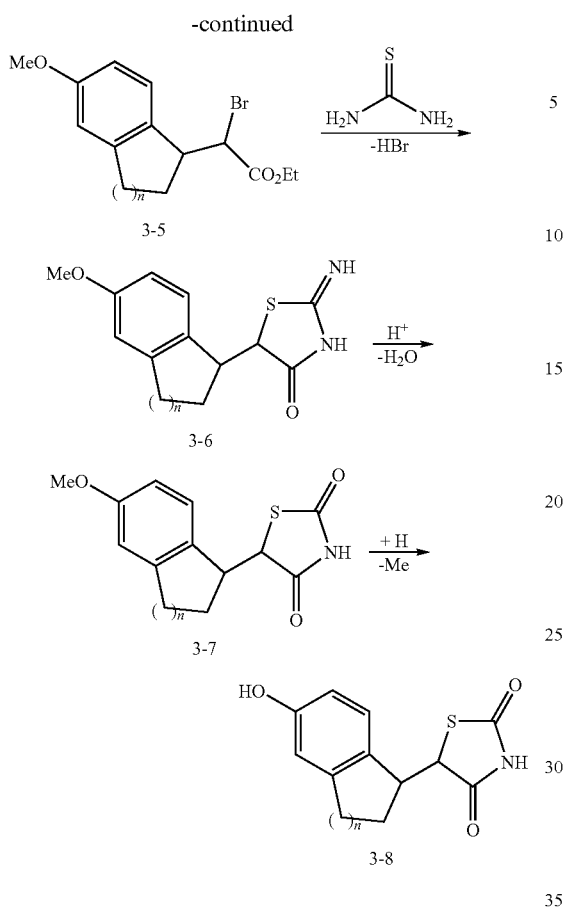

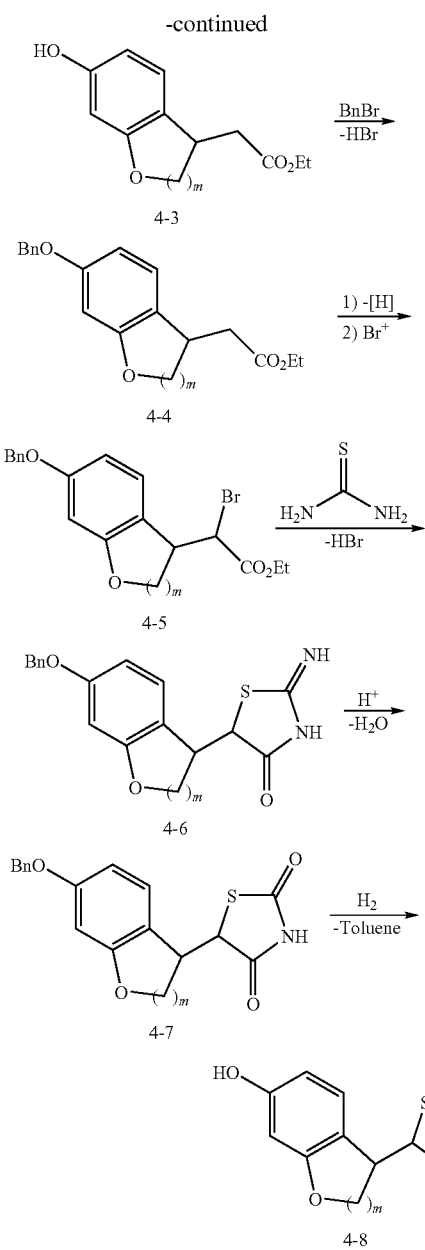

When W is an oxygen atom, the above procedure needs slight modification. Benzyloxy substituted ketones (4-1, m=1,2,3) undergoes Reformasky condensation with bromoacetate (3-2) to give unsaturated ester (4-2). Simultaneous saturation of the double bonds and debenzylation afford the hydroxylated saturated ester (4-3) which is reprotected by benzylation of the hydroxyl group to yield the intermediate (44). Following the same procedure described in Scheme 3, the TZD ring (4-6) is formed. Debenzylation is carried out by catalytic hydrogenation using diamine-treated palladium catalyst to give the intermediate (4-8).

SCHEME 4

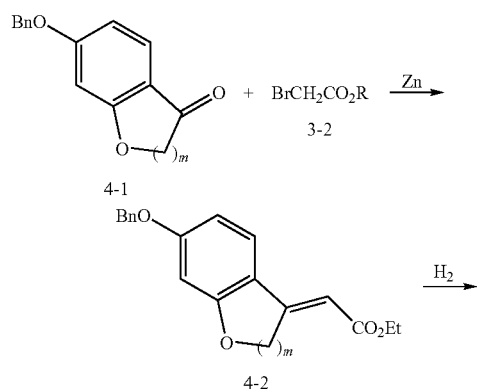

When W is a sulfur atom, the starting material (5-1) is used and the thiophene ring is saturated with triethyl silane/trifluoroacetic acid system. The resulting ester (5-2) undergoes similar reactions as described in Scheme 2 to give the key intermediate (5-6) (see Scheme 5).

SCHEME 5

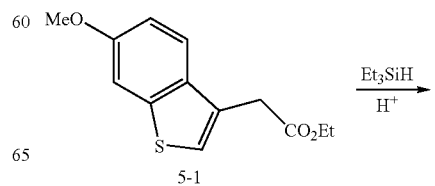

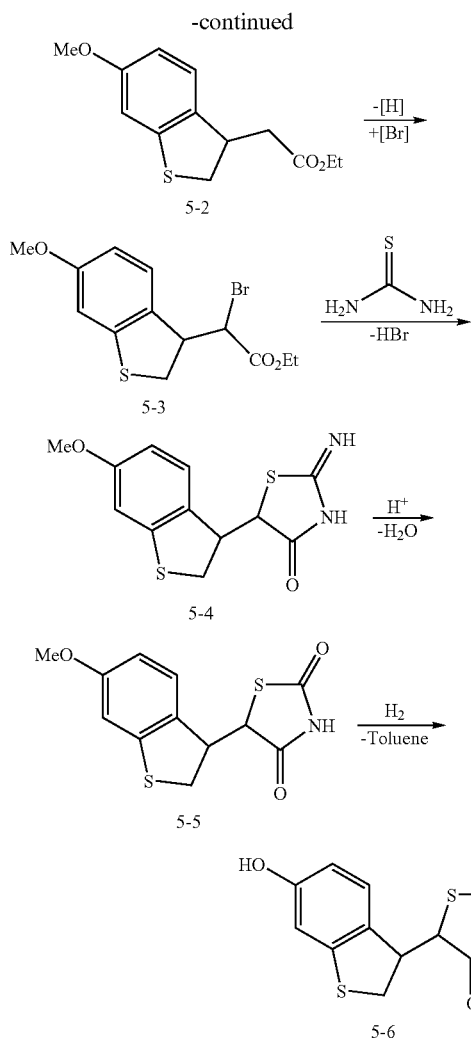

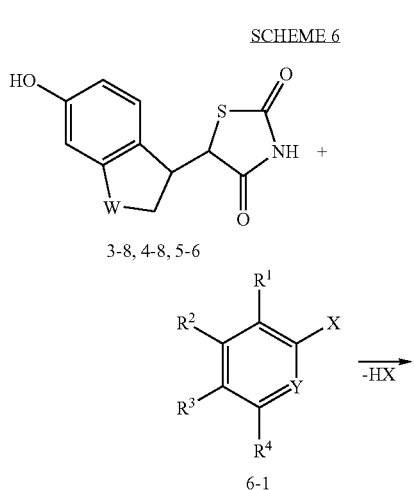

Final condensation (Scheme 6) of the intermediate (3-8, 4-8, 5-6) with haloarene (6-1) is carried out in the presence of a base such as cesium carbonate with or without catalyst such as CuCl/N,N-dimethylglycine.

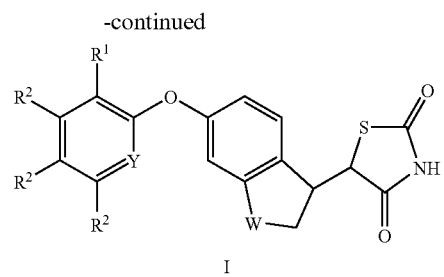

The replacement of the TZD head piece with 1,2,4-oxadiazolidine-3,5-dione is accomplished using different chemistry. For example, when A of formula I is a nitrogen atom and B is an oxygen atom, the target compounds are prepared according to the following procedures (Scheme 7). The intermediate ketone (1-3) is converted into the oxime (7-1) with hydroxylamine. Selective reduction of (7-1) to the hydroxylamine intermediate (7-2) is accomplished with sodium cyanoborohydride. After further conversion into the amide (7-3), cyclic product is obtained in two steps: first, treatment of (7-3) with methyl chloroformate, then treatment of the intermediate (7-4) with sodium hydride.

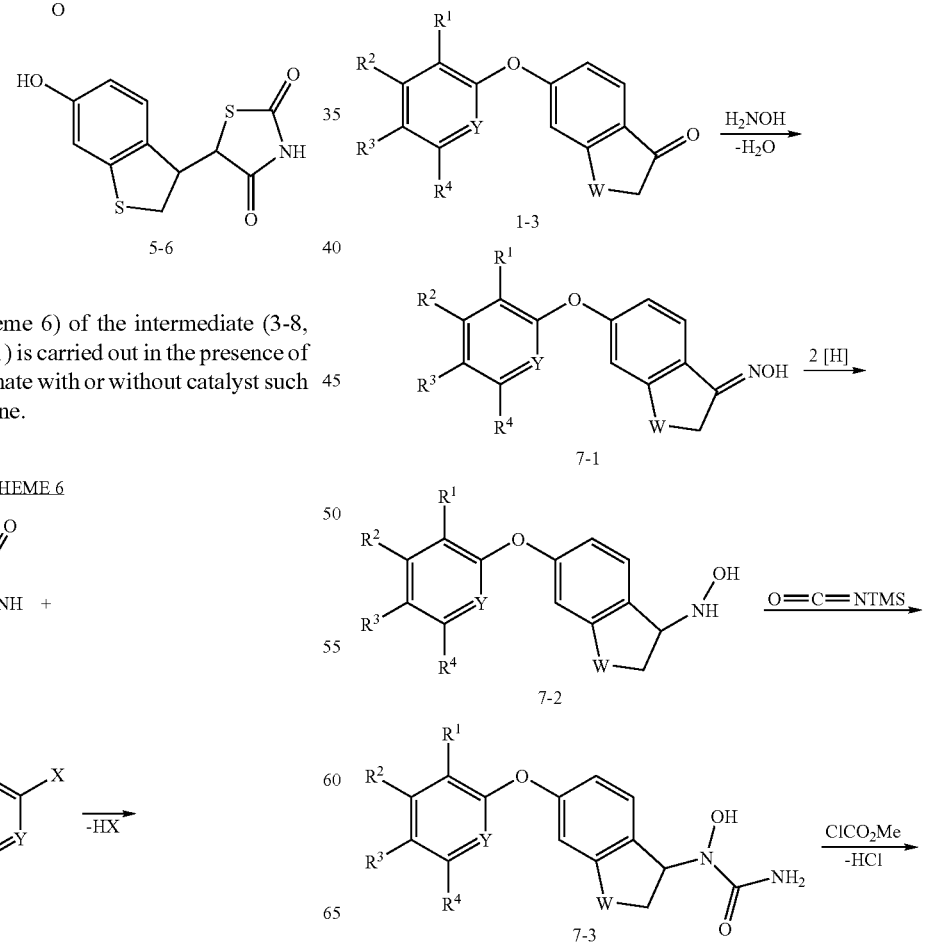

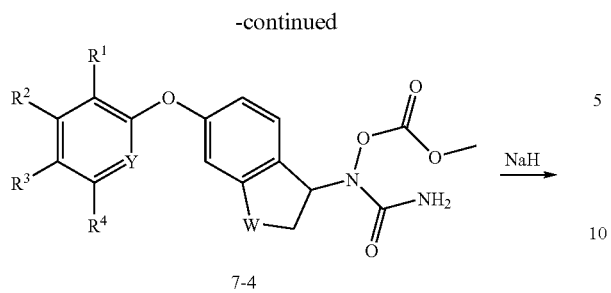

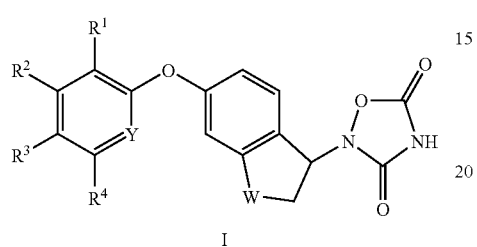

Another replacement of TZD head piece with imidazolidine-2,4-dione is done similarly (Scheme 8). The oxime (7-2) is hydrogenated to the amine (8-1) which is further converted into glycinate ester (8-2). Treatment of the amino ester with trichloroacetyl isocyanate followed by hydrolysis under basic condition gives the intermediate (8-3). The deprotection of trichloroacetyl and cyclization into the final target compound can be carried out in one pot under basic conditions such as potassium carbonate in hot methanol, ethanol or other alcohol.

SCHEME 8

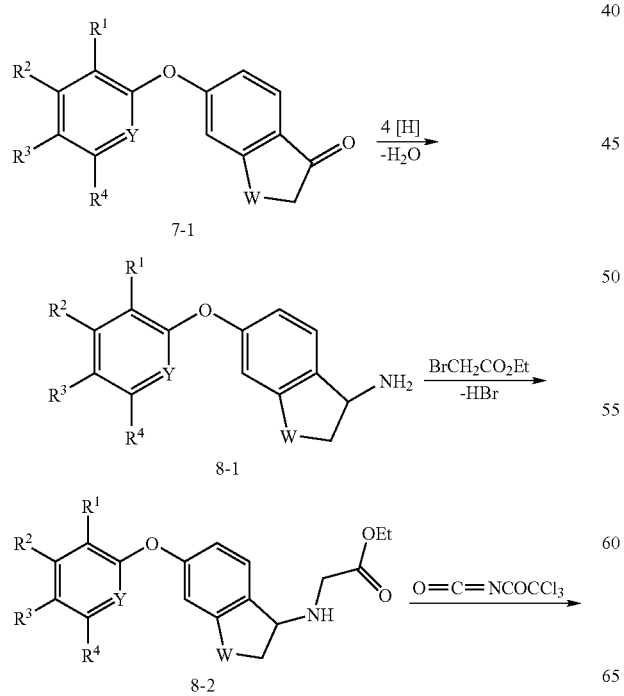

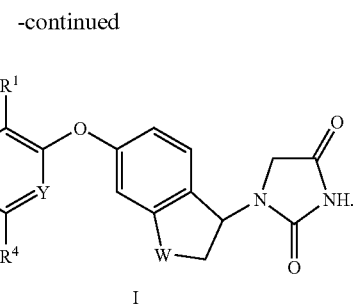

The replacement of the TZD headpiece with 1,3-oxazolidine-2,4-dione (OZD) is accomplished according to the procedures depicted in Scheme 9.

SCHEME 9

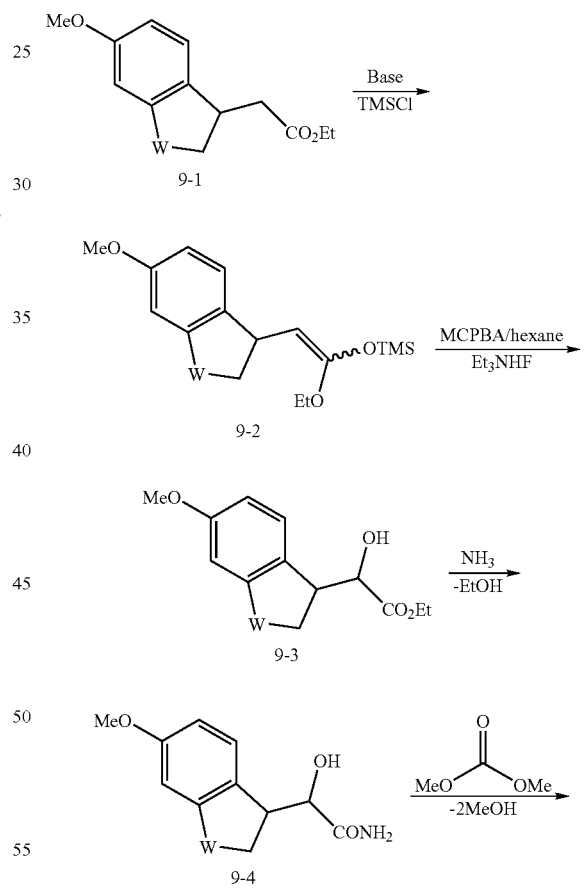

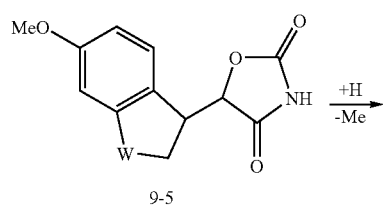

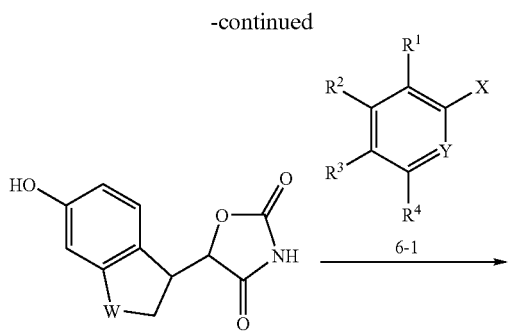

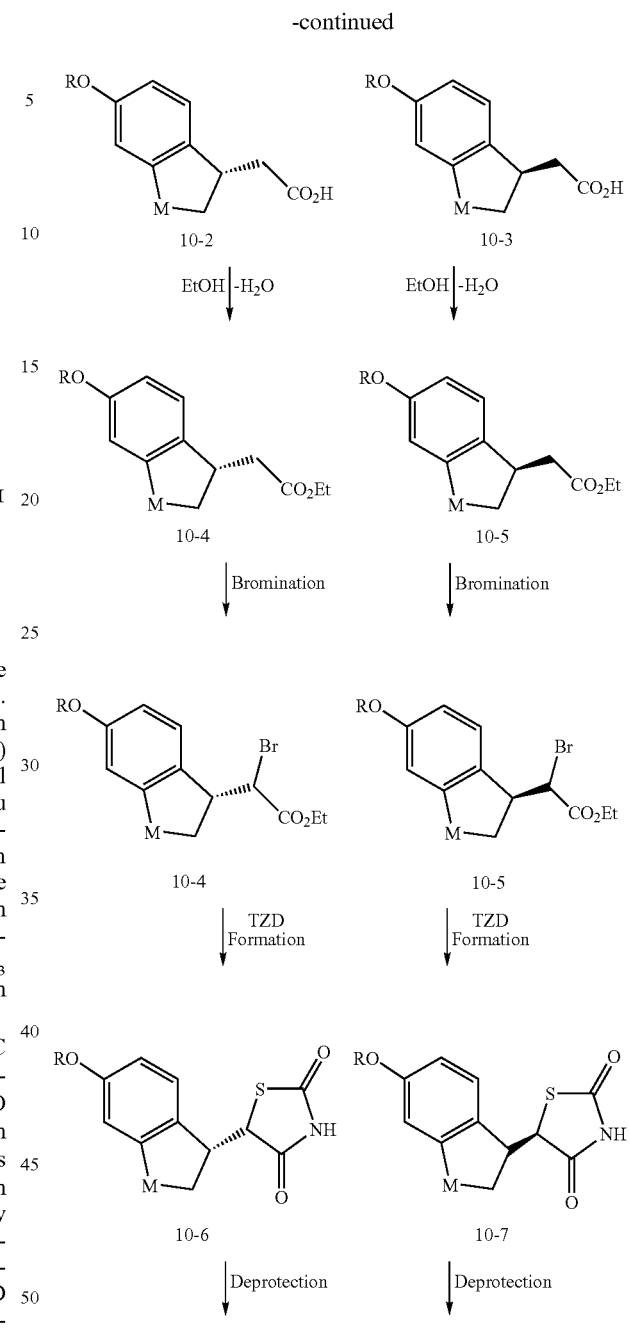

The hydroxylation of the ester (9-1) is accomplished by the previous procedure (G. M. Rubottom and R. Marrero, Synth. Commun., 1981, 11(6), 505-511). Treatment of (9-1) with a base such as potassium, lithium, sodium bis(trimethylsilyl) amide or LDA followed by trimethylsilyl chloride gives alkyl trimethylsilyl ketene acetal intermediate (9-2). The in situ treatment of (9-2) with MCPBA in hexane followed by treatment of the crude reaction mixture with triethyl ammonium fluoride leads to the production of α-hydroxy ester (9-3). The (9-3) is further converted into α-hydroxy amide (9-43) which can be cyclized into the OZD (9-5) by treatment with dimethyl carbonate. The demethylation of the (9-5) with $BBr_3$ affords the key intermediate (9-6) which undergoes smooth coupling with (6-1) to yield the final compound.

After chiral resolution of the starting acids by chiral HPLC or by using chiral amines such as (R) or (S)-methylbenzylamines according to the published procedures (WO 2004011446), the chiral intermediates (10-8) and (10-9) can be easily obtained by utilizing the same procedure as described in Scheme 3. The chiral (10-8) and (10-9) are each a mixture of two diastereomers whose relative ratio is highly dependent upon the ring size (ranges from 3:1 for a 5-membered ring to 6:1 for 6-membered ring). The major diastereomer can be purified on an HPLC. However, because the TZD ring is epimerized quickly in solution, it becomes a diastereomeric mixture again upon standing or storing.

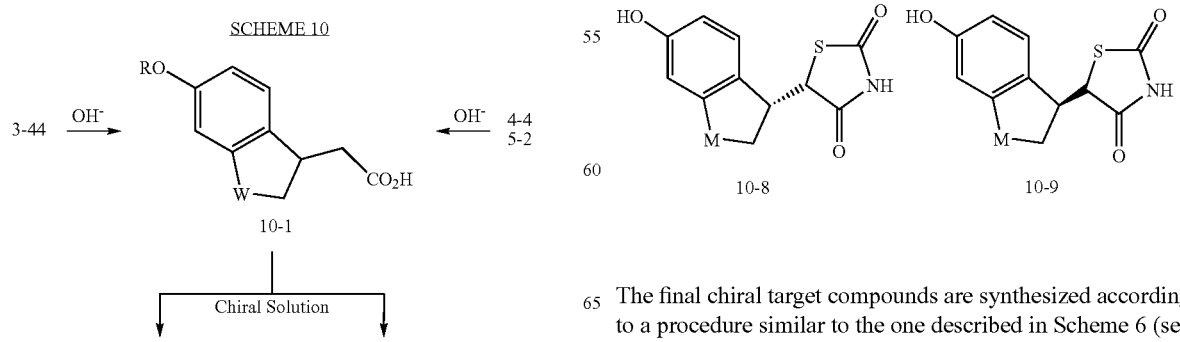

SCHEME 10

The final chiral target compounds are synthesized according to a procedure similar to the one described in Scheme 6 (see Scheme 11).

SCHEME 11

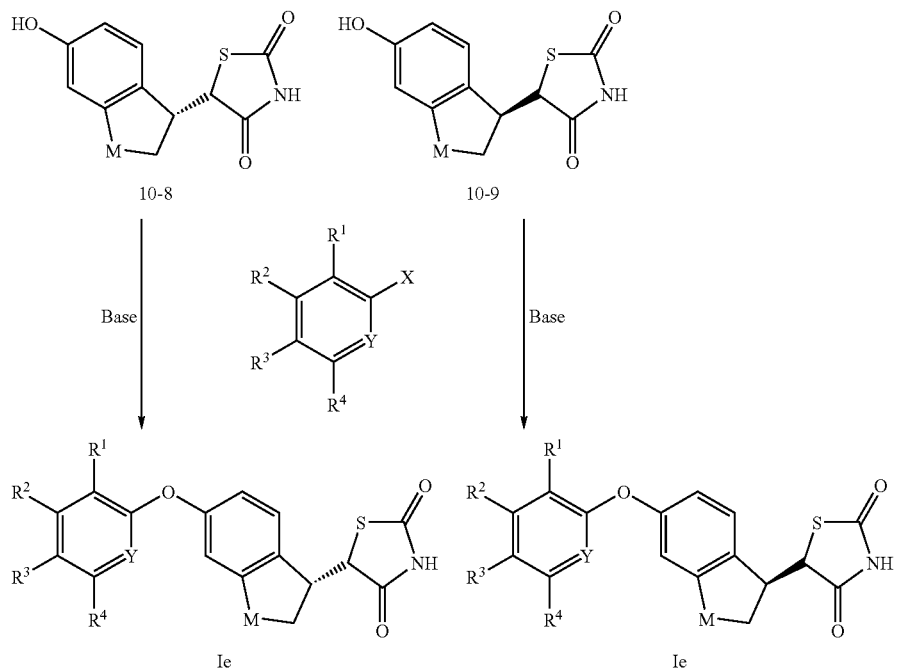

The following are representative procedures for the preparation of the synthetic intermediates used in the following Examples.

In some cases the order of carrying out the foregoing reaction schemes may be varied to facilitate the reaction or to avoid unwanted reaction products. The following examples are provided for the purpose of illustration only and are not to be construed as limitations on the disclosed invention.

Concentration of solutions was generally carried out on a rotary evaporator under reduced pressure. Flash chromatography was carried out on silica gel (230-400 mesh). MPLC refers to medium pressure liquid chromatography and was carried out on a silica gel stationary phase unless otherwise noted. NMR spectra were obtained in CDCl3 solution unless otherwise noted. Coupling constants (J) are in hertz (Hz). Abbreviations: diethyl ether (ether), triethylamine (TEA), N,N-diisopropylethylamine (DEA), saturated aqueous (sat'd), room temperature (rt), hour(s) (h), minute(s) (min).

Intermediate 1

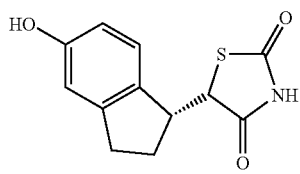

Step A

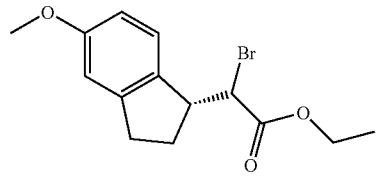

To a cooled (−78° C.) solution of ethyl [(1S)-5-methoxy-2,3-dihydro-1H-inden-1-yl]acetate (2.34 g, 10 mmol), prepared according to a published procedure (WO 20040011446), in 20 mL of anhydrous THF was added a solution of sodium bis(trimethylsilyl)amide (1.0 M, 12 mL, 12 mmol) dropwise. The mixture was stirred at −78° C. for 30 min, then a neat solution of trimethylsilyl chloride (1.4 mL, 11 mmol) was added dropwise. The reaction was stirred for an additional 10 min., solid NBS (2.0 g, 11 mmol) was added in one portion, the reaction was warmed to RT for one hour, quenched with water, and extracted with ethyl acetate. The organic phase was washed with water and brine, dried over anhydrous sodium sulfate, evaporated to afford a crude oil which was used in next step without further purification.

Step B

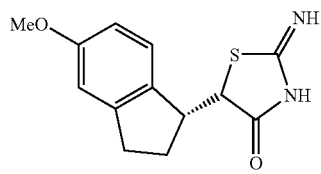

The crude product (3.70 g) from step A was treated with thiourea (0.76 g, 10 mmol) and sodium acetate (0.82 g, 10 mmol) in 50 mL of ethanol. The mixture was refluxed for 13 h, cooled at RT. After addition of 20 mL of ether and 20 mL of hexane, the resulting solid was collected by filtration and washing with hexane. The desired product was obtained as off white solid (1.72 g). LC-MS: calc. for C13H14N2O2S: 262; Found: 263 (M+H). 1H NMR (400 MHz, CD₃OD) δ 7.11, 6.90 (dd, J=8.1, 8.3 Hz, ratio=2:1, 1H), 6.58-6.76 (m, 2H), 5.03, 4.66 (dd, J=3.0, 2.8 Hz, ratio=2:1, 1H), 3.95 (m, 1H), 3.70 (s, 3H), 2.92 (m, 2H), 2.42, 2.05, 1.82, 1.70 (mmmm, 2H).

Step C

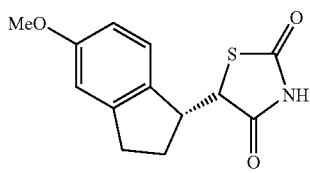

The product from step B was mixed with 50 mL of 2N aq. HCl and 50 μL of ethanol. The mixture was refluxed overnight (monitored by LC-MS until a complete conversion was observed). After removal of ethanol under vacuum, the residue was extracted with ethyl acetate, dried over anhydrous sodium sulfate, evaporated and dried in vacuum to afford a yellow solid. LC-MS: calc. for C13H13NO3S: 263 Found: 264 (M+H). 1H NMR (400 MHz, CD₃OD) δ 7.10, 6.96 (dd, J=8.3, 8.4 Hz, ratio=3:1, 1H), 6.60-6.80 (m, 2H), 5.11, 4.76 (dd, J=3.7, 4.1 Hz ratio=3:1, 1H), 4.0 (s, 1H), 3.72 (s, 3H), 3.0-2.7 (m, 2H), 2.40, 2.08, 1.90 (mmm, 2H).

Step D

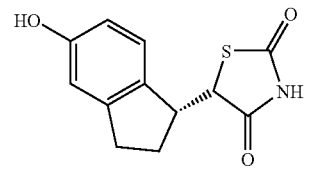

To a stirred, cool (−78° C.) solution of the product (1.40 g, 5.3 mmol) from step C in 10 mL of dichloromethane was added a solution of boron tribromide in dichloromethane (1.0 M, 15 mL, 15 mmol). The reaction was then warmed to RT for 30 min., then quenched with ice-water. The product was extracted with ethyl acetate twice. The organic phase was washed with water twice, dried with anhydrous sodium sulfate, and evaporated. The residue was dried under high vacuum to afford a light brown solid which could be used in next step without further purification. LC-MS: calc. for C12H11NO3S: 249 Found: 250 (M+H). 1H NMR (400 MHz, CD₃OD) δ 7.0, 6.9 (dd, J=8.2, 8.2 Hz, ratio=3:1, 1H), 6.50-6.62 (m, 2H), 5.08, 4.71 (dd, J=3.8, 4.2 Hz ratio=3:1, 1H), 3.90 (m, 1H), 3.72 (s, 3H), 2.92-2.70 (m, 21H), 2.38, 2.06, 1.86 (mmm, 2H).

Intermediate 2

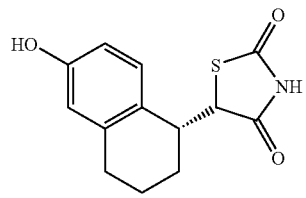

Step A

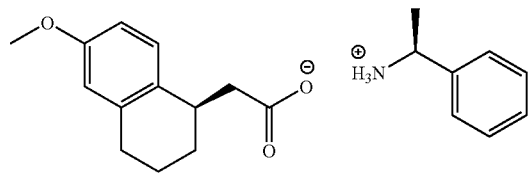

To a stirred solution of the racemic [6-methoxy-1,2,3,4-tetrahydronaphthalen-1-yl]acetic acid (69.4 g, prepared according to a published procedure (WO 2004011446) in 1500 mL of acetone was added 38.7 mL of (S)-alpha-methylbenzylamine in one portion. The mixture was stirred at RT for 30 min, then 1500 mL of hexane was added. The mixture was stirred for one hour. The resulting solid was removed by filtration and washing with hexane/acetone (4:1 v/v), and was then dried in air to give the first batch of solid. The combined mother liquids were stored at 0-5° C. overnight, the resulting solid was collected by filtration to give a second batch of solid. The two batches of the salt were combined, dissolved in a warm acetone (500 mL). 750 mL of hexane was added, and the mixture was stirred at RT for one hour. The resulting solid was collected by filtration, washed with hexane/acetone (4:1), and dried in air to give off-white crystals of (R,S)-salt.

Step B

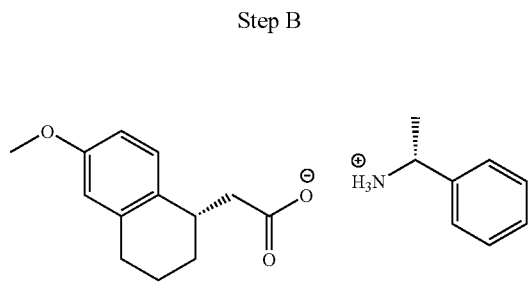

All mother liquids from the above step A were combined and condensed to give a light brown solid. 3N aq. HCl was added to adjust pH<3, stirred with ethyl acetate (500 mL), and separated. The organic phase was washed with 3N aq. HCl, dried over sodium sulfate, filtered and evaporated to afford a light brown solid (32 g, 145 mmol, S-enriched acid). This solid was dissolved in 500 mL of acetone, (R)-(+)-alpha-methylbenzylamine (16.6 mL, 145 mmol) was added, the mixture was refluxed until all the solid dissolved, and was then cooled to RT. The resulting precipitate was collected by filtration and washing with acetone to afford a white solid salt (S,R). The (S)-absolute configuration of the acid was con-

Step C

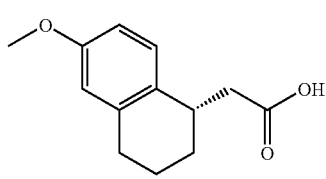

The (S,R) salt from the above step B (23.2 g) was stirred for one hour with 200 mL of 3N HCl and 200 mL of ethyl acetate. The organic phase was separated and washed with 3N aq. HCl (2×100 mL), dried over sodium sulfate, filtered and evaporated to give the desired (S)-acid as a light brown solid.

Step D

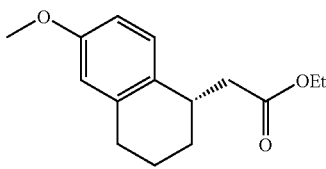

The (S)-acid from the above step D (14 g) was dissolved in 150 mL of ethanol, and 19 mL of trimethylsilyl chloride was added. The mixture was stirred at RT overnight, and was then evaporated and mixed with ethyl acetate (100 mL). The organic phase was washed with water and saturated aq. sodium hydrogen carbonate, dried over sodium sulfate, and purified on FC (Silica gel, 20% ethyl acetate/hexane) to give the desired (S)-ester as a colorless oil. 1H NMR (400 MHz, CDCl$_3$) δ 7.04 (d, J=7.7 Hz, 1H), 6.67 (m, 1H), 6.60 (m, 1H), 4.14 (m, 2H), 3.74 (bs, 3H), 3.26 (m, 1H), 2.80-2.40 (m, 4H), 1.90-1.60 (m, 4H), 1.24 (m, 3H).

Step E

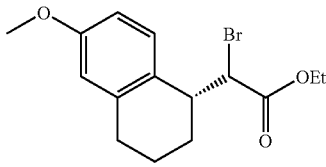

To a cooled (−78° C.) solution of ethyl [(1S)-6-methoxy-1,2,3,4-tetrahydronaphthalen-1-yl]acetate (7.45 g, 30 mmol), from the above step D, in 50 mL of anhydrous THF was added a solution of sodium bis(trimethylsilyl)amide (1.0 M, 36 mL, 36 mmol) dropwise. The mixture was stirred at −78° C. for 30 min, then a neat solution of trimethylsilyl chloride (4.22 mL, 33 mmol) was added dropwise. The reaction was stirred for additional 10 min. Solid NBS (5.87 g, 33 mmol) was added in one portion. The reaction was warmed to RT during one hour, quenched with water, and extracted with ethyl acetate. The organic phase was washed with water and brine, dried over anhydrous sodium sulfate, and evaporated to afford a crude oil which was used in next step without further purification.

Step F

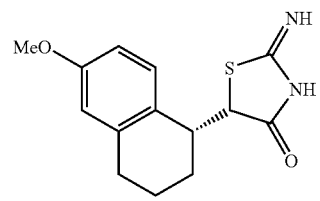

The crude product from the above step E was treated with thiourea (2.28 g, 30 mmol) and sodium acetate (2.46 g, 30 mmol) in 50 mL of ethanol. The mixture was refluxed for 13 b, cooled at RT. After addition of 20 mL of ether and 20 mL of hexane, the resulting solid was collected by filtration and washing with hexane. The desired product was obtained as off white solid. LC-MS: calc. for C14H16N2O2S: 276; Found: 277 (M+H).

Step G

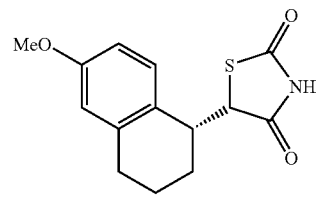

The product from the above step F was mixed with 50 mL of 4N aq. HCl and 50 mL of ethanol. The mixture was refluxed overnight (monitored by LC-MS until a complete conversion was observed). After removal of ethanol under vacuum, the residue was extracted with ethyl acetate, dried over anhydrous sodium sulfate, evaporated, and dried in vacuum to afford a yellow solid. LC-MS: calc. for C14H15NO3S: 277 Found: 278 (M+H).

Step H

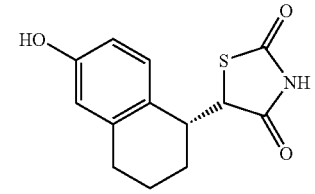

To a stirred, cool (−78° C.) solution of the product from the above step G (5.2 g, 18.7 mmol) in 50 mL of dichloromethane was added a solution of boron tribromide in dichloromethane (1.0 M, 57 mL, 57 mmol). The reaction was then warmed to RT for 30 min. and quenched with ice-water. The product was extracted with ethyl acetate twice. The organic phase was washed with water twice, dried with anhydrous sodium sulfate, and evaporated. The residue was dried under high vacuum to afford a light brown solid which could be used in next step without further purification. LC-MS: calc. for C13H13NO3S: 264 Found: 265 (M+H).

Intermediate 3

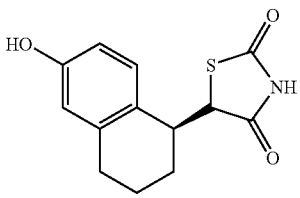

Step A

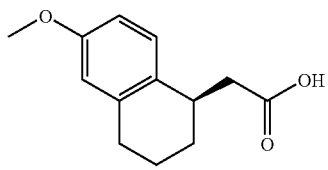

The (R,S) salt (24.5 g) from step A of the synthesis of Intermediate 2 was stirred for one hour with 200 mL of 3N HCl and 200 mL of ethyl acetate. The organic phase was separated and washed with 3N aq. HCl (2×100 mL), dried over sodium sulfate, filtered, and evaporated to give the desired (R)-acid as a light brown solid.

Step B

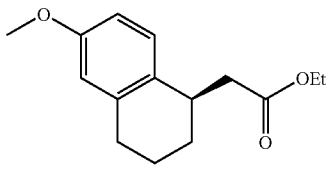

The (R)-acid from the above step A (15.6 g) was dissolved in 150 mL of ethanol followed by addition of 19 mL of trimethylsilyl chloride. The mixture was stirred at RT overnight, evaporated and mixed with ethyl acetate (100 mL). The organic phase was washed with water and saturated aq. sodium hydrogen carbonate, dried over sodium sulfate, and purified on FC (Silica gel, 5% ethyl acetate/hexane) to give the desired (R)-ester as a colorless oil.

Step C

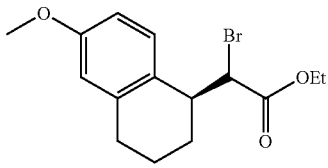

To a cooled (−78° C.) solution of ethyl [(1R)-6-methoxy-1,2,3,4-tetrahydronaphthalen-1-yl]acetate (7.45 g, 30 mmol), from the above step B, in 50 mL of anhydrous THF was added a solution of sodium bis(trimethylsilyl)amide (1.0 M, 36 mL, 36 mmol) dropwise. The mixture was stirred at −78° C. for 30 min. A neat solution of trimethylsilyl chloride (4.22 mL, 33 mmol) was added dropwise. The reaction was stirred for an additional 10 min., and solid NBS (5.87 g, 33 mmol) was added in one portion. The reaction was warmed to RT during one hour, quenched with water, and extracted with ethyl acetate. The organic phase was washed with water and brine, dried over anhydrous sodium sulfate, and evaporated to afford a crude oil which was used in next step without further purification.

Step D

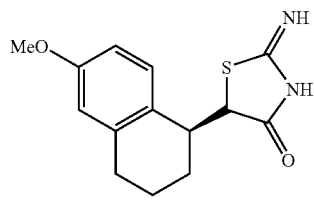

The crude product from the above step C was treated with thiourea (2.28 g, 30 mmol) and sodium acetate (2.46 g, 30 mmol) in 50 mL of ethanol. The mixture was refluxed for 13 h, and cooled to RT. After addition of 20 mL of ether and 20 mL of hexane, the resulting solid was collected by filtration and washed with hexane. The desired product was obtained as off white solid. LC-MS: calc. for C14H16N2O2S: 276; Found: 277 (M+H).

Step E

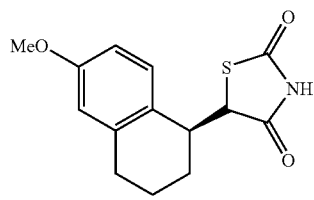

The product from the above step D was mixed with 50 mL of 4N aq. HCl and 50 mL of ethanol. The mixture was refluxed overnight (monitored by LC-MS until a complete conversion was observed). After removal of ethanol under vacuum, the residue was extracted with ethyl acetate, dried over anhydrous sodium sulfate, and evaporated and dried in vacuum to afford a yellow solid. LC-MS: calc. for C14H15NO3S: 277 Found: 278 (M+H).

Step F

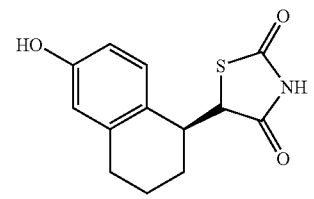

To a stirred, cool (−78° C.) solution of the product from the above step E (4.02 g, 14.5 mmol) in 50 mL of dichloromethane was added a solution of boron tribromide in dichloromethane (1.0 M, 30 mL, 30 mmol). The reaction was then warmed to RT for 30 min., and quenched with ice-water. The product was extracted with ethyl acetate twice. The organic phase was washed with water twice, dried with anhydrous sodium sulfate, and evaporated. The residue was dried under high vacuum to afford a light brown solid which could be used in the next step without further purification. LC-MS: calc. for C13H13NO3S: 264 Found: 265 (M+H).

Intermediate 4

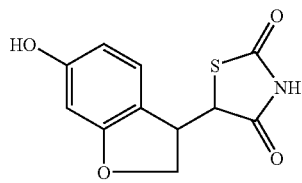

Step A

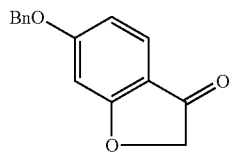

To 6-hydroxyl-2,3-dihydrobenzofuran-3-one (30 g, 200 mmol) in DMF (600 mL) was added $K_2CO_3$ (220 mmol, 30.4 g) followed by BnBr (200 mmol, 24 mL). After stirring at room temperature for 3 hours, the reaction mixture was partitioned between methyl t-butyl ether (MTBE, 500 mL) and water (1 L). The aqueous layer was separated and further extracted with MTBE (2×500 mL). The organic layers were combined, washed with water (500 mL), Brine (500 mL), dried over anhydrous $Na_2SO_4$, filtered and concentrated in vacuo to give 6 as a yellow solid. LC-MS for $C_{15}H_{13}O_3$ [M+H$^+$]: calculated 241.1, found 241.1.

Step B

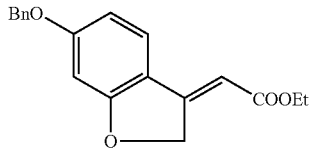

To a suspension of NaH (60% in mineral oil, 381 mmol, 15.2 g) in anhydrous THF (900 mL) was added triethyl phosphonoacetate (381 mmol, 76 mL) dropwisely in an ice bath. After addition, the reaction was stirred at room temperature for 20 minutes until a clear solution was obtained. A solution of the ketone (45.7 g, 190 mmol) from Step A in THF (100 mL) was then added to the reaction. The reaction was stirred overnight at room temperature and then quenched with 0.1N HCl (1 L). The aqueous layer was separated and extracted with EtOAc (2×500 mL). The organic layers were combined, washed with water (500 mL), then Brine (500 mL), then dried over anhydrous $Na_2SO_4$, filtered, and concentrated in vacuo. The residue was purified by flash chromatography (10% to 30% EtOAc/hexanes) to give 7 as a yellow solid. LC-MS for $C_{19}H_{20}O_4$ [M+H$^+$]: calculated 311.1, found 311.3.

Step C

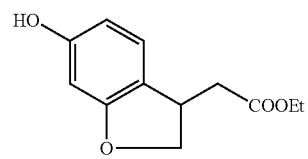

To a solution of the unsaturated ester (6.6 g, 21.3 mmol) from Step B in ethanol (75 mL) and EtOAc (75 mL) was added 10% Pd/C (2 g). The mixture was hydrogenated in a par-shaker at 50 psi for 2 hours. The mixture was then filtered through celite. The filtrate was concentrated in vacuo to give 8 as red oil. LC-MS for $C_{12}H_{15}O_4$ [M+H$^+$]: calculated 223.2, found 223.2.

Step D

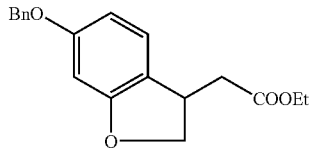

To a solution of the acid (2 g, 9 mmol) from Step C in DMF (15 mL) and acetone (60 mL) was added $K_2CO_3$ (11 mmol, 1.5 g) followed by BnBr (11 mmol, 1.3 mL). The reaction was stirred overnight at room temperature and then concentrated in vacuo. The residue was partitioned between EtOAc (100 mL) and water (200 mL). The aqueous layer was separated and further extracted with EtOAc (2×100 mL). The organic layers were combined, washed with water (100 mL), then Brine (100 mL), then dried with anhydrous $Na_2SO_4$, filtered and concentrated in vacuo. The residue was purified by silica gel flash chromatography (0% to 15% EtOAc/hexanes) to give 9 as oil. 1H NMR (500 MHz, CDCl$_3$) δ 7.50-7.30 (m, 5H), 7.06 (d, J=8.0 Hz, 1H), 6.52 (d, J=8.2 Hz, 1H), 6.50 (bs, 1H), 5.0 (s, 2H), 4.8 (t, J=8.9 Hz, 1H), 4.30 (dd, J=6.1, 8.9 Hz, 1H), 4.2 (q, J=7.1 Hz, 2H), 4.85 (m, 1H), 2.75 (dd, J=5.5, 16.5 Hz, 1H), 2.58 (dd, J=9.1, 16.2 Hz, 1H), 1.30 (t, J=7.1 Hz, 3H). LC-MS for $C_{19}H_{21}O_4$ [M+H$^+$]: calculated 313.4, found 313.2.

Step E

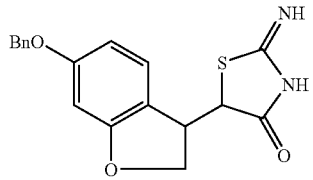

To a flame-dried flask was added anhydrous THF (30 mL) followed by NaHMDS (7.5 mmol, 7.5 mL of 1 M THF solution). After cooling to −78° C., a solution of the ester (2.0 g, 6.3 mmol) from Step D in THF (10 mL) was added to the reaction slowly. After addition, the reaction was stirred at −78° C. for 15 minutes before TMSCl (7.2 mL of 1 M solution in THF, 7.2 mmol) was added. After another 30 minutes at −78° C., NBS (6.9 mmol, 1.2 g) was added in one portion. The reaction was allowed to warm up to 0° C. over 2 hours before being quenched with 0.1 N HCl (200 mL). The aqueous layer was separated and further extracted with EtOAc (2×100 mL). The organic layers were combined, washed with water (100 mL), then Brine (100 mL), then dried over anhydrous Na$_2$SO$_4$, filtered, and concentrated in vacuo. The residue was purified by silica gel flash chromatography (0% to 18% EtOAc/hexanes) to give 2.3 g of oil. This oil was then dissolved in ethanol (40 mL), and thiourea (7.0 mmol, 0.54 g) and NaOAc (12 mmol, 0.96 g) were added. The reaction was refluxed for 24 hours and then cooled back to room temperature. The suspension was then filtered. The solid was further washed with cold EtOH (4 mL) and dried in air to give compound 10 as a white solid. LC-MS for C$_{19}$H$_{17}$N$_2$O$_3$S [M+H$^+$]: calculated 341.1, found 341.1.

Step F

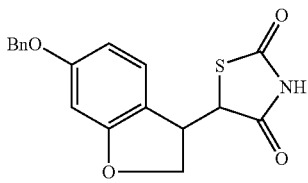

A suspension of the cyclic product (1.5 g, 4.4 mmol) from Step E in EtOH (20 mL) and 6 N HCl (4 mL) was refluxed overnight. The reaction was then concentrated in vacuo. The residue was purified by silica gel flash chromatography (0% to 50% EtOAc/hexanes) to give the desired TZD as a mixture of diastereomers. LC-MS for C$_{18}$H$_{16}$NO$_4$S [M+H$^+$]: calculated 342.1, found 342.1.

Step G

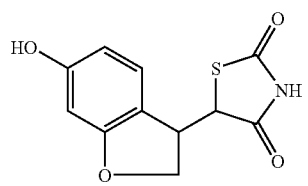

To a suspension of the methoxy TZD (300 mg, 0.88 mmol) from Step F in EtOH (20 mL) was added 4 N HCl in dioxane (500 uL and 10% Pc/C (500 mg). The reaction was hydrogenated at 1 atm for 2 hours to give a completed reaction. The mixture was then filtered through celite. The filtrate was concentrated in vacuo to give INTERMEDIATE 4 as a yellow solid. LC-MS for C$_{11}$H$_{10}$NO$_4$S [M+H$^+$]: calculated 252.0, found 252.1.

Intermediate 5

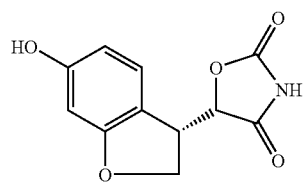

Step A

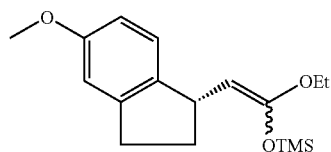

To a cooled (−78° C.) solution of ethyl [(1S)-5-methoxy-2,3-dihydro-1H-inden-1-yl]acetate (2.34 g, 10 mmol), prepared according to a published procedure (WO 20040011446), in 20 mL of anhydrous THF was added a solution of sodium bis(trimethylsilyl)amide (1.0 M, 12 mL, 12 mmol) dropwise. The mixture was stirred at −78° C. for 30 min, then a neat solution of trimethylsilyl chloride (1.4 mL, 11 mmol) was added dropwise. The reaction was stirred for an additional 30 min., then the reaction vessel was gradually warmed to room temperature. Solvent was then removed in vacuo (roto-evaporation) and then ca. 75 mL of pentane was added to the residue. Rapid filtration and removal of solvent in vacuo yielded crude alkyl trimethyl ketene acetal.

Step B

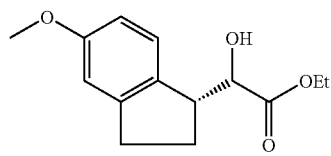

A pre-cooled (ice-methanol) stirred solution of 2.35 g (77% purity, 10 mmol) of MCPBA in 100 mL of dry hexane under an atmosphere of nitrogen was treated with a solution containing 10 mmol of the above acetal in 100 mL of dry hexane. After addition was complete (ca. 5 min), the resulting slurry was stirred for 30 min at room temperature. The reaction mixture was then treated with 1.2 g (10 mmol) of triethylammonium fluoride with stirring, which continued for 30 min after addition was completed. The mixture was then filtered, and the filtrate was diluted with 100 mL of ethyl acetate. The solution was then washed sequentially with 200 mL of 5% aqueous hydrochloric acid and 2×200 mL of 5% aqueous sodium carbonate. The organic layer was then dried using anhydrous sodium sulfate. Filtration and solvent removal in vacuo gave crude hydroxyl ester. The pure compound was then obtained on Combi-Flash (5-10% ethyl acetate/hexane). LC-MS for C$_{14}$H$_{18}$O$_4$ [M+H$^+$]: calculated 250, found 251. 1H NMR (400 MHz, CDCl₃) (major isomer) δ 7.2 (d, 1H), 6.72 (s, 1H), 6.05 (d, 1H), 4.28 (d, 1H), 4.18 (m, 2H), 3.68 (s, 1H), 3.52 (m, 1H), 2.90 (m, 1H), 2.72 (m, 1H), 2.10 (m, 2H), 1.22 (t, 3H).

Step C

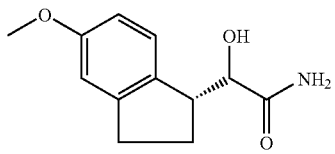

The hydroxyl ester obtained from Step B was mixed with 4N ammonia-methanol (50 mL) overnight, evaporated and the residue was mixed with 5 mL of ethyl acetate and 20 mL of hexane. The resulting white powder was filtered and washed with hexane, dried in high vacuo to give the pure product as single isomer. LC-MS for $C_{12}H_{15}NO_3$ [M+H⁺]: calculated 221, found 222. 1H NMR (400 MHz, CDCl₃) δ 7.12 (d, J=8.1 Hz, 1H), 6.77 (m, 2H), 6.55 (bs, 1H), 5.53 (bs, 1H), 4.54 (s, 1H), 3.76 (s, 3H), 2.82 (m, 2H), 2.12 (m, 1H), 2.00 (m, 1H), 1.98 (m, 1H).

Step D

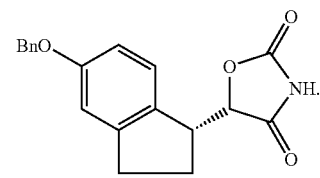

The hydroxy amide (280 mg, 1.267 mmol) and diethyl carbonate (747 mg, 6.335 mmol) were mixed with sodium methoxide (345 mg, 6.335 mmol) and ethanol (10 mL). The mixture was refluxed for 1.5 h, evaporated. The residue was acidified with 3N aq. HCl, extracted with ethyl acetate, dried over sodium sulfate, evaporated and purified on Comb-Flash (5-30% ethyl acetate/hexane) to give the product. LC-MS calc. for C13H13NO4: 247; Found: 248 (M+H). 1H NMR (400 MHz, CDCl₃) (major isomer) δ 7.17 (d, J=8.0 Hz, 1H), 6.75 (m, 2H), 5.10 (s, 1H), 3.75 (s, 3H), 3.00 (m, 1H), 2.84 (m, 1H), 2.22 (m, 2H), 2.04 (m, 1H). Major/minor ~6:1.

Step E

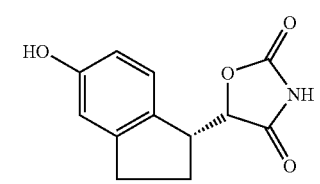

To a stirred, cool (−78° C.) solution of the product from the above step D (100 mg, 0.4 mmol) in 5 mL of dichloromethane was added a solution of boron tribromide in dichloromethane (1.0 M, 1.0 mL, 1.0 mmol). The reaction was warmed to RT for 50 min., then quenched with ice-water. The product was extracted with ethyl acetate twice. The organic phase was washed with water twice, dried with anhydrous sodium sulfate, and evaporated. The residue was dried under high vacuum to afford a light brown solid which could be used in next step without further purification. LC-MS: calc. for C12H11NO4: 233 Found: 234 (M+H).

Intermediate 6

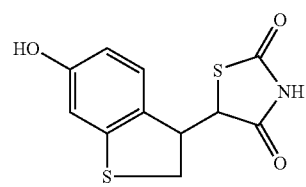

Step A

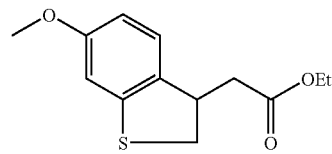

Ethyl (6-methoxy-1-benzothien-3-yl)acetate (2.50 g, 10 mmol) was refluxed together with triethylsilane (5 mL) and trifluoroacetic acid (10 mL) overnight. TFA was removed under vacuo and the residue was diluted with ethyl acetate, washed with water and sat. aq. sodium carbonate, and then was dried over sodium sulfate, filtered, evaporated, and purified by FC (silica gel, 10% ethyl acetate/hexane) to give the product.

Step B

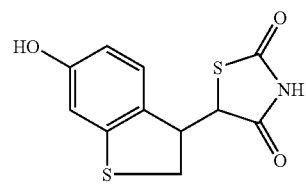

The compound was prepared according to the same producers as in the preparation of INTERMEDIATE 1 by replacing [(1S)-5-methoxy-2,3-dihydro-1H-inden-1-yl]acetate with ethyl (6-methoxy-2,3-dihydro-1-benzothien-3-yl)acetate.

LC-MS calc. for C11H9NO3S2: 267; Found: 268 (M+H).

Intermediate 7

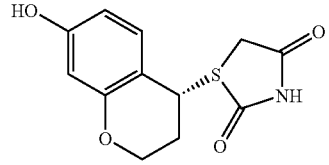

Step A

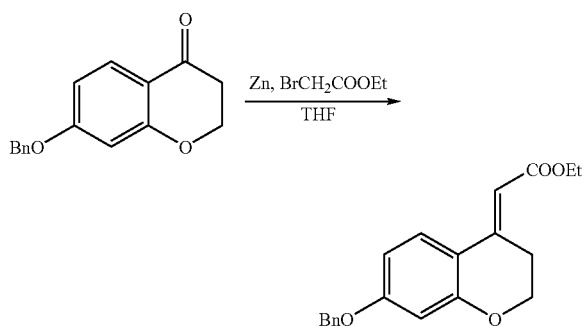

To a dried 3-neck 2 L round bottom was added freshly azeotroped 7-(benzyloxy)chroman-4-one (287 g, 1.13 mol, synthesized according to *J. Med. Chem.* 1998, 41, 1172-1184) and 2 L of anhydrous THF (no inhibitor). Zinc (124.9 g, 1.92 mol) and CuI (10.7 g, 56.5 mmol) were then quickly added to the reaction solution. After refluxing for 30 minutes under $N_2$ atmosphere, 81 mL of ethyl bromoacetate (½ of total needed, F.W. 167.01, d 1.506, 0.7 mol) was added dropwise to the refluxing mixture. Heat was then turned off and the reaction was stirred at ambient temperature for 4-5 h. Another 81 ml of ethyl bromoaceate (F.W. 167.01, d 1.506, 0.7 mol) was then added dropwise and the reaction was stirred without heating until the reaction temperature returned to ambient temperature. Solids were removed by vacuum filtration through celite and the filtrate was concentrated to ~800 mL by rotary evaporation, which was poured into 1 L of 1N HCl (aq) with 1000 g of ice, and stirred vigorously for 30 min. The mixture was extracted with EtOAc (1×2 L, 2×1 L). The combined organic layers was washed with $H_2O$ (1×3 L), Brine (1×2 L), dried over $Na_2SO_4$, and concentrated in vacuo. The crude compound was used without further purification.

Step B

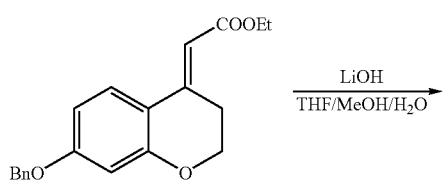

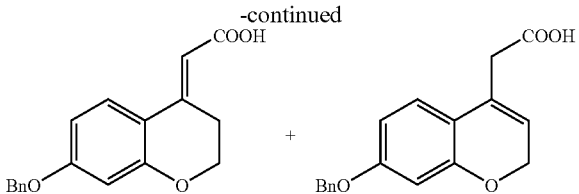

To a solution of crude product (~356 g, 1.1 mol) from step A in THF/MeOH/$H_2O$ (2:2:1, 2.5 L) was added LiOH.$H_2O$ (92.4 g, M.W. 41.96, 2.2 mol). The reaction was stirred at ambient temperature overnight. The organic solvents were removed in vacuo and the residue was diluted with water to 3 L in volume. This aqueous solution was washed with diethyl ether (2×500 mL) and the aqueous layer was then acidified to pH=1 with 10 N HCl (aq). The solid was isolated by vacuum filtration, washed with EtOAc and dried under vacuum. The filtrate was extracted with EtOAc (2×500 mL). The combined organics were washed with brine (400 mL) and concentrated in vacuo. All solids were combined, triturated with minimal EtOAc, and dried under high vacuum to give a mixture of two isomers.

Step C

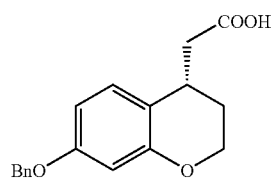

A solution of product from step B (20 g, 67.6 mmol) in anhydrous methanol (800 mL) was degassed by bubbling through $N_2$ for 1 hour. (R)-BINAP $RuCl_2$ (1.11 g, F. W. 794.65, 1.4 mmol) and 950 µL of freshly degassed triethylamine (F.W. 101.19, d 0.72, 6.76 mmol) were quickly added under $N_2$ atmosphere. The mixture was hydrogenated under $H_2$ (50 psi) for 4 days. The mixture was then filtered and the filtrate was concentrated in vacuo. The residue was purified by column chromatography to give the desired product (70% ee) and recovered starting material. The product was dissolved in minimal EtOAc (~20 mL) and petroleum ether (~20 mL) and re-crystallized to give chiral acid (~95% ee).

Step D

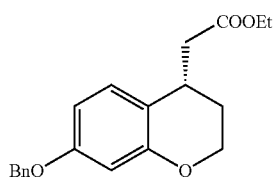

A solution of chiral acid from step C (6.5 g, 21.8 mmol) in 100 mL of 6 N HCl/EtOH, was stirred at RT for 5 hour. The reaction was then concentrated in vacuo to give the desired chiral ester. 1H NMR (400 MHz, $CDCl_3$) δ 7.5-7.25 (m, 5H), 7.0 (d, J=10 Hz, 1H), 6.55 (m, 1H), 6.44 (s, 1H), 5.01 (s, 2H), 4.20-4.12 (m, 4H), 3.34-3.28 (m, 1H), 2.78-2.73 (m, 1H), 2.51-2.45 (m, 1H), 2.18-2.10 (m, 1H), 1.85-1.78 (m, 1H), 1.30-1.24 (m, 3H).

Step E

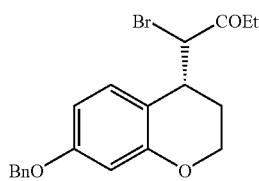

To a solution of chiral ester from step D (7.3 g, 22.4 mmol) in anhydrous THF (100 mL) was added NaHMDS (2.0M in THF, 14.6 mL, 29.2 mmol) at −78° C. After addition, the reaction was stirred at −78° C. for 30 minutes before TMSCl (2.0M in THF, 13.5 mL, 26.9 mmol) was added. After the addition of TMSCl, the reaction was stirred for another 30 minutes and NBS (4.4 g, 24.7 mmol) was added in one portion. The reaction was allowed to warm up to 0° C. over 2-3 hours. The reaction was partitioned between 0.1 N HCl aq (200 mL) and ethyl acetate (200 mL). The organic layer was washed with 0.1 N HCl aq (1×200 mL). The aqueous layers were combined and back-extracted with EtOAc (1×100 mL). The organic layers were combined and washed with Brine (2×100 mL), dried over $Na_2SO_4$ and concentrated in vacuo to give the desired product. This crude material was used without further purification.

Step F

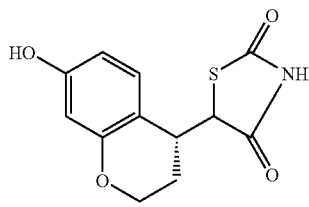

To the crude material from step E (~20 mmol) in 100 mL of EtOH was added thiourea (M.W. 76.12, 1.979 g, 26 mmol) and sodium acetate (M.W. 82.03, 3.281 g, 40 mmol). The reaction was refluxed overnight. The organic solvent was removed in vacuo and the residue was partitioned between 50 mL of 6 N HCl (aq) and 50 mL of EtOAc. The organic layer was further extracted with 6 N HCl (aq) (2×25 mL). The aqueous layers were combined and further washed with EtOAc (1×10 mL). The aqueous layer was separated and EtOH (50 mL) was added to the aqueous solution. This solution was refluxed for 24 hours and then cooled to room temperature. The reaction was diluted with water (400 mL) and extracted with EtOAc (1×400 mL, 2×200 mL). The organic layers were combined and washed with Brine (1×100 mL), dried over $Na_2SO_4$ and concentrated in vacuo. The residue was purified by column chromatography (silica, 0-20% EtOAc/$CH_2Cl_2$) to afford the desired INTERMEDIATE 7. LC-MS negative [M−H]: calc. for $C_{12}H_{10}NO_4S$: 264 Found: 264.

Intermediate 7 is also made by the following procedure:

Synthesis of 7-benzyloxychromane-4-one

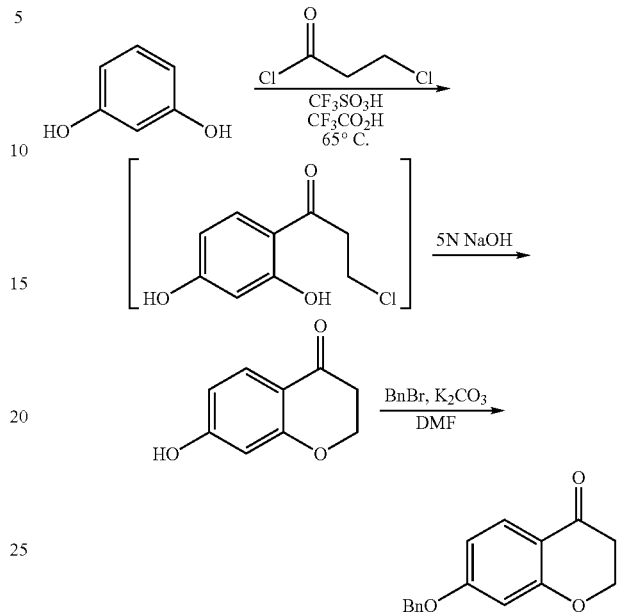

Resorcinol (50 g) was slurried in trifluoracetic acid (200 ml) at 20° C. 3-Chloropropionyl chloride (45.8 ml) was added in one portion. The mixture was stirred at 20° C. (slightly exothermic) for 1 hour to give a dark solution. Trifluoromethanesulfonic acid (56.3 ml) was heated to 67° C., and the resorcinol/3-chloropropionyl chloride/trifluoroacetic acid solution was added over 1 hour, maintaining the temperature between 67 and 69° C. The dark solution was stirred for a further 30 minutes at 68° C. HPLC indicated complete reaction.

The mixture was cooled to 10° C., and water (500 ml) was added at less than 21° C. over 30 minutes. The mixture was extracted with 2:1 toluene:MTBE (2×150 ml). The combined organic extracts were washed with 10% aqueous brine (3×150 ml) and then evaporated to approximately 100 ml. The solution was applied to a silica gel column (250 g), and the noncyclized product was eluted with 15% MTBE in toluene (approximately 900 ml). The fractions containing product (HPLC) were combined and evaporated to a deep red solution (350 Ml) which crystallized on standing.

The slurry was diluted with water (125 ml), and 5N NaOH (150 ml) was added over 20 minutes at less than 25° C. The two phase mixture was stirred at 20° C. for 1 hour. HPLC indicated complete cyclization. The layers were separated, and the organic layer was washed with water (50 ml). The aqueous layers were combined and acidified to pH 3 with slow addition of 2N HCl (200 ml) at less than 21° C. The 7-hydroxychromanone first precipitated as an oil, but at pH 7 with seeding, the oil slowly crystallized. The aqueous slurry was stirred at 20° C. for 2 hours and filtered. The solid was washed with water (2×100 ml), collected, and dried in vacuo at 40° C. overnight. 7-Hydroxychromanone was isolated as a pink solid.

The 7-hydroxychromanone was converted to the benzyloxy derivative by dissolving 49.2 g (0.3 mol) in DMF, then adding 66.7 g of benzyl bromide, and then adding 72 ml of potassium carbonate solution (0.76 g/ml, 0.42 mol) dropwise over 30 minutes to the well-stirred solution at room temperature. The temperature increased from 24° C. to 37° C. A thick slurry formed over an hour. HPLC indicated that none of the hydroxychromanone remained. The mixture was stirred for 3.5 hrs, and then 250 ml of water was added gradually. The slurry was agitated for an additional hour and then was filtered. The filter cake was washed with 2×50 ml of 1:1 DMF/water and 3×50 ml of water. After air drying to constant weight, the crude benzyl ether was obtained (purity 69 wt %). The purity was increased to 97.5 wt % by recrystallization from iPAC/heptane.

Synthesis of Ethylene Ester Intermediate

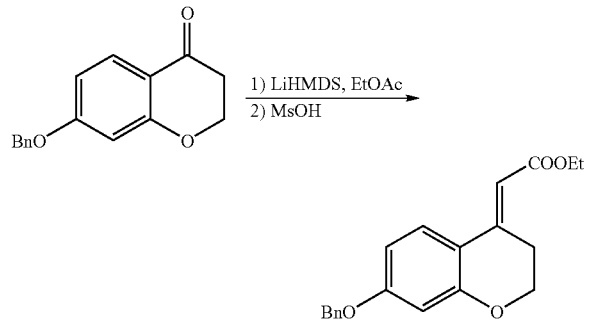

Lithium hexamethyldisilazide (LiHMDS, 130 ml of 1.0M solution) was cooled to −70° C. under nitrogen. Ethyl acetate (11.7 g) was added with stirring and cooling over 5 minutes, and the solution was stirred at −70° C. for about 65 minutes. 7-Benzyloxychromane-4-one (30.0 g) was dissolved in 150 ml THF and then was added dropwise to the reaction over a 40-minute time period at −70° C. The temperature was maintained at −70° C. for about 50 minutes, and was then allowed to increase to 0° C. LC assay shows 99% conversion. The reaction was cooled to −20° C. Methanesulfonic acid (MsOH, 8.5 mL) was added dropwise, keeping T at less than −15° C. The reaction then was allowed to warm to 0° C. Additional MsOH (16.0 mL) was added dropwise, keeping T at less than 10° C. Ethanol (5.89 g) was added in one portion, resulting in an exotherm from 6° C. to 13° C. The reaction was allowed to warm to ambient temperature. HPLC assay shows complete elimination. Water (150 ml) was then added. The layers were separated. The organic layer was washed with sat. aq. NaHCO$_3$ (60 mL), then brine (60 mL). The product was concentrated to a solid on a rotary evaporator.

The solid crude product was charged to a round bottom flask. THF (41.5 mL) was added, and the mixture was heated to 50° C. Not all of the solid dissolved. Additional THF (7.0 ml) was added, yielding a solution that was very slightly hazy. The solution was cooled to 45° C., and seed crystals from an earlier batch were added. The solution was allowed to cool slowly, resulting in a slurry. When the temperature reached 28° C., 260 mL methanol was added dropwise. After overnight aging, the slurry was cooled to 1° C. and filtered. The solid filtercake was washed with methanol (2×70 mL) and dried under vacuum/N$_2$, yielding a light yellow solid.

Hydrogenation of Ethylene Ester

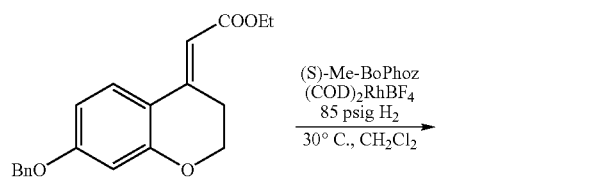

-continued

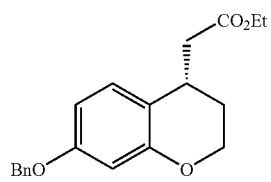

The structure of the (S)-Me-BoPhoz ligand is shown below. It is commercially available.

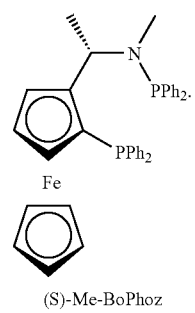

(S)-Me-BoPhoz

In a nitrogen filled glovebox, (S)-Me-BoPhoz (144.5 mg, 0.236 mmol) was combined with (COD)$_2$RhBF$_4$ (91.4 mg, 0.225 mmol) in a glass vial. CH$_2$Cl$_2$ (0.5 mL, N$_2$ degassed) was added and the slurry was stirred for 30 min. The ligand dissolved quickly. The rhodium precursor dissolved in a time that varied from seconds to ~15 min.

The ethylene ester (8.0 g crude, 92.2 wt %, 22.7 mmol) was added to an autoclave reactor in a nitrogen filled glove box, followed by addition of CH$_2$Cl$_2$ (22 mL). The catalyst solution was then transferred to the autoclave. The autoclave was assembled in the glove box, and then was removed from the glovebox and connected to a gas manifold.

The autoclave was heated to 30° C. and degassed with H$_2$ (3×85 psig). It was then charged with H$_2$ at 85 psig and stirred or agitated at 30° C. for 18 hours. The reaction was monitored by IR spectroscopy and was nearly complete after approximately 12 hours. No starting ethylene ester was observed by HPLC after 18 hours.

The reaction was then cooled to ambient temperature and vented. The reaction product was discharged from the reactor and an additional volume of CH$_2$Cl$_2$ was used to rinse the reactor (83% ee by assay).

Hydrolysis and Upgrade of ee of Chiral Acid

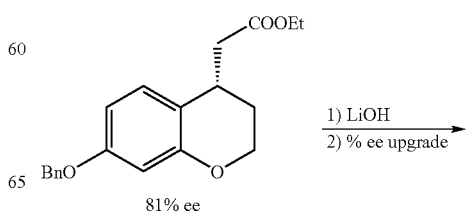

81% ee

-continued

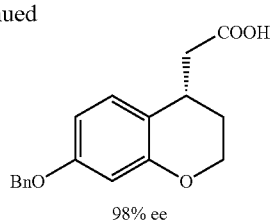

98% ee

The crude hydrogenation solution (including rinses) is converted to chiral acid having higher ee by the following procedure: The methylene chloride solution from a different hydrogenation batch than that described above (120 ml of solution containing 20 g of hydrogenated ester) was applied to a dry column of silica gel (56 g). Additional methylene chloride (450 ml) was eluted through the column until all of the ester eluted. The methylene chloride solution was evaporated to a volume of 50 ml and diluted with methanol (75 ml), THF (75 ml), and water (75 ml) at room temperature. Solid lithium hydroxide hydrate (5.14 g) was added in one portion, and the mixture was stirred at 20-23° C. for 2.5 hours until hydrolysis was complete by HPLC assay. The mixture was evaporated under reduced pressure to 80 ml and diluted with water (160 ml). The aqueous solution was washed with MME (60 ml), acidified to pH 1 with 6N HCl (24 ml) at below 25° C., and extracted with IPAc (200 ml). The IPAc solution was azeotropically dried (KF=150 μg/ml) by the addition of more IPAc (250 ml) and distilling at atmospheric pressure to a volume of 200 ml. The solution was diluted with IPAc (200 ml). HPLC assay indicated the reduced acid was present at 81% ee.

The IPAc solution was heated to reflux temperature (87° C.) and S-(−)-α-methylbenzylamine (2.30 g) added. The mixture was seeded with product (98% ee) obtained from earlier batches and stirred at reflux temperature for 20 minutes. The product started to crystallize. The remaining S-(−)-α-methylbenzylamine (3.71 g) was added over 1 hour at reflux temperature, and the mixture was heated at this temperature for a further 1 hour. The mixture was cooled to 20° C. over 1 hour and stirred at 20° C. for another hour before filtering. The solid was washed with IPAc (50 ml), collected and dried in vacuo at 40° C. overnight. The reduced acid α-MBA salt was isolated as a white crystalline solid (97.0% ee, LCWP 99.7%). It is converted to the carboxylic acid by acidification as follows. Note that the procedure described below is from a different batch and was run on a different scale.

The chiral amine salt (100 g) was charged to a flask under nitrogen, followed by 500 ml of water and 500 ml of MTBE. To the slurry was charged 6N HCl (79.5 ml). The mixture was aged for 1 h at ambient temperature until all the salts dissolved. The layers were separated and the organic layer was washed with saturated brine (1×250 ml). The organic layer was transferred to a 1 L 3-neck flask equipped with thermocouple, jacketed short path distillation head with a thermometer, and a collection flask. The batch was concentrated to ~425 ml, and then 400 ml MTBE (4 vols relative to the amine salt) was added during constant volume (425 ml) distillation (using an oil bath at ~65-70° C. at ambient pressure). The MTBE was then switched to THF by adding 400 ml (4 vols relative to the amine salt) during constant volume (425 ml) distillation. The Kf at the end of the distillation was ~3 mole % $H_2O$ (relative to the free acid), and the MMBE:TBF ratio (by $^1$H NMR) was 1:5. The solution of the free acid in a 1:5 mixture of MTBE:THF was then used in the bromination step.

Conversion of Chiral Acid to Thiazolidinedione Product

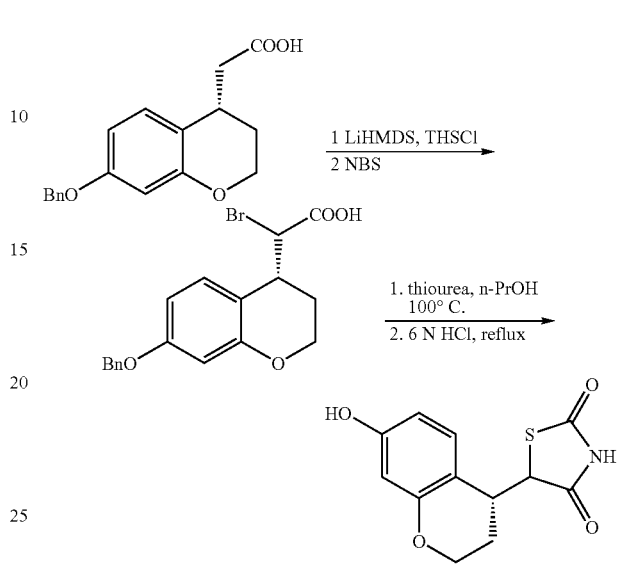

Bromination Reaction

To a 2 L 4-neck round bottom flask equipped with overhead stirrer, thermocouple, and addition funnel under nitrogen was charged 620 ml of LiHMDS (1.0 M THF solution). The solution was cooled to −50° C. (using an acetone/dry ice bath), and a solution of the free acid in THF:MTBE (above) was charged slowly via addition funnel, maintaining the batch temperature at <−40° C. After 1 h at −50° C., TMSCl was added slowly via addition funnel, maintaining the batch temperature at <40° C. The reaction was judged complete after 1 h at −50° C., based on the $^1$H NMR spectrum (in $CD_2Cl_2$). The reaction mixture was then warmed to −20° C. and solid NBS (1.0 eq, 42.42 g) was added in four equal portions (in 15 min intervals). After 1 h at −20° C., an additional 0.2 eq of NBS (8.47 g) was added in one portion. The total amount of NBS was 1.2 eq. The reaction was judged complete after aging an additional 1 h at −20° C. (when the level of the starting acid reached <1% by HPLC). The reaction mixture was then slowly transferred to a cold (−5-0° C.) mixture of 1N $NaHSO_3$ (238 ml), MTBE (356 ml), and a 1:1 mixture of water/85% $H_3PO_4$ (142 ml), while maintaining the batch temperature at <10° C. The solution (pH=2.84) was warmed to ambient temperature, the layers were separated, and the aqueous layer was back extracted with additional MTBE (1×140 ml). The combined organic layer is used in the cyclization step without isolation/purification. (The next step described below is from a different run and is on a different scale, using a similar solution to that obtained above).

Cyclization Reaction

Based on the assay amount of bromo-acid from the previous step (6.0 g, 16 mmol), a reaction flask is charged with 3 eq. of thiourea (3.65 g) and n-PrOH (30 mL, 5 ml/g of bromo-acid). The resulting slurry is heated to 70-90° C. Then the organic layer from the previous step is added. The resulting mixture is concentrated by distillation at atmospheric pressure until the bp of the reaction mixture is about 97° C. (the bp of n-PrOH) and the volume is about 30 ml (about 5 ml/g of starting bromo-acid). More thiourea (3.65 g) is added, along with 30 ml of 6 N HCl. The resulting solution is then refluxed until the reaction is complete (12-24 hours, depending on concentration). The reaction solution is cooled to room temperature, water (60 mL) and MTBE (30 mL) are added, and the phases are separated. Then the organic layer is washed twice with 60 mL of water. The aqueous layers are back extracted with the same MTBE (15 mL). The combined organic layers are concentrated, and the product is crystallized from IPA (4 ml) and toluene (16 mL) by slowly adding heptane (60 mL total).

Intermediate 8

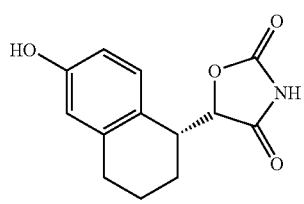

Step A

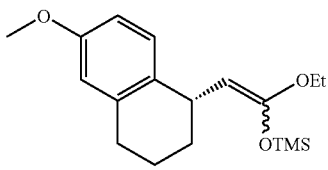

To a cooled (−78° C.) solution of ethyl [(S)-6-methoxy-1,2,3,4-tetrahydronaphthalen-1-yl]acetate (2.48 g, 10 mmol) in 20 mL of anhydrous THF was added a solution of sodium bis(trimethylsilyl)amide (1.0 M, 12 mL, 12 mmol) dropwise. The mixture was stirred at −78° C. for 30 min, then a neat solution of trimethylsilyl chloride (1.4 mL, 11 mmol) was added dropwise. The reaction was stirred for an additional 30 min., then the reaction vessel was gradually warmed to room temperature. Solvent was then removed in vacuo (roto-evaporation) and then ca. 75 mL of pentane was added to the residue. Rapid filtration and removal of solvent in vacuo yielded crude alkyl trimethyl ketene acetal.

Step B

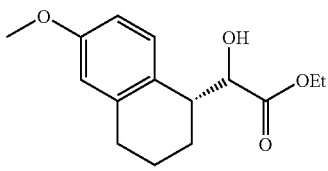

A pre-cooled (ice-methanol) stirred solution of 2.35 g (77% purity, 10 mmol) of MCPBA in 100 mL of dry hexane under an atmosphere of nitrogen was treated with a solution containing 10 mmol of the above acetal in 100 mL of dry hexane. After addition was complete (ca. 5 min), the resulting slurry was stirred for 30 min at room temperature. The reaction mixture was then treated with 1.2 g (10 mmol) of triethylammonium fluoride with stirring, which continued for 30 min after addition was completed. The mixture was then filtered, and the filtrate was diluted with 100 mL of ethyl acetate. The solution was then washed sequentially with 200 mL of 5% aqueous hydrochloric acid and 2×200 mL of 5% aqueous sodium carbonate. The organic layer was then dried using anhydrous sodium sulfate. Filtration and solvent removal in vacuo gave crude hydroxyl ester. The pure compound (1.1 g) was then obtained on Combi-Flash (5-10% ethyl acetate/hexane). LC-MS for $C_{15}H_{20}O_4$ [M+H$^+$]: calculated 264, found 265.

Step C

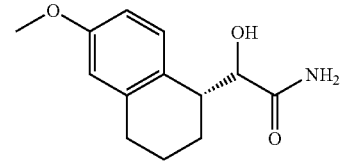

The hydroxyl ester (1.1 g, 4 mmol) obtained from Step B was mixed with 4N ammonia-methanol (50 mL) overnight, evaporated and the residue was mixed with 5 mL of ethyl acetate and 20 mL of hexane. The resulting white powder was filtered and washed with hexane, dried in high vacuo to give the pure product as single isomer (0.54 g). LC-MS for $C_{13}H_{17}NO_3$ [M+H$^+$]: calculated 235, found 236.

Step D

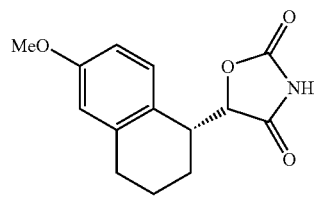

The hydroxy amide (540 mg, 2.3 mmol) and diethyl carbonate (2.72 g, 23 mmol) were mixed with sodium methoxide in methanol (0.5 M, 30 mL). The mixture was refluxed for 1.5 h, evaporated. The residue was acidified with 3N aq. HCl, extracted with ethyl acetate, dried over sodium sulfate, evaporated and purified on Comb-Flash (5-30% ethyl acetate/hexane) to give the product (470 mg). LC-MS calc. for $C_{14}H_{15}NO_4$: 261; Found: 262 (M+H).

Step E

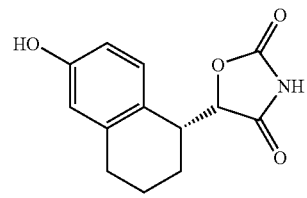

To a stirred, cool (−78° C.) solution of the product from the above step D (470 mg, 1.8 mmol) in 5 mL of dichloromethane was added a solution of boron tribromide in dichloromethane (1.0 M, 3.0 mL, 3.0 mmol). The reaction was warmed to RT for 50 min., then quenched with ice-water. The product was extracted with ethyl acetate twice. The organic phase was washed with water twice, dried with anhydrous sodium sulfate, and evaporated. The residue was dried under high vacuum to afford a light brown solid which could be used in next step without further purification. LC-MS: calc. for C13H13NO4: 247 Found: 248 (M+H).

Intermediate 9

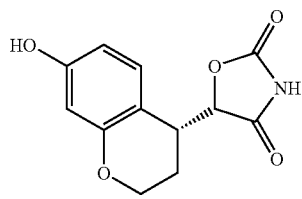

Step A

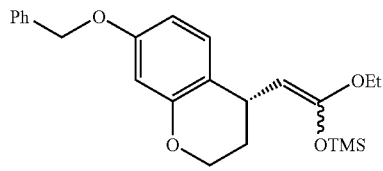

To a cooled (−78° C.) solution of ethyl [(4S)-7-(benzyloxy)-3,4-dihydro-2H-chromen-4-yl]acetate (1.0 g, 3 mmol), in 10 mL of anhydrous THF was added a solution of sodium bis(trimethylsilyl)amide (1.0 M, 3.6 mL, 3.6 mmol) dropwise. The mixture was stirred at −78° C. for 30 min, then a solution of trimethylsilyl chloride in THF (3.3 mL, 3.3 mmol) was added dropwise. The reaction was stirred for an additional 30 min., then the reaction vessel was gradually warmed to room temperature. Solvent was then removed in vacuo (roto-evaporation) and then ca. 25 mL of pentane was added to the residue. Rapid filtration and removal of solvent in vacuo yielded crude alkyl trimethyl ketene acetal.

Step B

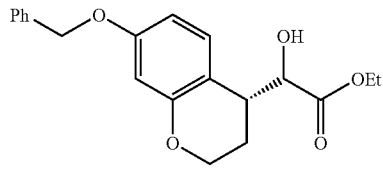

A pre-cooled (ice-methanol) stirred solution of 740 mg (77% purity, 3.3 mmol) of MCPBA in 25 mL of dry hexane under an atmosphere of nitrogen was treated with a solution containing 3 mmol of the above acetal in 25 mL of dry hexane. After addition was complete (ca. 5 min), the resulting slurry was stirred for 30 min at room temperature. The mixture was then filtered, and the filtrate was diluted with 100 mL of ethyl acetate. The solution was then washed sequentially with 200 mL of 5% aqueous hydrochloric acid and 2×200 mL of 5% aqueous sodium carbonate. The organic layer was then dried using anhydrous sodium sulfate. Filtration and solvent removal in vacuo gave crude hydroxyl ester. The pure compound (300 mg) was then obtained on Combi-Flash (5-10% ethyl acetate/hexane). LC-MS for C20H22O5 [M+H+]: calculated 342, found 343.

Step C

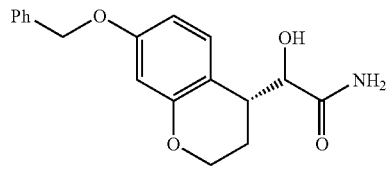

The hydroxyl ester obtained from Step B was mixed with 4N ammonia-methanol (50 mL) in a seal tube and heated at 60 C for 3 days, evaporated and the residue was mixed with 5 mL of ethyl acetate and 20 mL of hexane. The resulting white powder was filtered and washed with hexane, dried in high vacuo to give the pure product as single isomer. LC-MS for C18H19NO4 [M+H+]: calculated 313, found 314.

Step D

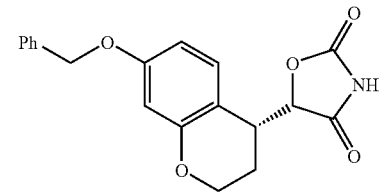

The hydroxy amide (280 mg, 0.9 mmol) and diethyl carbonate (1 mL) were mixed with sodium methoxide in methanol (15 mL, 7.5 mmol). The mixture was refluxed for 1.5 h, evaporated. The residue was acidified with 3N aq. HCl, extracted with ethyl acetate, dried over sodium sulfate, evaporated and purified on Comb-Flash (5-30% ethyl acetate/hexane) to give the product. LC-MS calc. for C19H17NO5: 339; Found: 340 (M+H).

Step E

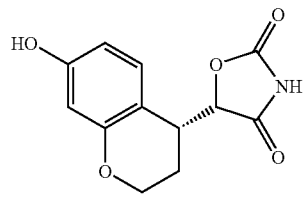

The product from the above step D (210 mg) was mixed with 20 mL of methanol and 20 mg of Pd/C (10%) and then hydrogenated on a Parr shaker under 20 lbs Hydrogen for 2 h. The catalyst was removed by filtration and the filtrates were evaporated, dried under high vacuum to give a white gummy (110 mg). LC-MS: calc. for C12H11NO5: 249 Found: 250 (M+H).

Example 1

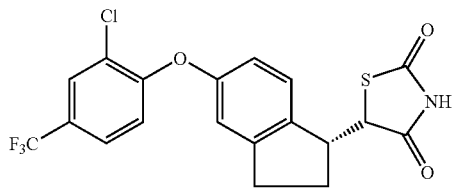

INTERMEDIATE 1 (500 mg, 2 mmol) was combined with commercially available 3-chloro-4-fluorobenzotrifluoride (440 mg, 2.2 mmol) and Cs$_2$CO$_3$ (2.0 g, 6 mmol) in 10 mL of N,N-dimethylacetamide. The reaction mixture was stirred at 120° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) yielded the product. 1H NMR (400 MHz, CDCl$_3$) δ 8.37, 8.31 (bs, bs, ratio=1:3, 1H), 7.69 (d, J=2.2 Hz, 1H), 7.41 (d, J=9.6 Hz, 1H), 7.11 (d, J=9.5, 1H), 6.98-6.70 (m, 3H), 4.90, 4.60 (dd, J=3.8, 4.60 Hz, ratio=1:3, 1H), 4.02-4.20 (m, 1H), 2.80-3.05 (m, 2H), 2.50, 2.30, 1.98 (mmm, 2H), LC-MS calc. for C19H13ClF3NO3S: 427; Found: 428 (M+H).

Example 2

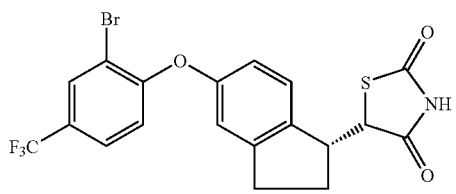

INTERMEDIATE 1 (250 mg, 11.0 mmol) was combined with 3-bromo-4-fluorobenzotrifluoride (255 mg, 1.05 mmol) and Cs$_2$CO$_3$ (1.0 g, 3 mmol) in 5 mL of N,N-dimethylacetamide. The reaction mixture was stirred at 120° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H13BrF3NO3S: 470; Found: 471 (M+H).

Example 3

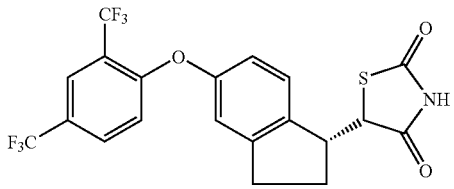

INTERMEDIATE 1 (125 mg, 0.5 mmol) was combined with 3-trifluoromethyl-4-fluorobenzotrifluoride (140 mg, 0.6 mmol) and Cs$_2$CO$_3$ (1.0 g, 3 mmol) in 5 mL of N,N-dimethylacetamide. The reaction mixture was stirred at 120° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C20H13F6NO3S: 461; Found: 462 (M+H).

Example 4

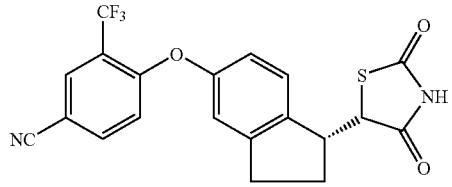

INTERMEDIATE 1 (755 mg, 0.3 mmol) was combined with 2-trifluoromethyl-4-fluorobenzonitrile (72 mg, 0.3 mmol) and Cs$_2$CO$_3$ (1.0 g, 3 mmol) in 5 mL of N,N-dimethylacetamide. The reaction mixture was stirred at 90° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C20H13F3N2O3S: 418; Found: 419 (M+H).

Example 5

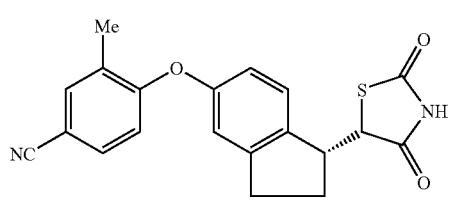

INTERMEDIATE 1 (200 mg, 0.80 mmol) was combined with 3-methyl-4-bromobenzonitrile (160 mg, 0.55 mmol) and Cs$_2$CO$_3$ (1.65 g, 5 mmol) in 5 mL of N,N-dimethylacetamide. The reaction mixture was stirred at 150° C. for 5 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C20H16N2O3S: 364; Found: 365 (M+H).

Example 6

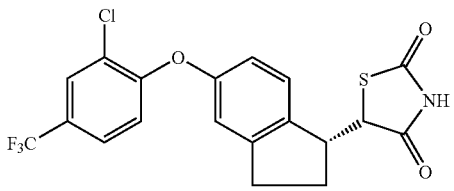

INTERMEDIATE 1 (125 mg, 0.50 mmol) was combined with 3-chloro-4-fluorobenzonitrile (102 mg, 0.6 mmol) and Cs$_2$CO$_3$ (1.65 g, 5 mmol) in 5 mL of N,N-dimethylacetamide. The reaction mixture was stirred at 130° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H13ClN2O3S: 384; Found: 385 (M+H).

Example 7

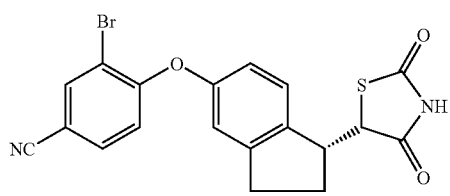

INTERMEDIATE 1 (125 mg, 0.50 mmol) was combined with 3-bromo-4-fluorobenzonitrile (100 mg, 0.5 mmol) and Cs$_2$CO$_3$ (1.65 g, 5 mmol) in 5 mL of N,N-dimethylacetamide. The reaction mixture was stirred at 90° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H13BrN2O3S: 427; Found: 428 (M+H).

Example 9

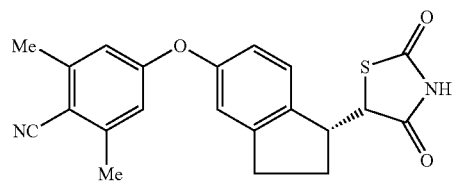

INTERMEDIATE 1 (125 mg, 0.50 mmol) was combined with 2,6-dimethyl-4-fluorobenzonitrile (75 mg, 0.5 mmol) and Cs$_2$CO$_3$ (1.6 g, 3 mmol) in 5 mL of N,N-dimethylacetamide. The reaction mixture was stirred at 150° C. for 1 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C21H18N2O3S: 378; Found: 379 (M+H).

Example 10

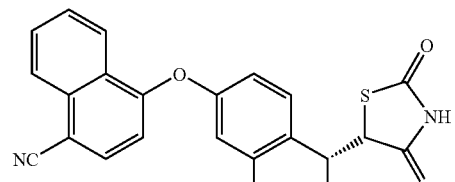

INTERMEDIATE 1 (125 mg, 0.50 mmol) was combined with 4-fluoronaphthonitrile (76 mg, 0.5 mmol) and Cs$_2$CO$_3$ (1.0 g, 3 mmol) in 5 mL of N,N-dimethylacetamide. The reaction mixture was stirred at 150° C. for 1 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C23H16N2O3S: 400; Found: 401 (M+H).

Example 11

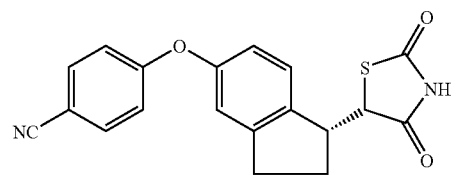

INTERMEDIATE 1 (50 mg, 0.20 mmol) was combined with 4-fluorobenzonitrile (24 mg, 0.2 mmol) and Cs$_2$CO$_3$ (650 g, 2 mmol) in 2 mL of N,N-dimethylacetamide. The reaction mixture was stirred at 120° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H14N2O3S: 350; Found: 351 (M+H).

Example 12

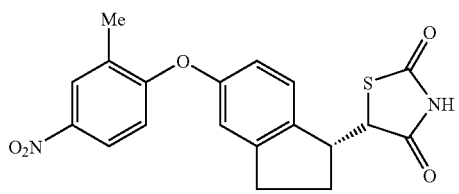

INTERMEDIATE 1 (125 mg, 0.50 mmol) was combined with 3-methyl-4-fluoronitrobenzene (79 mg, 0.2, mmol) and Cs$_2$CO$_3$ (1.0 g, 3 mmol) in 2 mL of N,N-dimethylacetamide. The reaction mixture was stirred at 90° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H16N2O5S: 384; Found: 385 (M+H).

Example 13

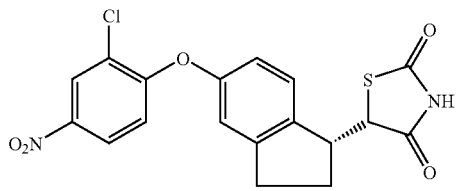

INTERMEDIATE 1 (125 mg, 0.50 mmol) was combined with 3,4-dichloro-fnitrobenzene (100 mg, 0.2 mmol) and Cs$_2$CO$_3$ (1.0 g, 3 mmol) in 2 mL of N,N-dimethylacetamide. The reaction mixture was stirred at 90° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C18H13ClN2O5S: 404; Found: 405 (M+H).

Example 14

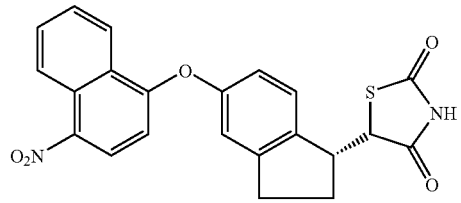

INTERMEDIATE 1 (125 mg, 0.50 mmol) was combined with 4-fluoronitronaphthalene (95 mg, 0.5 mmol) and Cs$_2$CO$_3$ (1.0 g, 3 mmol) in 5 mL of N,N-dimethylacetamide. The reaction mixture was stirred at 90° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C22H16N2O5S: 420; Found: 421 (M+H).

Example 15

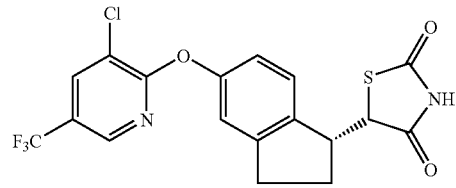

INTERMEDIATE 1 (250 mg, 1.0 mmol) was combined with 2,3-dichloro-4-trifluoromethylpyridine (216 mg, 1.0 mmol) and Cs$_2$CO$_3$ (1.4 g, 4 mmol) in 5 mL of N,N-dimethylacetamide. The reaction mixture was stirred at 120° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C18H12ClF3N2O3S: 428; Found: 429 (M+H).

Example 16

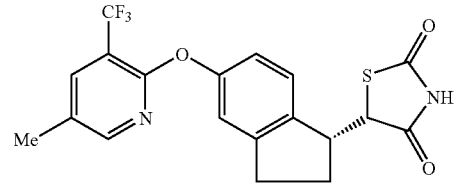

INTERMEDIATE 1 (125 mg, 0.5 mmol) was combined with 2-chloro-4-trifluoromethyl 6 methylpyridine (110 mg, 0.6 mmol) and Cs$_2$CO$_3$ (1.0 g, 3 mmol) in 5 mL of N,N-dimethylacetamide. The reaction mixture was stirred at 120° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H15F3N2O3S: 408; Found: 409 (M+H).

Example 17

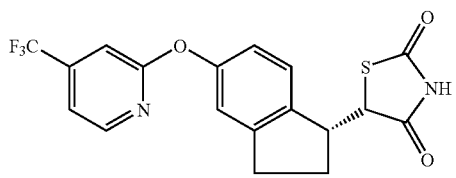

INTERMEDIATE 1 (125 mg, 0.5 mmol) was combined with 2-chloro-3-trifluoromethylpyridine (110 mg, 0.6 mmol) and Cs$_2$CO$_3$ (1.0 g, 3 mmol) in 5 mL of N,N-dimethylacetamide. The reaction mixture was stirred at 120° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C18H13F3N2O3S: 394; Found: 395 (M+H).

Example 18

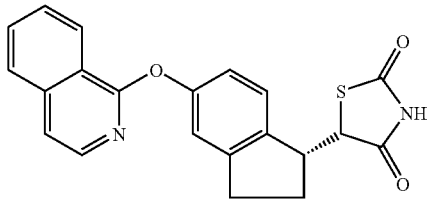

INTERMEDIATE 1 (125 mg, 0.5 mmol) was combined with 1-chloro-isoquinoline (100 mg, 0.6 mmol) and Cs$_2$CO$_3$ (1.0 g, 3 mmol) in 5 mL of N,N-dimethylacetamide. The reaction mixture was stirred at 125° C. for 1.5 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C21H16N2O3S: 376; Found: 377 (M+H).

Example 19

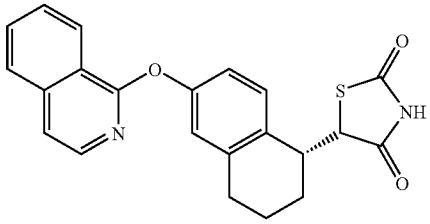

INTERMEDIATE 2 (263 mg, 1.0 mmol) was combined with 1-chloro-isoquinoline (180 mg, 1.1 mmol) and Cs$_2$CO$_3$ (1.0 g, 3 mmol) in 5 mL of N,N-dimethylacetamide. The reaction mixture was stirred at 125° C. for 1.5 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C22H18N2O3S: 390; Found: 391 (M+H).

Example 20

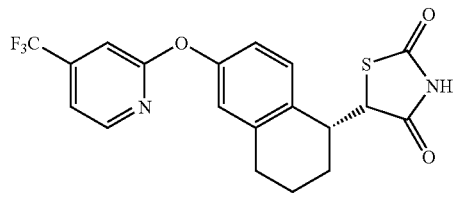

INTERMEDIATE 2 (263 mg, 1.0 mmol) was combined with 2-chloro-3-trifluoromethylpyridine (200 mg, 1.1 mmol) and Cs$_2$CO$_3$ (1.0 g, 3 mmol) in 5 mL of N,N-dimethylacetamide. The reaction mixture was stirred at 125° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H15F3N2O3S: 408; Found: 409 (M+H).

Example 21

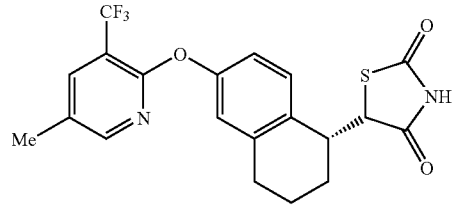

INTERMEDIATE 2 (263 mg, 1.0 mmol) was combined with 2-chloro-4-trifluoromethyl-6-methylpyridine (210 mg, 1.1 mmol) and $Cs_2CO_3$ (1.0 g, 3 mmol) in 5 mL of N,N-dimethylacetamide. The reaction mixture was stirred at 120° C. for 30 min., then was dumped into water and acidified with 2N aq. HCl to pH<2. The resulting solid precipitate was extracted with ethyl acetate and washed with water followed by brine, dried over anhydrous $Na_2SO_4$, filtered, and concentrated. Purification by Combi-Flash (silica, 5-30% ethyl acetate/hexane gradient) gave the product.

LC-MS calc. for $C20H17F3N2O3S$: 422; Found: 423 (M+H).

Example 22

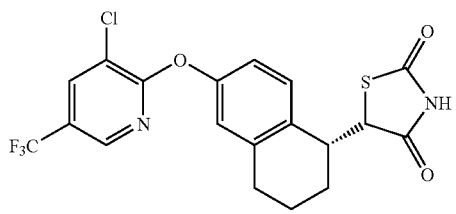

INTERMEDIATE 2 (263 mg, 1.0 mmol) was combined with 2,3-dichloro-4-trifluoromethylpyridine (238 mg, 1.11 mmol) and $Cs_2CO_3$ (1.0 g, 3 mmol) in 5 mL of N,N-dimethylacetamide. The reaction mixture was stirred at 125° C. for 30 min., then was dumped into water and acidified with 2N aq. HCl to pH<2. The resulting solid precipitate was extracted with ethyl acetate and washed with water followed by brine, dried over anhydrous $Na_2SO_4$, filtered, and concentrated. Purification by Combi-Flash (silica, 5-30% ethyl acetate/hexane gradient) gave the product.

LC-MS calc. for $C19H14ClF3N2O3S$: 442; Found: 443 (M+H).

Example 23

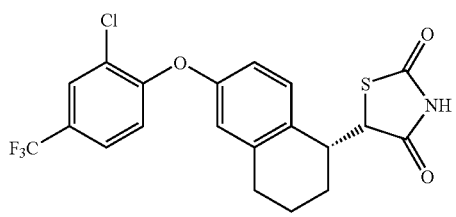

INTERMEDIATE 2 (263 mg, 1.0 mmol) was combined with 3-chloro-4-fluorobenzotrifluoride (220 mg, 1.1 mmol) and $Cs_2CO_3$ (1.0 g, 3 mmol) in 5 mL of N,N-dimethylacetamide. The reaction mixture was stirred at 125° C. for 30 min, then was dumped into water and acidified with 2N aq. HCl to pH<2. The resulting solid precipitate was extracted with ethyl acetate and washed with water followed by brine, dried over anhydrous $Na_2SO_4$, filtered, and concentrated. Purification by Combi-Flash (silica, 5-30% ethyl acetate/hexane gradient) gave the product.

LC-MS calc. for $C20H15ClF3NO3S$: 441; Found: 442 (M+H).

Example 24

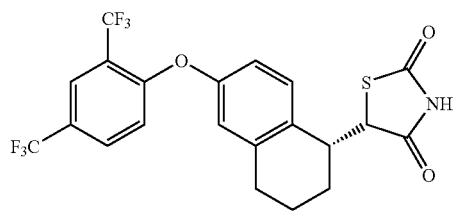

INTERMEDIATE 2 (132 mg, 0.5 mmol) was combined with 3-trifluoromethyl-4-fluorobenzotrifluoride (140 mg, 0.6 mmol) and $Cs_2CO_3$ (1.0 g, 3 mmol) in 5 mL of N,N-dimethylacetamide. The reaction mixture was stirred at 125° C. for 30 min, then was dumped into water and acidified with 2N aq. HCl to pH<2. The resulting solid precipitate was extracted with ethyl acetate and washed with water followed by brine, dried over anhydrous $Na_2SO_4$, filtered, and concentrated. Purification by Combi-Flash (silica, 5-30% ethyl acetate/hexane gradient) gave the product.

LC-MS calc. for $C21H15F6NO3S$: 475; Found: 476 (M+H).

Example 25

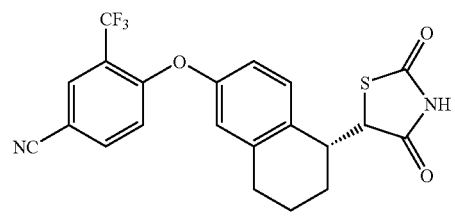

INTERMEDIATE 2 (132 mg, 0.5 mmol) was combined with 2-trifluoromethyl-4-fluorobenzonitrile (103 mg, 0.5 mmol) and $Cs_2CO_3$ (1.0 g, 3 mmol) in 5 mL of N,N-dimethylacetamide. The reaction mixture was stirred at 90° C. for 30 min, then was dumped into water and acidified with 2N aq. HCl to pH<2. The resulting solid precipitate was extracted with ethyl acetate and washed with water followed by brine, dried over anhydrous $Na_2SO_4$, filtered, and concentrated. Purification by Combi-Flash (silica, 5-30% ethyl acetate/hexane gradient) gave the product.

LC-MS calc. for $C21H15F3N2O3S$: 432; Found: 433 (M+H).

Example 26

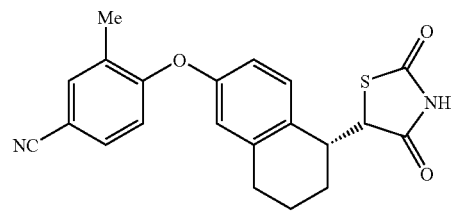

INTERMEDIATE 2 (132 mg, 0.5 mmol) was combined with 3-methyl-4-bromobenzonitrile (100 mg, 0.5 mmol) and Cs$_2$CO$_3$ (1.65 g, 5 mmol) in 5 mL of N,N-dimethylacetamide. The reaction mixture was stirred at 150° C. for 5 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C21H18N2O3S: 378; Found: 379 (M+H).

Example 27

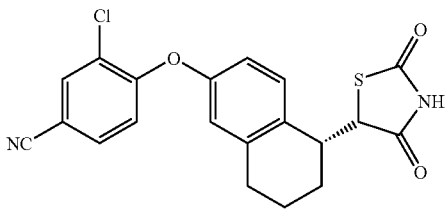

INTERMEDIATE 2 (263 mg, 1.0 mmol) was combined with 3-chloro-4-fluorobenzonitrile (178 mg, 1.1 mmol) and Cs$_2$CO$_3$ (3.26 g, 10 mmol) in 10 mL of N,N-dimethylacetamide. The reaction mixture was stirred at 130° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C20H15ClN2O3S: 398; Found: 399 (M+H).

Example 28

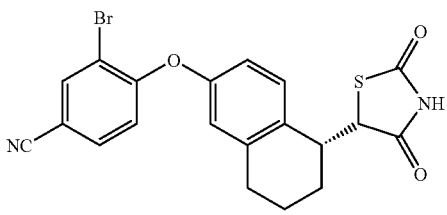

INTERMEDIATE 2 (132 mg, 0.50 mmol) was combined with 3-bromo-4-fluorobenzonitrile (100 mg, 0.5 mmol) and Cs$_2$CO$_3$ (1.65 g, 5 mmol) in 5 mL of N,N-dimethylacetamide. The reaction mixture was stirred at 90° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C20H15BrN2O3S: 442; Found: 443 (M+H).

Example 29

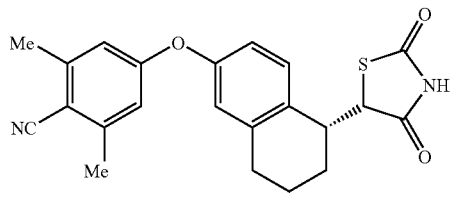

INTERMEDIATE 2 (132 mg, 0.50 mmol) was combined with 2,6-dimethyl-4-fluorobenzonitrile (75 mg, 0.5 mmol) and Cs$_2$CO$_3$ (1.0 g, 3 mmol) in 5 mL of N,N-dimethylacetamide. The reaction mixture was stirred at 150° C. for 1 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C22H20N2O3S: 392; Found: 393 (M+H).

Example 30

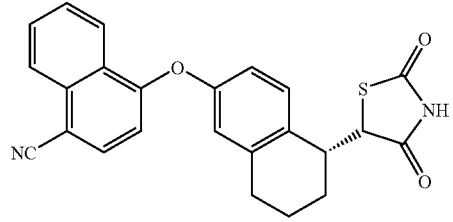

INTERMEDIATE 1 (132 mg, 0.50 mmol) was combined with 4-fluoronaphthonitrile (76 mg, 0.5 mmol) and Cs$_2$CO$_3$ (1.0 g, 3 mmol) in 5 mL of N,N-dimethylacetamide. The reaction mixture was stirred at 150° C. for 1 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C24H18N2O3S: 414; Found: 415 (M+H).

Example 31

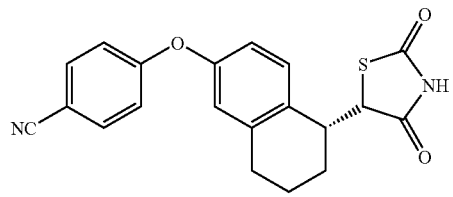

INTERMEDIATE 2 (132 mg, 0.50 mmol) was combined with 4-fluorobenzonitrile (62 mg, 0.2 mmol) and Cs$_2$CO$_3$ (1.0 g, 5 mmol) in 5 mL of N,N-dimethylacetamide. The reaction mixture was stirred at 120° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C20H14N2O3S: 350; Found: 351 (M+H).

Example 32

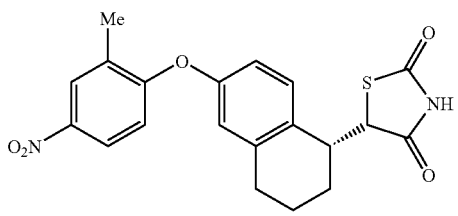

INTERMEDIATE 2 (132 mg, 0.50 mmol) was combined with 3-methyl-4-fluoronitrobenzene (78 mg, 0.2 mmol) and Cs$_2$CO$_3$ (1.0 g, 3 mmol) in 2 mL of N,N-dimethylacetamide. The reaction mixture was stirred at 125° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C20H18N2O5S: 398; Found: 399 (M+H).

Example 33

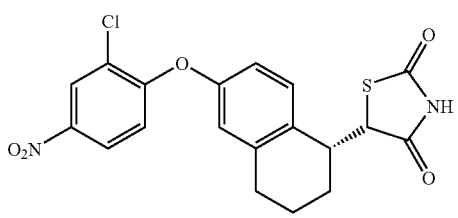

INTERMEDIATE 2 (263 mg, 1.0 mmol) was combined with 3,4-dichloro-nitrobenzene (200 mg, 1.05 mmol) and Cs$_2$CO$_3$ (1.6 g, 3 mmol) in 5 mL of N,N-dimethylacetamide. The reaction mixture was stirred at 100° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H15ClN2O5S: 418; Found: 419 (M+H).

Example 34

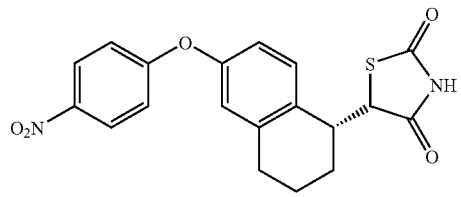

INTERMEDIATE 2 (132 mg, 0.50 mmol) was combined with 4-fluoronitrobenzene (79 mg, 0.5 mmol) and Cs$_2$CO$_3$ (1.0 g, 3 mmol) in 5 mL of N,N-dimethylacetamide. The reaction mixture was stirred at 120° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H16N2O5S: 384; Found: 385 (M+H).

Example 35

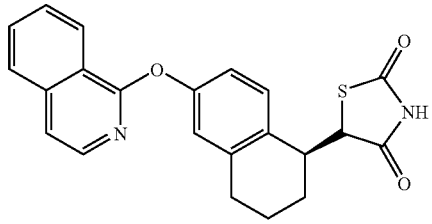

INTERMEDIATE 3 (263 mg, 1.0 mmol) was combined with 1-chloro-isoquinoline (180 mg, 1.1 mmol) and Cs$_2$CO$_3$ (1.0 g, 3 mmol) in 5 mL of N,N-dimethylacetamide. The reaction mixture was stirred at 125° C. for 1.5 h, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C22H18N2O3S: 390; Found: 391 (M+H).

Example 36

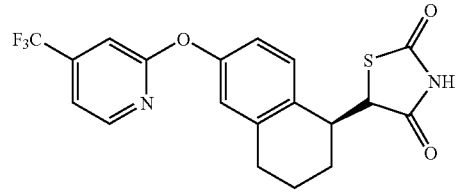

INTERMEDIATE 3 (263 mg, 1.0 mmol) was combined with 2-chloro-3-trifluoromethylpyridine (200 mg, 1.1 mmol) and Cs$_2$CO$_3$ (1.0 g, 3 mmol) in 5 mL of N,N-dimethylacetamide. The reaction mixture was stirred at 125° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H15F3N2O3S: 408; Found: 409 (M+H)

Example 36a

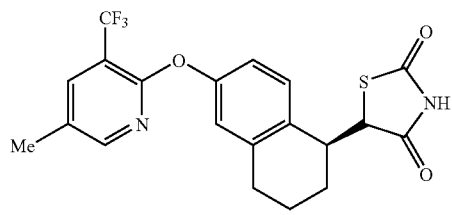

INTERMEDIATE 3 (263 mg, 1.0 mmol) was combined with 2-chloro-4-trifluoromethyl-6-methylpyridine (210 mg, 1.1 mmol) and Cs$_2$CO$_3$ (1.0 g, 3 mmol) in 5 mL of N,N-dimethylacetamide. The reaction mixture was stirred at 120° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C20H17F3N2O3S: 422; Found: 423 (M+H).

Example 37

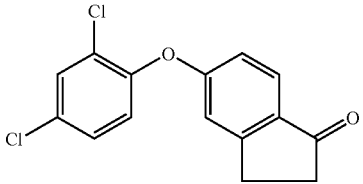

INTERMEDIATE 3 (263 mg, 1.0 mmol) was combined with 2,3-dichloro-4-trifluoromethylpyridine (240 mg, 1.1 mmol) and Cs$_2$CO$_3$ (1.0 g, 3 mmol) in 5 mL of N,N-dimethylacetamide. The reaction mixture was stirred at 125° C. for 30 min., then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 5-30% ethyl acetate/hexane gradient) gave the product.

LC-MS calc. for C19H14ClF3N2O3S: 442; Found: 443 (M+H).

Example 38

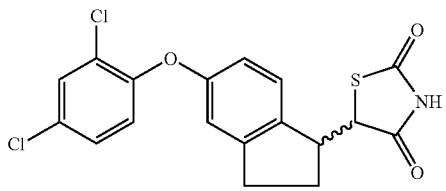

Step A

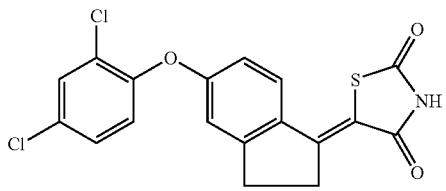

2,4-Dichlorophenol (2.45 g, 15 mmol), 5-fluoroindanone (2.0 g, 13.3 mmol) and potassium carbonate (2.76 g, 20 mmol) were mixed in 50 mL of N,N-dimethyl acetamide, stirred at 150° C. overnight, cooled at RT and diluted with water, extracted with ether. The dark ether layer was washed with 10% aq. NaOH and brine, dried over anhydrous sodium sulfate, filtered, evaporated to give the product.

LC-MS calc. for C15H10Cl2O2: 292; Found: 293 (M+H).

Step B

The ketone (0.865 g, 2.95 mmol) from Step A, Example 38, was mixed with 2,4-thiazolidinedione (433 mg, 3.7 mmol) and sodium acetate (600 mg, 7.3 mmol) in a small flask and was heated at 145° C. under nitrogen flow overnight. The reaction was quenched with water, extracted with ethyl acetate, dried over sodium sulfate, filtered and evaporated. The residue was purified on Combi-Flash (5-20% ethyl acetate/hexane) to give the product as a yellow solid.

LC-MS calc. for C18H11Cl2NO3S: 390; Found: 391 (M+H).

Step C

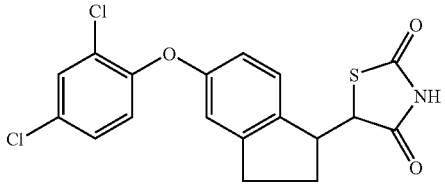

The condensed product (280 mg, 0.716 mmol) from Step B, Example 38, was mixed with pyridine (0.61 mL) and THF (0.61 mL), cooled at 0° C. To the mixture was added a solution of lithium borohydride in THF (2.0 M, 1.0 mL, 2.0 mmol). The mixture was stirred at RT for 10 min., then refluxed for 3 h, quenched with 3N aq. HCl (pH<2), extracted with ethyl acetate, dried over sodium sulfate, filtered and evaporated. The residue was purified on Combi-Flash (5-20% ethyl acetate/hexane) to give the product as a mixture of 2 diastereomers.

LC-MS calc. for C18H13Cl2NO3S: 393; Found: 394 (M+H).

Example 39

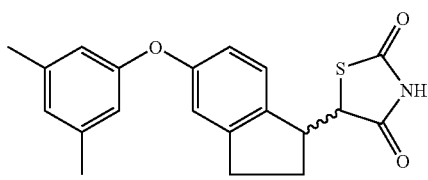

This compound was prepared as a mixture of racemic diastereomers according to the same procedures of Example 38 by replacing 2,4-dichlorophenol with 3,5-dimethylphenol.

LC-MS calc. for C20H19NO3S: 353; Found: 354 (M+H).

Example 40

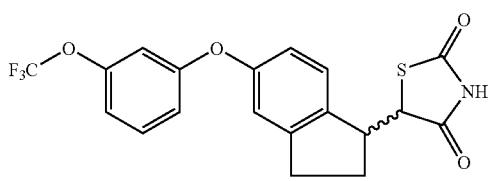

This compound was prepared as a mixture of racemic diastereomers according to the same procedures of Example 38 by replacing 2,4-dichlorophenol with 3-trifluoromethoxyphenol.

LC-MS calc. for C19H14F3NO4S: 409; Found: 410 (M+H).

Example 41

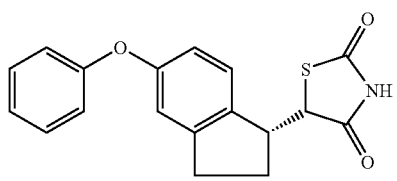

To a mixture of Intermediate 1 (50 mg, 0.2 mmol), iodobenzene (44.9 mg, 0.22 mmol), cesium carbonate (195.5 mg, 0.6 mmol), copper (I) iodide (3.8 mg, 0.02 mmol), and N,N-dimethylglycine (8.4 mg, 0.06 mmol) was added 1,4-dioxane (1 mL) and dimethylformamide (1 mL). The reaction was sealed, degassed and backfilled with $N_2$ twice, and heated to 110° C. overnight. The completed reaction was poured into 0.1 N aqueous hydrochloric acid (6 mL) and extracted with ethyl acetate (3×6 mL). The combined organic fractions were concentrated in vacuo. The residue was purified by reverse-phase HPLC (YMC-Pack Pro C18 5 micron, 40% to 100% $CH_3CN/H_2O/0.1\%$ TFA). The combined pure fractions were lyophilized overnight to obtain a white solid with an approximately 7 to 3 mixture of diastereomers R,S- and R,R-, respectively. LC-MS for $C_{18}H16NO3S$ [M+H$^+$]: calculated 326.1, found 326.2.

More examples were prepared according to the same procedure as described in the preparation of Example 41. These are shown in Table 1.

TABLE 1

| Compound | R1 | R2 | R3 | R4 | Molecular Formula | Calculated [M + H$^+$] | Found [M + H$^+$] |
|---|---|---|---|---|---|---|---|
| Example 42 | H | H | H | H | $C_{18}H_{15}NO_3S$ | 326.1 | 326.2 |
| Example 43 | H | Et | H | H | $C_{20}H_{19}NO_3S$ | 354.1 | 354.3 |
| Example 44 | Cl | H | F | H | $C_{18}H_{13}ClFNO_3S$ | 378.0 | No ion |
| Example 45 | H | Me | F | H | $C_{19}H_{16}FNO_3S$ | 358.1 | No ion |
| Example 46 | Me | H | F | H | $C_{19}H_{16}FNO_3S$ | 358.1 | 359.2 |
| Example 47 | Et | H | CN | H | $C_{21}H_{18}N_2O_3S$ | 379.1 | 379.2 |
| Example 48 | Me | H | CF3 | H | $C_{20}H_{16}F_3NO_3S$ | 408.1 | 408.2 |

Example 49-51

The Examples in Table 2 below were prepared according to the same procedure as described in the preparation of Example 1 by replacing INTERMEDIATE 1 with INTERMEDIATE 4.

TABLE 2

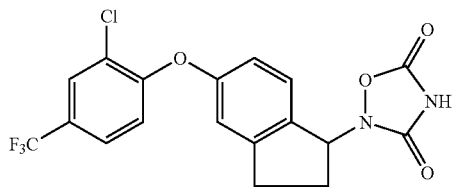

| Compound | R1 | R2 | R3 | R4 | R5 | Molecular Formula | Calculated [M + H⁺] | Found [M + H⁺] |
|---|---|---|---|---|---|---|---|---|
| Example 49 | Me | H | CN | H | H | $C_{19}H_{15}N_2O_4S$ | 367.1 | 367.0 |
| Example 50 | Cl | H | $CF_3$ | H | H | $C_{18}H_{12}ClF_3NO_4S$ | 430.0 | 430.0 |
| Example 51 | F | H | CN | H | H | $C_{18}H_{12}FN_2O_4S$ | 371.0 | 371.0 |

Example 52

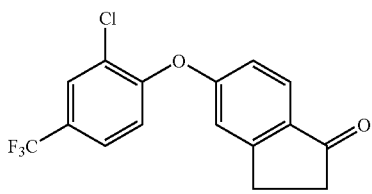

Step A

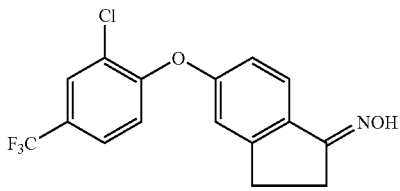

5-Hydroxyindanone (2.96 g, 20 mmol), 2-chloro-4-fluorobenzotrifluoride (4.30 g, 22 mmol) and cesium carbonate (13 g, 40 mmol) were mixed in 50 mL of N,N-dimethyl acetamide, stirred at 150° C. overnight, cooled to RT, diluted with water, and extracted with ether. The dark ether layer was washed with 10% aq. NaOH and brine, dried over anhydrous sodium sulfate, filtered, evaporated, and purified by FC (silica gel, 10% ethyl acetate) to give the product.

LC-MS. calc. for C16H10ClF3O2: 326; Found: 327 (M+H).

Step B

The ketone (3.27 g, 10 mmol) from Step A, Example 52, was mixed with hydroxylamine hydrochloride (770 mg, 11 mmol) and sodium acetate (900 mg, 11 mmol) in a flask containing 50 mL of ethanol. It was refluxed under nitrogen flow overnight. The reaction was quenched with water, extracted with ethyl acetate, dried over sodium sulfate, filtered, and evaporated. The residue was purified by FC (silica gel, 20% ethyl acetate/hexane) to give the product as a yellow solid.

LC-MS calc. for C16H13ClF3NO2: 341; Found: 342 (M+H).

Step C

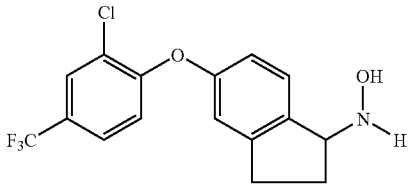

The oxime (1.5 g, 4.4 mmol) from Step B, Example 52, was mixed with sodium cyanoborohydride (380 mg, 6 mmol) in 20 mL of methanol. To this stirred mixture was slowly added a solution of 4N HCl in dioxane until the pH was 4. The resulting mixture was stirred at RT for one hour, quenched with sat. aq. sodium carbonate, extracted with ethyl acetate, antiwashed with water, dried over sodium sulfate, filtered, evaporated, and purified on Comb-Flash (ethyl acetate) to give the product as a colorless solid.

LC-MS calc. for C16H13ClF3NO2: 343; Found: 344 (M+1).

Step D

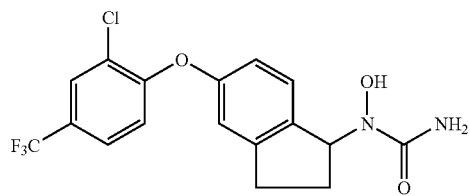

To a stirred solution of the hydroxylamine (1.02 g, 3 mmol) from Step C, Example 52, in a mixture 15 mL of anhydrous dioxane and 15 mL of anhydrous THF was added dropwise a neat solution of trimethylsilyl isocyanate (0.61 mL, 4.5 mmol). The mixture was stirred for one hour, mixed with water and extracted with ethyl acetate, dried over sodium sulfate, evaporated, and purified on Combi-Flash (80-100% ethyl acetate/hexane) to give the product as a white solid.

LC-MS calc. for C17H14ClF3N2O3: 386; Found: 387 (M+H).

Step E

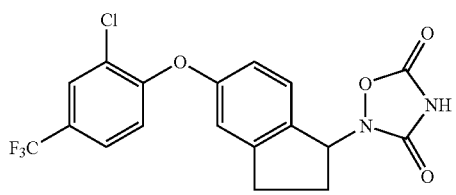

To a stirred solution of the hydroxyurea (460 g, 1.2 mmol) from Step D, Example 52, in 20 mL of anhydrous THF was added sodium hydride (60% oil, 68 mg, 1.7 mmol). The resulting mixture was stirred for one hour, treated with methyl chloroformate (189 mg, 2.0 mmol), stirred for an additional 30 min, dumped into water, extracted with ethyl acetate, dried over sodium sulfate, filtered and evaporated to afford an oily residue. The residue was dried under high vacuo, dissolved in 10 mL of anhydrous DMF, and treated with sodium hydride (60% oil, 68 mg, 1.7 mmol). After stirring for one hour, the reaction mixture was mixed with water, extracted with ethyl acetate, and purified on Combi-Flash (ethyl acetate) to give the product. LC-MS calc. for C18H12ClF3N2O4: 412; Found: No Molecular Ion (M+H).

Example 53

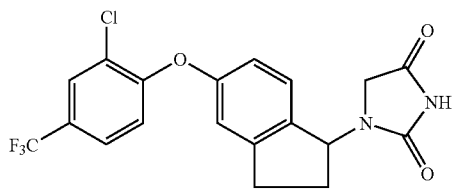

Step A

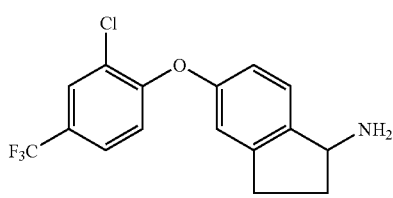

The oxime (3.42 g, 10 mmol) from Step B, Example 52, was mixed in a pressure flask with Ra—Ni (1.0 g) and 7N ammonia-methanol (50 mL). The hydrogenation was carried out on a Parr shaker under 50 psi of hydrogen overnight. The catalyst was removed by filtering through celite. The filtrates were evaporated and the residue was dried under high vacuo to afford a white solid which was used in next step without further purification. 1H NMR (400 MHz, CDCl$_3$) δ 7.82 (s, 1H), 7.51 (m, 1H), 7.40 (m, 1H), 7.02 (m, 3H), 3.80 (bs, 1H), 3.10-2.60 (m, 4H), 1.90 (bs, 2H). LC-MS calc. for C16H13ClF3NO: 377; Found: 311 (M-NH2).

Step B

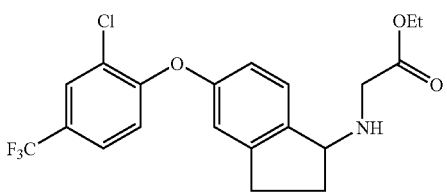

The crude amine (1.0 g, 3 mmol) from Step A, Example 53, and potassium carbonate (1.38 g, 10 mmol) were dissolved in 20 mL of N,N-dimethyl acetamide. To the mixture was added ethyl bromoacetate (0.5 mg, 3.1 mmol). The reaction was then stirred at RT for 2 h, and water was added. The organic layer was separated and washed with water, dried over sodium sulfate, filtered and evaporated, and purified on Combi-Flash (50% ethyl acetate) to give the product. 1H NMR (400 MHz, CDCl$_3$) δ 7.69 (1, 1H), 7.35 (dd, J=8.5, 7.9 Hz, 2H), 6.90 (d, J=8.6 Hz, 1H), 6.85 (s, 1H), 6.84 (d, J=8.8 Hz, 1H), 4.20 (m, 3H), 3.40 (s, 21H), 3.00 (m, 1H), 2.98 (m, 1H), 2.38 (m, 1H), 2.17 (bs, 1H), 1.90 (m, 1H), 1.26 (t, J=7.2 Hz, 3H). LC-MS calc. for C20H19ClF3NO3: 413; Found: 414 (M+H).

Step C

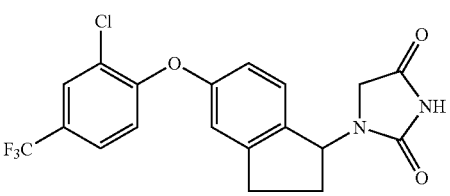

To a stirred solution of the glycinate (380 mg, 0.92 mmol) from Step B, Example 53, and diisopropyl ethylamine (129 mg, 1.0 mmol) in 5 mL of anhydrous dichloromethane was added a solution of trichloroacetyl isocyanate (188 mg, 1.0 mmol) in 1 mL of dichloromethane. The resulting mixture was evaporated and then mixed with potassium carbonate (276 mg, 2 mmol) and ethanol (20 mL). The mixture was refluxed for 2 h, acidified with 6N aq. HCl, stirred for another one hour, diluted with water, and extracted with ethyl acetate. The crude product was purified on Combi-Flash (50-80% ethyl acetate/hexane) to give the product as a white solid. 1H NMR (400 MHz, CDCl$_3$) δ 8.21 (bs, 1H), 7.71 (s, 1H), 7.41 (d, J=8.5 Hz, 1H), 7.16 (d, J=8.9 Hz, 1H), 6.96 (d, J=8.5 Hz, 1H), 6.88 (d, J=8.5 Hz, 1H), 6.87 (s, 1H), 5.74 (t, J=7.4 Hz, 1H), 3.73, 3.57 (dd, J=14.6, 17.5 Hz, 2H), 2.95 (m, 2H), 2.50 (m, 1H), 1.99 (m, 1H). LC-MS calc. for C19H14ClF3N2O3: 410; Found: 411 (M+H).

Example 54

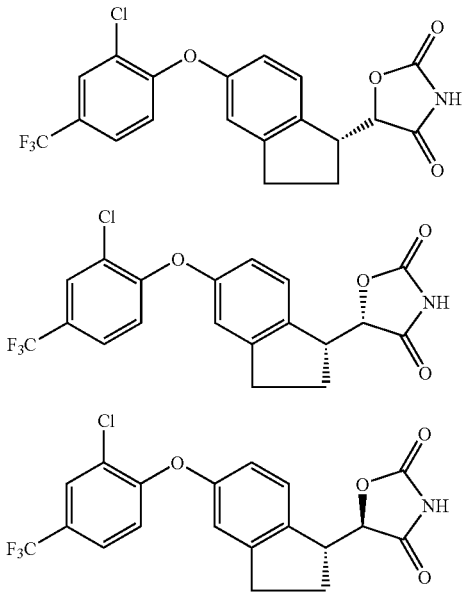

INTERMEDIATE 5 (crude, 100 mg, 0.4 mmol) was combined with 3-chloro-4-fluorobenzotrifluoride (75 mg, 0.37 mmol) and Cs$_2$CO$_3$ (1.0 g, 3 mmol) in 5 mL of N,N-dimethylacetamide. The reaction mixture was stirred at 90° C. for 60 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 30-50% ethyl acetate/hexane gradient) gave the product. LC-MS calc. for C19H13ClF3NO4: 411; Found: 412 (M+H). 1H NMR (400 MHz, CDCl$_3$) (major isomer) δ 8.18 (bs, 1H), 7.89 (s, 1H), 7.60 (d, J=8.2 Hz, 1H), 7.47 (d, J=7.8 Hz, 1H), 7.14 (d, J=8.6 Hz, 1H), 7.04 (m, 2H), 5.36 (d, J=2.7 Hz, 1H), 4.02 (m, 1H), 3.22 (m, 1H), 3.05 (m, 1H), 2.45 (m, 2H), 2.24 (m, 1H). The two diasteromers of Example 54 were separated into single enantiomers (54a and 54b) on Chiracel AD or OD column.

Example 55

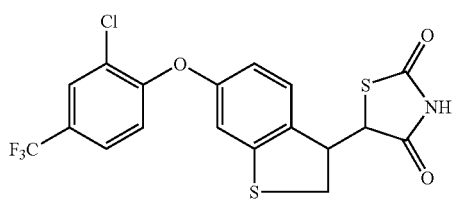

INTERMEDIATE 6 (134 mg, 0.5 mmol) was combined with 3-chloro-4-fluorobenzotrifluoride (10 mg, 0.5 mmol) and Cs$_2$CO$_3$ (1.0 g, 3 mmol) in 5 mL of N,N-dimethylacetamide. The reaction mixture was stirred at 120° C. for 30 min, then was dumped into water and acidified with 2N aq. HCl to pH<2. The resulting solid precipitate was extracted with ethyl acetate and washed with water followed by brine, dried over anhydrous Na$_2$SO$_4$, filtered, and concentrated. Purification by Combi-Flash (silica, 30-50% ethyl acetate/hexane gradient) gave the product.

LC-MS calc. for C18H11ClF3NO3S2: 444; Found: 445 (N+H).

Example 56

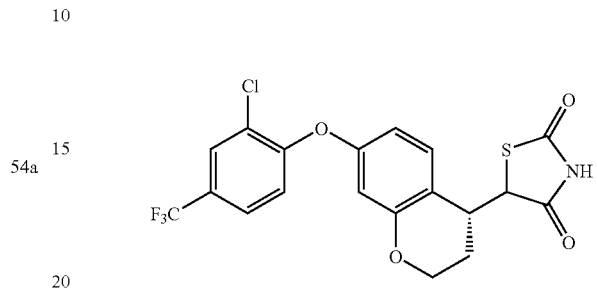

To a mixture of Intermediate 7 (97 mg, 0.366 mmol) and Cs$_2$CO$_3$ (298 mg, 0.915 mmol) was added DMF (2 mL) followed by commercially available 3-chloro-4-fluoro-benzotrifluoride (95 mg, 0.48 mmol). The reaction was heated at 110° C. for 2 hours and then quenched with 0.1 N HCl (15 mL). The mixture was extracted with EtOAc (3×15 mL). The organic layers were combined and washed with Brine (1×10 mL), dried over anhydrous Na$_2$SO$_4$ and concentrated in vacuo. The residue was purified by silica gel chromatography (0% to 45% EtOAc/hexanes) to give white solid as a mixture of diastereomers. R$_f$=0.15 (30% EtOAc/hexanes); LC-MS calc. for C$_{19}$H$_{13}$ClF$_3$NO$_4$S: 443.02 Found (ES−): 442.0 [M−H]; $^1$H NMR (500 MHz, CDCl$_3$) δ 8.60 (s, 1H), 8.54 (s, 0.4H), 7.75 (d, J=1.8 Hz, 1.4H), 7.51-7.47 (m, 1.4H), 7.10-7.02 (m, 2.8H), 6.63-6.60 (m, 1H), 6.57-6.54 (m, 0.4H), 6.50 (d, J=2.6 Hz, 1.4H), 5.11 (d, J=4.1 Hz, 1H), 4.60 (d, J=4.6 Hz, 0.4H), 4.45-4.41 (m, 1H), 4.29-4.10 (m, 1.8H), 3.98-3.94 (m, 1H), 3.84-3.81 (m, 0.4H), 2.36-2.30 (0.4H), 2.24-1.90 (m, 2.4H).

This reaction has been run on a larger scale as follows: A 50 L three-necked round bottom flask was charged with Intermediate 7 (3.00 kg), commercial 3-chloro-4-fluorobenzotrifluoride (2.47 kg), Cs$_2$CO$_3$ (11.1 kg), and DMSO (12 L). The slurry was warmed to 110° C. and aged until reaction was complete, with <1% (assay %) of Intermediate 7 remaining after 6-8 h. The slurry was cooled to ambient temperature, and water (12 L) and EtOAc (20 L) were added. The organic layer was washed with 5N HCl (5 L). The pH of the aqueous layer was 1-2. Then the organic layer was washed with 5% NaHCO$_3$ (10 L). The organic layer was then treated with Darco KB (20 wt %, 800 g), aged at rt for 2 h, filtered through solka floc, and rinsed with EtOAc (8 L).

The product was then epimerized at the thiazoldinedione center and crystallized. The filtrate was first solvent switched to NPA (n-propyl alcohol), and the amount of NPA was adjusted to 20 L. The solution was warmed to 70° C., water was added (30 L), and then seed crystals from earlier batches were added. Additional water (30 L) was added over 1 h while the temperature was maintained at 70° C. The solution was aged at 70° C. for 2-3 h, and then was cooled to rt over 2-3 h. The crystals were then filtered, washed with 1:3 NPA/H$_2$O (16 L), and dried over N2. The crude filtercake was dissolved in toluene (15 L) at 60° C. Heptane (30 L) was added over 1 h, and the solution was allowed to cool to rt over 1 h. The resulting crystals were filtered, washed with 1:2 toluene/heptane (11 L), and dried over N$_2$.

Examples 57-71

Compounds with variations on the left side of the structure were prepared using the reaction scheme detailed in Example 56, replacing 3-chloro-4-fluoro-benzotrifluoride with corresponding aryl fluorides or aryl chlorides. All of the reactants and starting materials are either commercially available or are described in the Intermediates section or are readily prepared by a practitioner in the field of synthetic organic chemistry. These compounds are summarized in the table below.

| Example | Compound | Molecular Formula | Calculated [M] | Observed (ES+) |
|---|---|---|---|---|
| 57 | | $C_{18}H_{13}Cl_2NO_4S$ | 410.279 | 411.0 (ES+) |
| 58 | | $C_{23}H_{16}N_2O_4S$ | 416.08 | 417.0 (ES+) |
| 59 | | $C_{20}H_{17}NO_6S$ | 399.08 | 400.0 (ES+) |
| 60 | | $C_{20}H_{16}N_2O_4S$ | 380.08 | 381 (ES+) |
| 61 | | $C_{19}H_{13}ClN_2O_4S$ | 400.03 | 401 (ES+) |
| 62 | | $C_{20}H_{15}ClF_3NO_4S$ | 457.04 | 458 (ES+) |

| Example | Compound | Molecular Formula | Calculated [M] | Observed (ES+) |
|---|---|---|---|---|
| 63 | (structure: 2-(1-hydroxyethyl)-4-trifluoromethylphenoxy chromanyl thiazolidinedione) | $C_{21}H_{18}F_3NO_5S$ | 453.09 | 452.2 (ES−) |
| 64 | (structure: 2-ethyl-4-trifluoromethylphenoxy chromanyl thiazolidinedione) | $C_{21}H_{18}F_3NO_4S$ | 437.09 | 436.1 (ES−) |
| 65 | (structure: 2-methyl-4-chloro-5-trifluoromethylphenoxy chromanyl thiazolidinedione) | $C_{20}H_{15}ClF_3NO_4S$ | 457.04 | 458 (ES+) |
| 66 | (structure: 2-chlorophenoxy chromanyl thiazolidinedione) | $C_{18}H_{14}ClNO_4S$ | 375.03 | 376 (ES+) |
| 67 | (structure: 2-formyl-4-trifluoromethylphenoxy chromanyl thiazolidinedione) | $C_{20}H_{14}F_3NO_5S$ | 437.05 | 436.1 (ES−) |
| 68 | (structure: 2-hydroxymethyl-4-trifluoromethylphenoxy chromanyl thiazolidinedione) | $C_{20}H_{16}F_3NO_5S$ | 439.07 | 438.2 (ES−) |
| 69 | (structure: 2-carboxy-4-trifluoromethylphenoxy chromanyl thiazolidinedione) | $C_{20}H_{14}F_3NO_6S$ | 453.05 | 452.1 (ES−) |

-continued

| Example | Compound | Molecular Formula | Calculated [M] | Observed (ES+) |
|---|---|---|---|---|
| 70 | 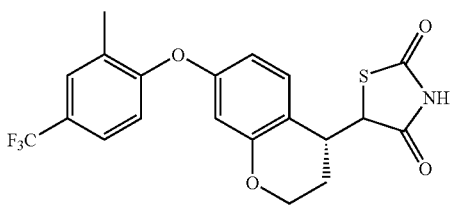 | $C_{20}H_{13}F_3N_2O_4S$ | 434.05 | 435 (ES+) |
| 71 | | $C_{21}H_{18}F_3NO_4S$ | 437.09 | 438 (ES+) |

Example 72

The compound was made by coupling Intermediate 7 with 4-iodo-3-methylbenzotrifluoride, which was made as follows: A mixture of 2-methyl-4-trifluoromethylaniline (9.7 g), 15% sulfuric acid (80 mL), and ethanol (16 mL) was stirred at 0° C. Sodium nitrite (4.2 g) was added to this reaction mixture at 0° C., and the mixture was stirred for 1 h at the same temperature. Sodium iodide (9.97 g) was then added at 0° C., and the mixture was allowed to warm to room temperature over a period of 1.5 h. The reaction mixture was extracted with ethyl acetate (200 mL×3), and the combined organic layer was washed with aqueous saturated sodium sulfite solution and brine, dried over magnesium sulfate, filtered, and concentrated. Silica gel column chromatography with ethyl acetate/hexanes (10/1) as the eluent afforded 4-iodo-3-methylbenzotrifluoride.

To a mixture of Intermediate 7 (183 mg, 0.69 mmol), $Cs_2CO_3$ (730 mg, 2.24 mmol), 4-iodo-3-methyl-benzotrifluoride (0.96 mmol, 274 mg), CuI (0.14 mmol, 26 mg) and N,N-dimethylglycine HCl salt (0.42 mmol, 60 mg) was added DMF (2 mL) and dioxane (2 mL). The reaction was heated at 110° C. for 20 hours and then quenched with 0.1 N HCl (60 mL). The mixture was extracted with EtOAc (3×40 mL). The organic layers were combined, washed with Brine (1×40 mL), dried over anhydrous $Na_2SO_4$ and concentrated in vacuo. The residue was purified by silica gel chromatography (0% to 45% EtOAc/hexanes) to give the desired product as a light yellow solid (mixture of two diastereomers). $R_f$=0.14 (30% EtOAc/hexanes); LC-MS calc. for $C_{20}H_{16}F_3NO_4S$: 423.08 Found (ES+): 423.91 [M+H]; $^1$H NMR (500 MHz, d6-DMSO) for the sodium salt of the major diasteromer δ 7.66 (s, 1H), 7.52 (d, J=8.4 Hz, 1H), 7.32 (d, J=8.4 Hz, 1H), 6.94 (d, J=8.4 Hz, 1H), 6.48 (dd, J=2.4, 8.5 Hz, 1H), 6.32 (d, J=2.5 Hz, 1H), 4.82 (d, J=3.9 Hz, 1H), 4.31-4.27 (m, 1H), 4.03-3.98 (m, 1H), 3.57-3.54 (m, 1H), 2.27 (s, 3H), 1.87-1.83 (m, 1H), 1.64-1.60 (m, 1H).

Example 73

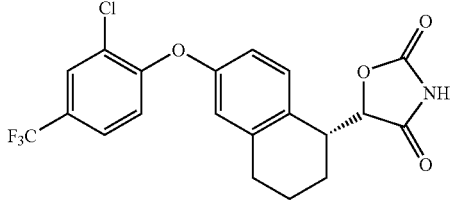

73a

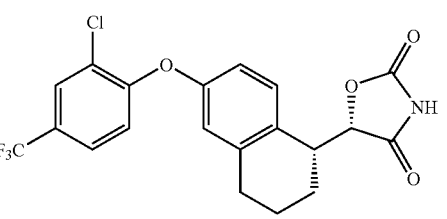

73b

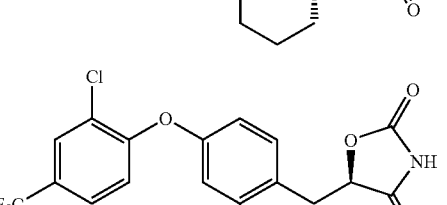

INTERMEDIATE 8 (crude, 125 mg, 0.5 mmol) was combined with 3-chloro-4-fluorobenzotrifluoride (170 mg, 0.6 mmol) and $Cs_2CO_3$ (499 mg, 1.5 mmol) in 5 mL of N,N-dimethylacetamide. The reaction mixture was stirred at 90° C. for 60 min, then was dumped into water and acidified with 2N aq. HCl to pH<2. The resulting solid precipitate was extracted with ethyl acetate and washed with water followed by brine, dried over anhydrous $Na_2SO_4$, filtered, and concentrated. Purification by Combi-Flash (silica, 30-50% ethyl acetate/hexane gradient) gave the product as a mixture of two diastereomers. LC-MS calc. for C20H15ClF3NO4: 425; Found: 426 (M+H). Further separation into two single isomers (74[a] and 74 b) were accomplished on Chiracel AD and OD columns.

Examples 74-86

Compounds with variations on the left side and core of the structure were prepared using the reaction scheme detailed in Example 73, replacing 3-chloro-4-fluoro-benzotrifluoride with corresponding aryl fluorides or aryl chlorides, or using the reaction scheme detailed in Example 41, replacing iodobenzene with corresponding aryl bromide or iodide. All of the reactants and starting materials are either commercially available or are described in the Intermediates section or are readily prepared by a practitioner in the field of synthetic organic chemistry. Two single isomers were prepared by chiral HPLC on OD or AD columns. These compounds are summarized in the table below.

| Example | Compound | Molecular Formula | Calculated [M] | Observed (ES+) |
|---|---|---|---|---|
| 74 | | $C_{21}H_{18}F_3NO_4$ | 450.12 | 451.0 (ES+) |
| 74a | | $C_{21}H_{18}F_3NO_4$ | 450.12 | 451.0 (ES+) |
| 74b | | $C_{21}H_{18}F_3NO_4$ | 450.12 | 451.0 (ES+) |
| 75 | | $C_{24}H_{18}N_2O_4$ | 398.13 | 399.0 (ES+) |
| 75a | | $C_{24}H_{18}N_2O_4$ | 398.13 | 399.0 (ES+) |

| Example | Compound | Molecular Formula | Calculated [M] | Observed (ES+) |
|---|---|---|---|---|
| 75b | | $C_{24}H_{18}N_2O_4$ | 398.13 | 399.0 (ES+) |
| 76 | | $C_{19}H_{14}ClF_3N_2O_4$ | 426.06 | 427.0 (ES+) |
| 76a | | $C_{19}H_{14}ClF_3N_2O_4$ | 426.06 | 427.0 (ES+) |
| 76b | | $C_{19}H_{14}ClF_3N_2O_4$ | 426.06 | 427.0 (ES+) |
| 77 | | $C_{21}H_{18}N_2O_4$ | 362.13 | 363.0 (ES+) |
| 79 | | $C_{21}H_{15}F_3NO_5S$ | 416.10 | 417.2 (ES−) |
| 79a | | $C_{21}H_{15}F_3NO_5S$ | 416.10 | 417.2 (ES−) |

-continued

| Example | Compound | Molecular Formula | Calculated [M] | Observed (ES+) |
|---|---|---|---|---|
| 79b | | $C_{21}H_{15}F_3NO_5S$ | 416.10 | 417.2 (ES−) |
| 80 | | $C_{22}H_{20}F_3NO_4$ | 419.13 | 420.0 (ES−) |
| 80a | | $C_{22}H_{20}F_3NO_4$ | 419.13 | 420.0 (ES−) |
| 80b | | $C_{22}H_{20}F_3NO_4$ | 419.13 | 420.0 (ES−) |
| 81 | | $C_{20}H_{15}ClN_3O_4$ | 382.07 | 383 (ES+) |
| 81a | | $C_{20}H_{15}ClN_3O_4$ | 382.07 | 383 (ES+) |
| 82b | | $C_{20}H_{15}ClN_3O_4$ | 382.07 | 383 (ES+) |

-continued

| Example | Compound | Molecular Formula | Calculated [M] | Observed (ES+) |
|---------|----------|-------------------|----------------|----------------|
| 83 | 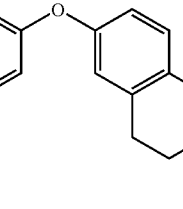 | C20H15BrN2O4 | 426.02 | 427 (ES+) |
| 84 | 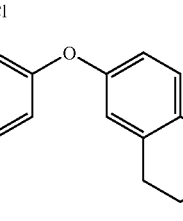 | C21H17ClF3NO4 | 439.08 | 438 (ES−) |
| 85 | 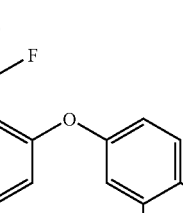 | C21H15F6NO4 | 459.09 | 469 (ES+) |
| 86 | 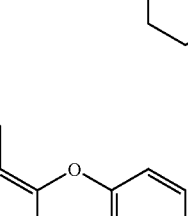 | C24H18F3NO4 | 441.12 | 440 (ES−) |

Example 87

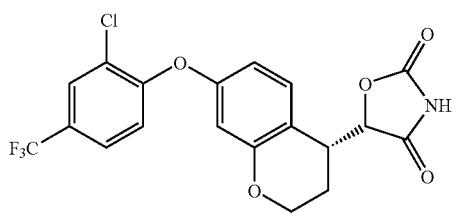

INTERMEDIATE 9 (crude, 25 mg, 0.1 mmol) was combined with 3-chloro-4-fluorobenzotrifluoride (20 mg, 0.1 mmol) and $Cs_2CO_3$ (97.5, 0.3 mmol) in 2 mL of N,N-dimethylacetamide. The reaction mixture was stirred at 90° C. for 60 min, then was dumped into water and acidified with 2N aq. HCl to pH<2. The resulting solid precipitate was extracted with ethyl acetate and washed with water followed by brine, dried over anhydrous $Na_2SO_4$, filtered, and concentrated. Purification by Combi-Flash (silica, 30-50% ethyl acetate/hexane gradient) gave the product. LC-MS calc. for C19H13ClF3NO5: 427; Found: 428 (M+H).

Examples 88-93

Compounds with variations on the left side and core of the structure were prepared using the reaction scheme detailed in Example 87, replacing 3-chloro-4-fluoro-benzotrifluoride with corresponding aryl fluorides or aryl chlorides, or using the reaction scheme detailed in Example 41, replacing iodobenzene with corresponding aryl bromide or iodide. All of the reactants and starting materials are either commercially available or are described in the Intermediates section or are readily prepared by a practitioner in the field of synthetic organic chemistry. Two single isomers were prepared by chiral HPLC on OD or AD columns. These compounds are summarized in the table below.

| | | | | |
|---|---|---|---|---|
| 88 | 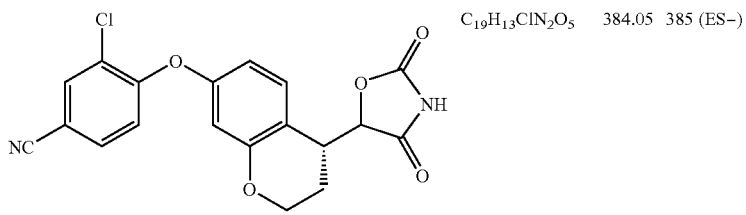 | C<sub>19</sub>H<sub>13</sub>ClN<sub>2</sub>O<sub>5</sub> | 384.05 | 385 (ES−) |
| 89 | 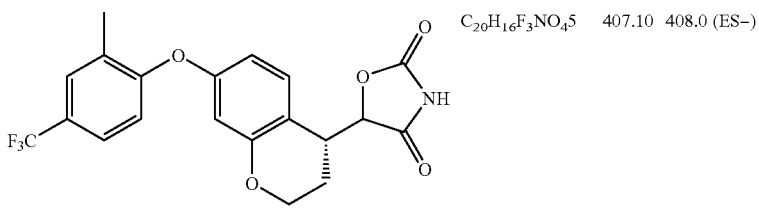 | C<sub>20</sub>H<sub>16</sub>F<sub>3</sub>NO<sub>4</sub>5 | 407.10 | 408.0 (ES−) |
| 90 | 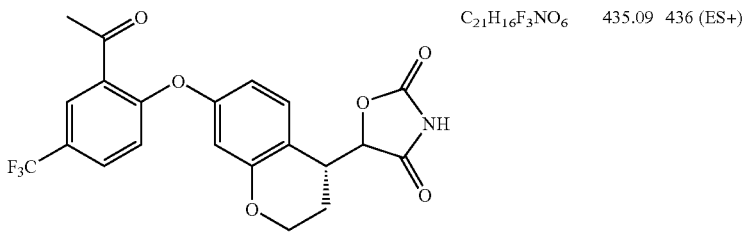 | C<sub>21</sub>H<sub>16</sub>F<sub>3</sub>NO<sub>6</sub> | 435.09 | 436 (ES+) |
| 91 | 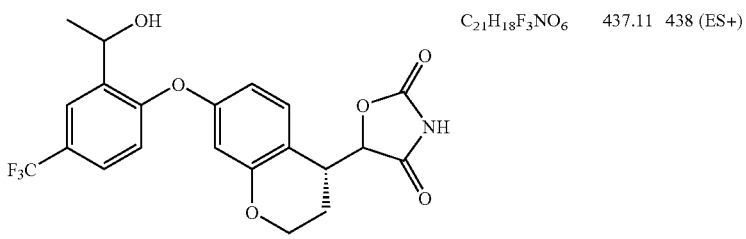 | C<sub>21</sub>H<sub>18</sub>F<sub>3</sub>NO<sub>6</sub> | 437.11 | 438 (ES+) |
| 92 | 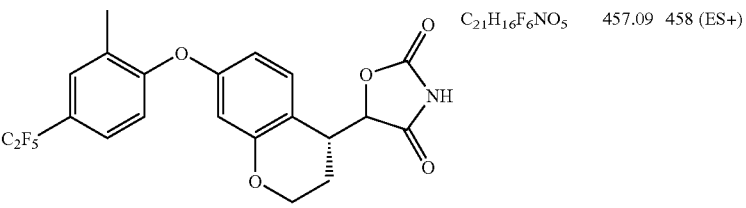 | C<sub>21</sub>H<sub>16</sub>F<sub>6</sub>NO<sub>5</sub> | 457.09 | 458 (ES+) |
| 93 | 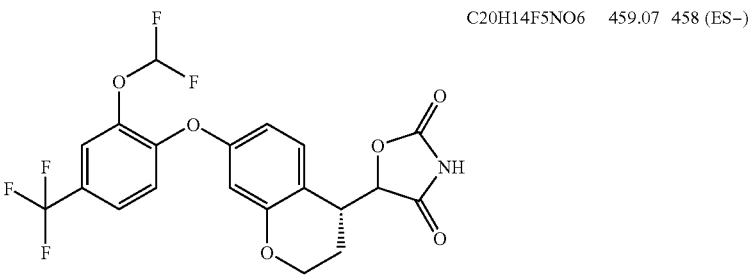 | C20H14F5NO6 | 459.07 | 458 (ES−) |

-continued

| | | | | |
|---|---|---|---|---|
| 93a | 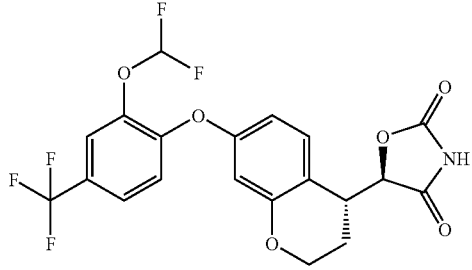 | C20H14F5NO6 | 459.07 | 458 (ES−) |
| 93b | 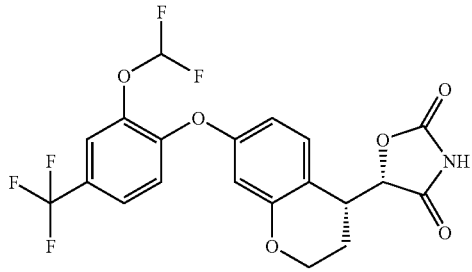 | C20H14F5NO6 | 459.07 | 458 (ES−) |

Example 94

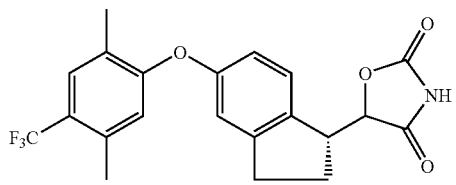

To a mixture of Intermediate 5 (162 mg, 0.69 mmol), Cs$_2$CO$_3$ (730 mg, 2.24 mmol), 4-bromo-2,3-dimethyl-benzotrifluoride (0.96 mmol, 241 mg), CuI (0.14 mmol, 26 mg) and N,N-dimethylglycine HCl salt (0.42 mmol, 60 mg) was added DMF (2 mL) and dioxane (2 mL). The reaction was heated at 110° C. for 20 hours and then quenched with 0.1 N HCl (60 mL). The mixture was extracted with EtOAc (3×40 mL). The organic layers were combined, washed with Brine (1×40 mL), dried over anhydrous Na$_2$SO$_4$ and concentrated in vacuo. The residue was purified by silica gel chromatography (0% to 45% EtOAc/hexanes) to give the desired product as a light yellow solid (mixture of two diastereomers). LC-MS calc. for C$_{21}$H$_{18}$F$_3$NO$_4$: 405.12 Found (ES+): 406 [M+H].

Examples 95-128

Compounds with variations on the left side and core of the structure were prepared using the reaction scheme detailed in Example 54, replacing 3-chloro-4-fluoro-benzotrifluoride with other corresponding aryl fluorides or aryl chlorides, or using the reaction scheme detailed in Example 94, replacing 4-bromo-2,3-dimethyl-benzotrifluoride with other corresponding aryl bromide or iodide. All of the reactants and starting materials are either commercially available or are described in the Intermediates section or are readily prepared by a practitioner in the field of synthetic organic chemistry. Two single isomers were prepared by chiral HPLC on OD or AD columns. These compounds are summarized in the table below.

| | | | | |
|---|---|---|---|---|
| 95 | 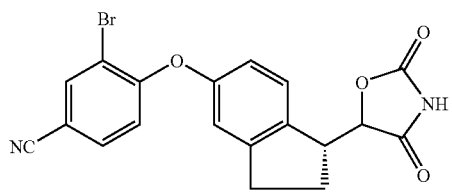 | C$_{19}$H$_{13}$BrN$_2$O$_4$ | 412.01 | 413 (ES−) |
| 96 | 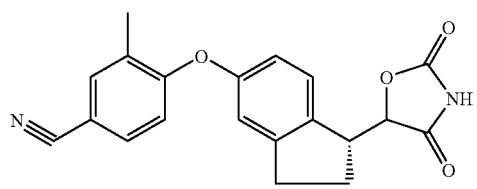 | C20H16N2O4 | 348.11 | 349 (ES+) |

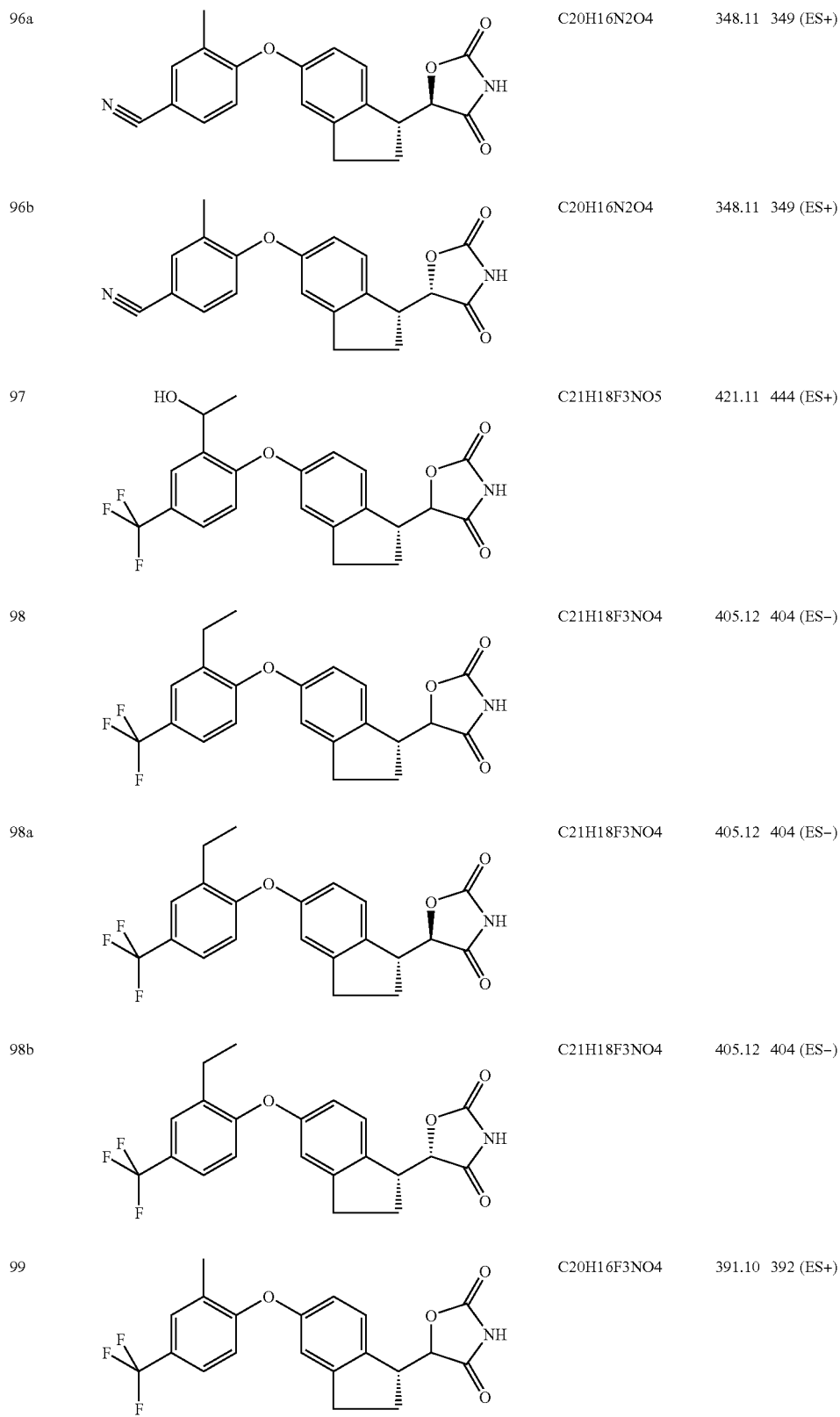

-continued
| | | | | |
|---|---|---|---|---|
| 99a | 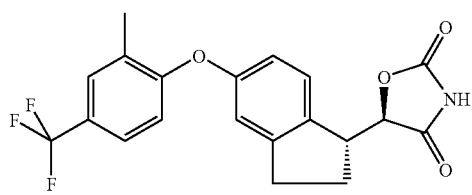 | C20H16F3NO4 | 391.10 | 392 (ES+) |
| 99b | 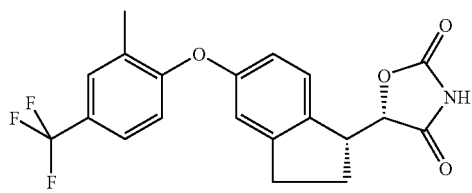 | C20H16F3NO4 | 391.10 | 392 (ES+) |
| 100 | 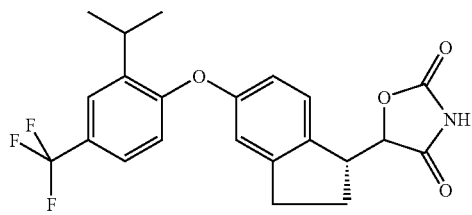 | C22H20F3NO4 | 419.13 | 418 (ES−) |
| 100a | 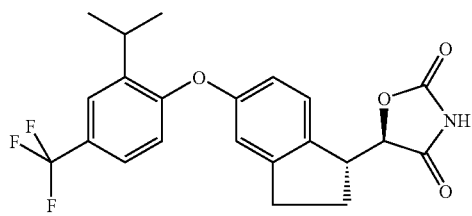 | C22H20F3NO4 | 419.13 | 418 (ES−) |
| 100b | 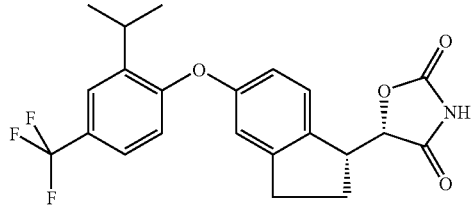 | C22H20F3NO4 | 419.13 | 418 (ES−) |
| 101 | 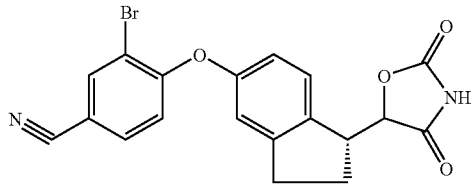 | C19H13BrN2O4 | 412.01 | 413 (ES+) |
| 101a | 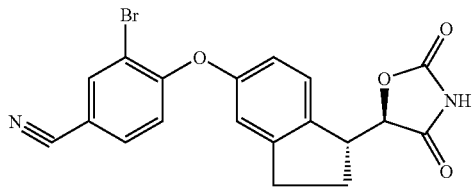 | C19H13BrN2O4 | 412.01 | 413 (ES+) |

-continued
| | | | | |
|---|---|---|---|---|
| 101b | 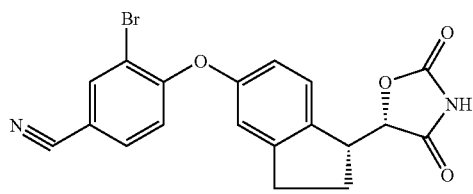 | C19H13BrN2O4 | 412.01 | 413 (ES+) |
| 102 | 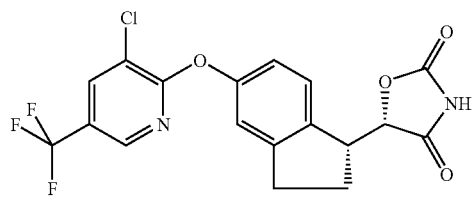 | C18H12ClF3N2O4 | 412.04 | 413 (ES+) |
| 103 | 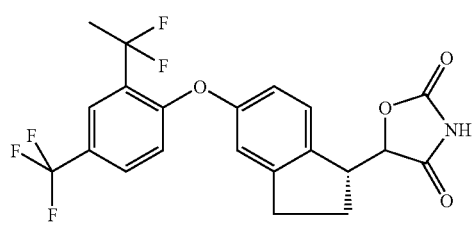 | C21H16F5NO4 | 441.10 | 440 (ES−) |
| 104 | 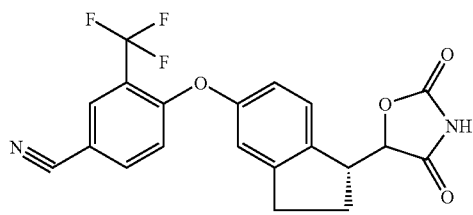 | C20H13F3N2O4 | 402.08 | 403 (ES+) |
| 105 | 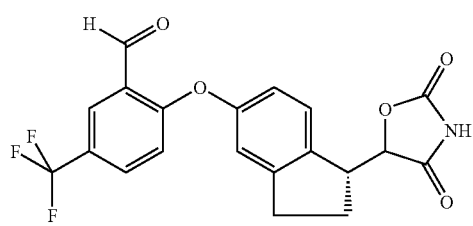 | C20H14F3NO5 | 405.08 | 388 (ES+) |
| 106 | 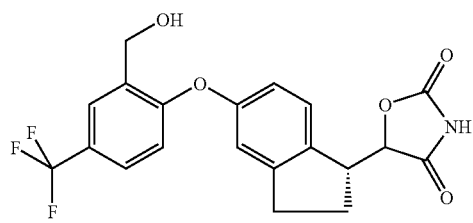 | C20H16F3NO5 | 407.10 | 406 (ES−) |
| 107 | 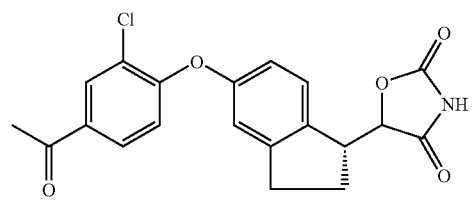 | C20H16ClNO5 | 385.07 | 386 (ES−) |

-continued
| | | | | |
|---|---|---|---|---|
| 108 | 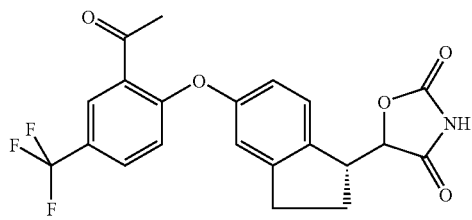 | C21H16F3NO5 | 419.10 | 420 (ES+) |
| 109 | 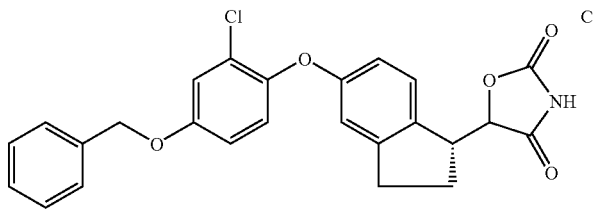 | C25H20ClNO5 | 449.10 | 448 (ES−) |
| 110 | 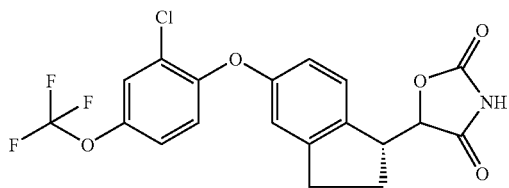 | C19H13ClF3NO5 | 427.04 | 426 (ES−) |
| 111 | 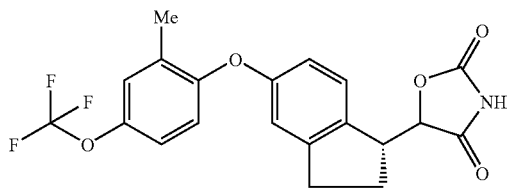 | C20H16F3NO5 | 407.10 | 406 (ES−) |
| 112 | 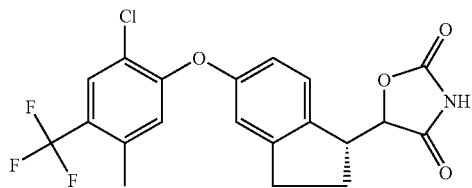 | C20H15ClF3NO4 | 425.06 | 424 (ES−) |
| 113 | 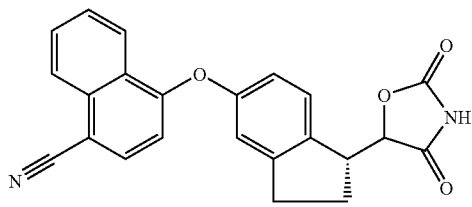 | C23H16N2O4 | 384.11 | 385 (ES+) |
| 113a | 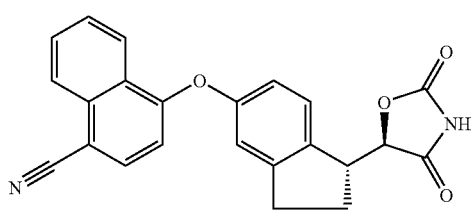 | C23H16N2O4 | 384.11 | 385 (ES+) |

-continued
| | | | | |
|---|---|---|---|---|
| 113b | 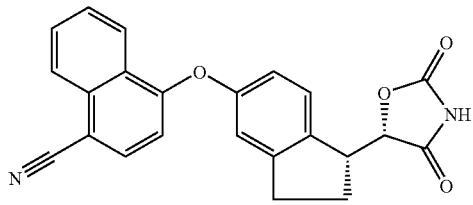 | C23H16N2O4 | 384.11 | 385 (ES+) |
| 114 | 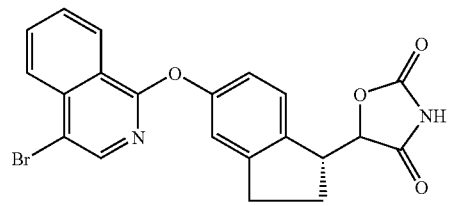 | C21H15BrN2O4 | 438.02 | 439 (ES+) |
| 115 | 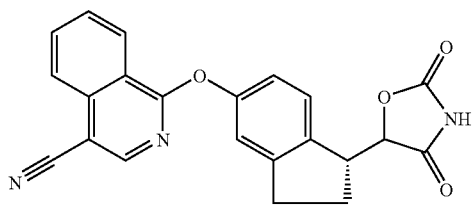 | 22H15N3O4 | 385.11 | 386 (ES+) |
| 115a | 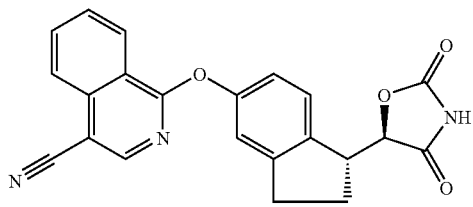 | 22H15N3O4 | 385.11 | 386 (ES+) |
| 115b | 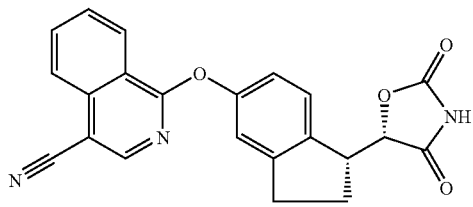 | 22H15N3O4 | 385.11 | 386 (ES+) |
| 116 | 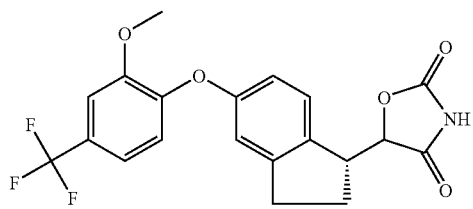 | C20H16F3NO5 | 407.1 | 408 (ES+) |
| 116a | 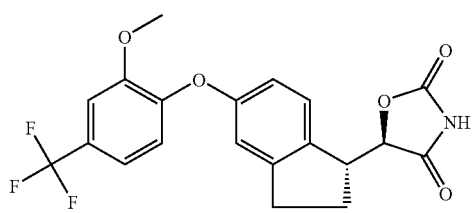 | C20H16F3NO5 | 407.1 | 408 (ES+) |

-continued
| | | | | |
|---|---|---|---|---|
| 116b | 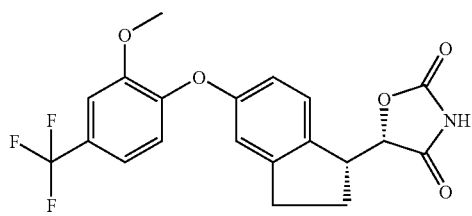 | C20H16F3NO5 | 407.1 | 408 (ES+) |
| 117 | 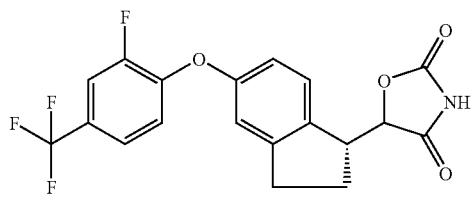 | C19H13F4NO4 | 395.08 | 396 (ES+) |
| 118 | 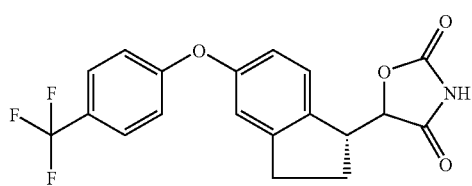 | C19H14F3NO4 | 377.09 | 378 (ES+) |
| 119 | 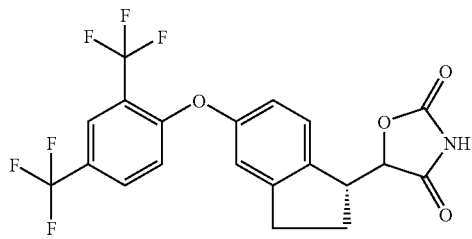 | C20H13F6NO4 | 445.07 | 444 (ES−) |
| 119a | 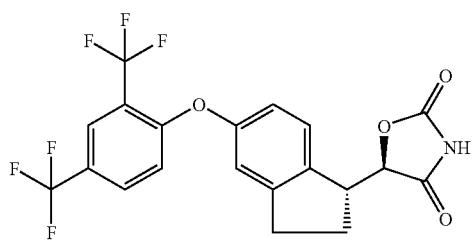 | C20H13F6NO4 | 445.07 | 444 (ES−) |
| 119b | 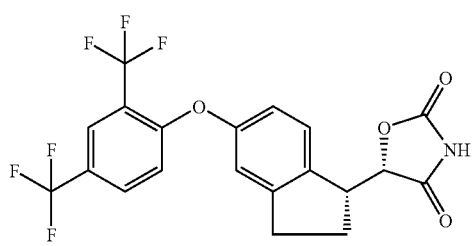 | C20H13F6NO4 | 445.07 | 444 (ES−) |
| 120 | 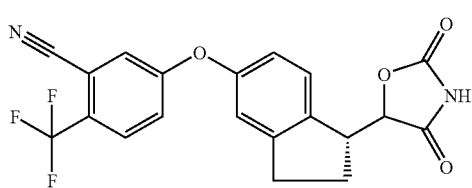 | C20H13F3N2O4 | 402.08 | 403 (ES+) |

-continued
| | | | | |
|---|---|---|---|---|
| 121 | 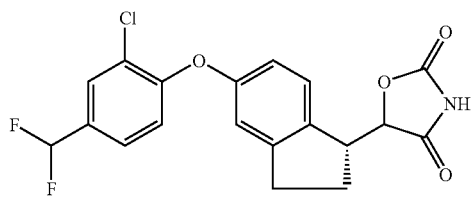 | C19H14ClF2NO4 | 393.06 | 392 (ES−) |
| 122 | 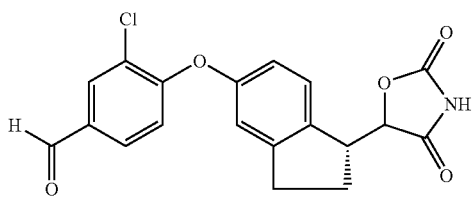 | C19H14ClNO5 | 371.06 | 372 (ES+) |
| 123 | 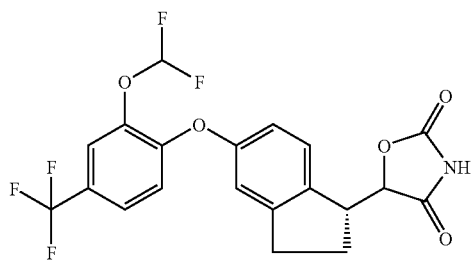 | C20H14F5NO5 | 443.08 | 424 (ES+) |
| 123a | 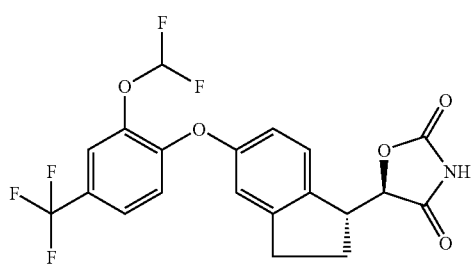 | C20H14F5NO5 | 443.08 | 424 (ES+) |
| 123b | 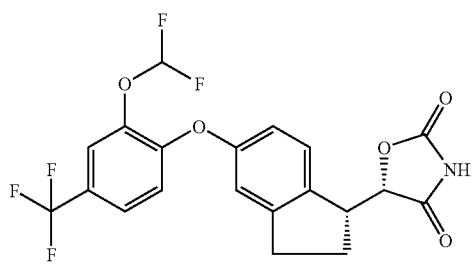 | C20H14F5NO5 | 443.08 | 424 (ES+) |
| 124 | 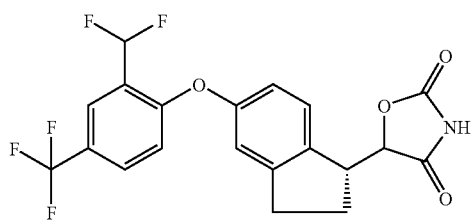 | C20H14F5NO4 | 427.08 | 426 (ES−) |

-continued
| | | | | |
|---|---|---|---|---|
| 124a | 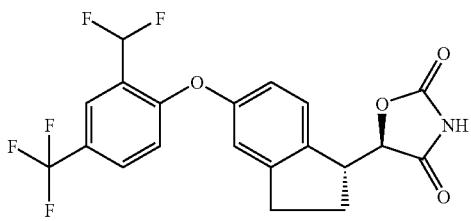 | C20H14F5NO4 | 427.08 | 426 (ES−) |
| 124b | 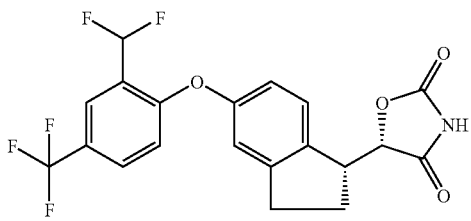 | C20H14F5NO4 | 427.08 | 426 (ES−) |
| 125 | 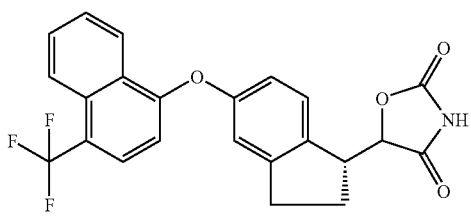 | C23H16F3NO4 | 427.10 | 426 (ES−) |
| 125a | 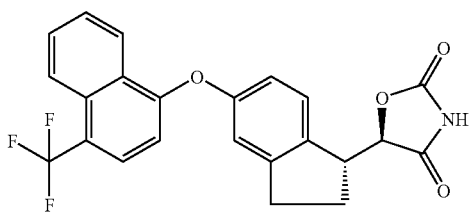 | C23H16F3NO4 | 427.10 | 426 (ES−) |
| 125b | 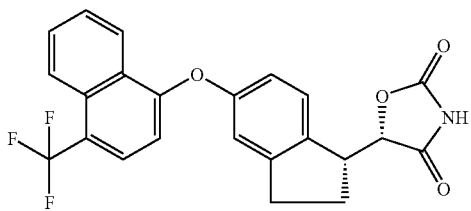 | C23H16F3NO4 | 427.10 | 426 (ES−) |
| 126 | 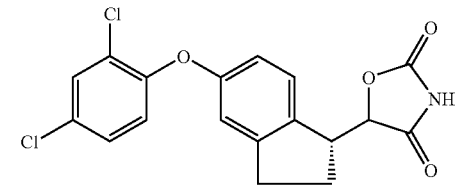 | C18H13Cl2NO4 | 377.02 | 376 (ES−) |
| 126a | 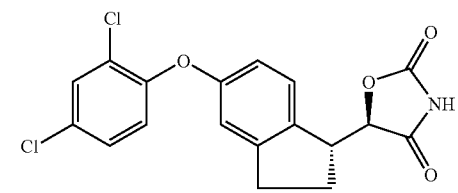 | C18H13Cl2NO4 | 377.02 | 376 (ES−) |

-continued
| | | | | |
|---|---|---|---|---|
| 126b | 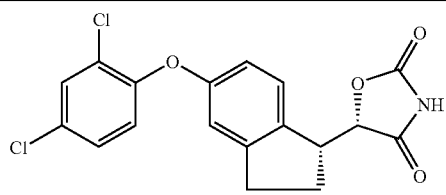 | C18H13Cl2NO4 | 377.02 | 376 (ES−) |
| 127 | 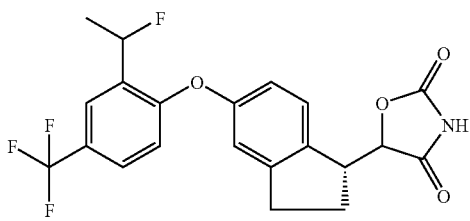 | C21H17F4NO4 | 423.11 | 422 (ES−) |
| 127a | 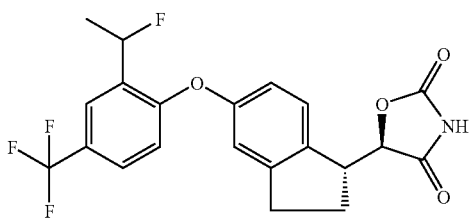 | C21H17F4NO4 | 423.11 | 422 (ES−) |
| 127b | 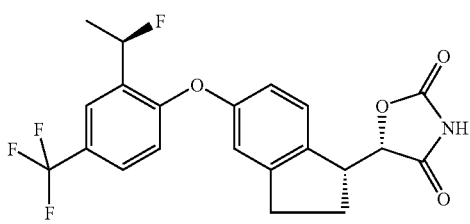 | C21H17F4NO4 | 423.11 | 422 (ES−) |
| 127c | 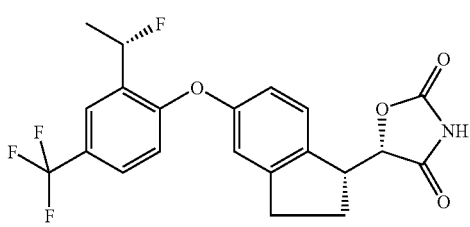 | C21H17F4NO4 | 423.11 | 422 (ES−) |
| 128 | 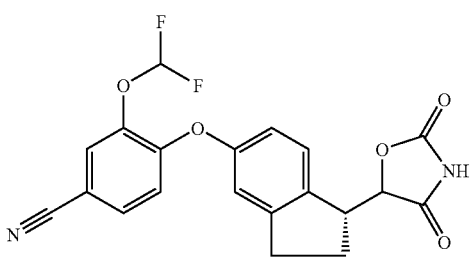 | C20H14F2N2O5 | 400.09 | 399 (ES−) |
| 128a | 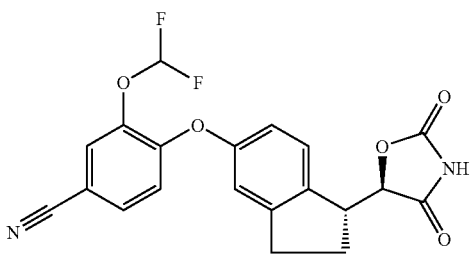 | C20H14F2N2O5 | 400.09 | 399 (ES−) |

| | | | | |
|---|---|---|---|---|
| 128b | 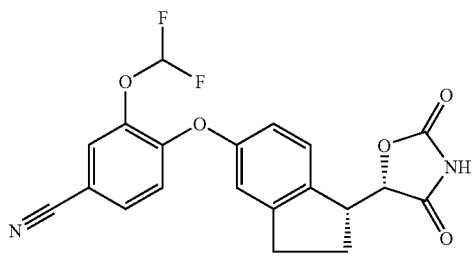 | C20H14F2N2O5 | 400.09 | 399 (ES−) |

Examples 129-182

Compounds with variations on the left side and right side of the structure were prepared using one of the following methods: a) using the reaction scheme detailed in Examples 54, replacing Intermediate 5 with Intermediate 1, 2, or 7, and replacing 3-chloro-4-fluoro-benzotrifluoride with other corresponding aryl fluorides or aryl chlorides; b) using the reaction scheme detailed in Example 94, replacing Intermediate 5 with Intermediate 1, 2, or 7, and replacing 4-bromo-2,3-dimethyl-benzotrifluoride with other corresponding aryl bromides or iodides. All of the reactants and starting materials are either commercially available or are described in the Intermediates section or are readily prepared by a practitioner in the field of synthetic organic chemistry. These compounds are summarized in the table below.

| Example | Compound | Molecular Formula | Calculated [M] | Observed (ES+) |
|---|---|---|---|---|
| 129 | | C23H16F3NO4S | 459.08 | 458 (ES−) |
| 130 | | C20H13F5NO5S | 474.04 | 473 (ES−) |
| 131 | | C22H15N3O3S | 401.08 | 402 (ES+) |
| 132 | | C22H15F3N2O3S | 444.08 | 445 (ES+) |

-continued

| Example | Compound | Molecular Formula | Calculated [M] | Observed (ES+) |
| --- | --- | --- | --- | --- |
| 133 | | C21H15F5NO4S | 472.06 | 471 (ES−) |
| 134 | | C24H18F3NO3S | 457.1 | 456 (ES−) |
| 135 | | C20H13F5NO4S | 458.05 | 457 (ES−) |
| 136 | | C23H16F3NO3S | 443.08 | 442 (ES−) |
| 137 | | C20H16F3NO3S | 407.08 | 406 (ES−) |
| 138 | | C21H18F3NO3S | 421.1 | 420 (ES−) |
| 139 | | C21H16F3NO4S | 435.08 | 434 (ES−) |

-continued

| Example | Compound | Molecular Formula | Calculated [M] | Observed (ES+) |
|---|---|---|---|---|
| 140 | | C21H18F3NO4S | 437.09 | 436 (ES−) |
| 141 | | C22H20F3NO3S | 435.11 | 434 (ES−) |
| 142 | | C21H16F5NO3S | 457.08 | 456 (ES−) |
| 143 | | C21H17F4NO3S | 439.09 | 438 (ES−) |
| 144 | | C20H15F4NO3S | 425.07 | 424 (ES−) |
| 145 | | C22H20F3NO3S | 435.11 | 434 (ES−) |

-continued

| Example | Compound | Molecular Formula | Calculated [M] | Observed (ES+) |
|---|---|---|---|---|
| 146 | | C24H24F3NO3S | 463.14 | 462 (ES−) |
| 147 | | C20H14F5NO3S | 443.06 | 442 (ES−) |
| 148 | | C20H16F3NO5S2 | 471.04 | 470 (ES−) |
| 149 | | C20H15F3N2O4S | 436.07 | 435 (ES−) |
| 150 | | C20H14F3NO4S | 421.06 | 420 (ES−) |
| 151 | | C20H16F3NO4S | 423.08 | 422 (ES−) |

-continued

| Example | Compound | Molecular Formula | Calculated [M] | Observed (ES+) |
|---------|----------|-------------------|----------------|----------------|
| 152 | | C20H16F3NO4S | 423.08 | 422 (ES−) |
| 153 | | C22H18F3NO5S | 465.09 | 464 (ES−) |
| 154 | | C19H14F3NO3S | 393.06 | 392 (ES−) |
| 155 | | C19H13F4NO3S | 411.06 | 410 (ES−) |
| 156 | | C20H13F3N2O3S | 418.06 | 419 (ES+) |
| 157 | | C20H17F3N2O3S | 422.09 | 423 (ES+) |
| 158 | | C19H15F3N2O3S | 408.08 | 409 (ES+) |

-continued

| Example | Compound | Molecular Formula | Calculated [M] | Observed (ES+) |
|---|---|---|---|---|
| 159 | | C20H14ClF4NO3S | 459.03 | 458 (ES−) |
| 160 | | C19H14F3NO4S | 409.06 | 408 (ES−) |
| 161 | | C19H13ClF3NO4S | 443.02 | 442 (ES−) |
| 162 | | C20H16F3NO4S | 423.08 | 422 (ES−) |
| 163 | | C19H15F2NO4S | 391.07 | 390 (ES−) |
| 164 | | C22H21NO3S | 379.12 | 378 (ES−) |
| 165 | | C21H18ClNO3S | 399.07 | 398 (ES−) |

-continued

| Example | Compound | Molecular Formula | Calculated [M] | Observed (ES+) |
|---|---|---|---|---|
| 166 | | C21H19NO3S | 365.11 | 364 (ES−) |
| 167 | | C21H17NO4S | 379.09 | 380 (ES+) |
| 168 | | C21H21ClN2O3S | 416.1 | 417.1 (ES+) |
| 169 | | C23H23ClN2O3S | 442.11 | 443 (ES−) |
| 170 | | C24H26N2O5S | 454.16 | 455 (ES+) |
| 171 | | C22H17ClF2N2O4S | 478.06 | 479 (ES+) |
| 172 | | C20H16ClNO5S | 417.04 | 416 (ES−) |

-continued

| Example | Compound | Molecular Formula | Calculated [M] | Observed (ES+) |
|---|---|---|---|---|
| 173 | | C21H18ClNO5S | 431.06 | 430 (ES−) |
| 174 | | C20H16ClNO4S | 401.05 | 402 (ES+) |
| 175 | | C19H14ClNO4S | 387.03 | 386 (ES−) |
| 176 | | C20H16ClF2NO3S | 423.05 | 422 (ES−) |
| 177 | | C19H14ClF2NO3S | 409.04 | 408 (ES−) |
| 178 | | C18H13Cl2NO3S | 393.00 | 392 (ES−) |
| 179 | | C20H14F2N2O4S | 416.06 | 417 (ES+) |

| Example | Compound | Molecular Formula | Calculated [M] | Observed (ES+) |
|---|---|---|---|---|
| 180 | | C21H16F2N2O4S | 430.08 | 431 (ES+) |
| 181 | | C20H15ClF3NO3S | 441.04 | 440 (ES–) |
| 182 | 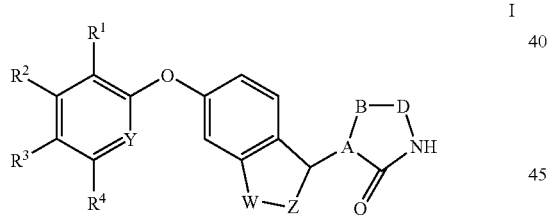 | C20H13F3N2O3S | 418.06 | 419 (ES+) |

What is claimed is:

1. A compound of formula I, or a pharmaceutically acceptable salt, stereoisomer, diastereomer or enantiomer thereof,

I wherein A is selected from the group consisting of —CH— and —N—;

B is selected from the group consisting of —S—, —O—, —NH—, —C(=O)—, and —CH$_2$—;

D is selected from the group consisting of —C(=O)—, —C(=S)—, —C(=NH)—, —O—, and —NH—;

W and Z are independently selected from —CH$_2$—, —CF$_2$—, —CH$_2$CH$_2$—, and —CH$_2$CH$_2$CH$_2$—, and one of W and Z optionally may be selected from —O—, —C(=O)—, —NR$^6$—, —S—, —S(O)—, and —S(O)$_2$—;

Y is selected from =CH— and =N—;

Heterocycle is a 5-6 membered saturated or partly saturated monocyclic heterocyclic ring having 1-3 heteroatoms independently selected from O, N and S;

Heteroaryl is a 5-6 membered monocyclic heteroaromatic ring having 1-3 heteroatoms independently selected from O, N and S;

$R^1$, $R^2$, $R^3$ and $R^4$ are each independently selected from the group consisting of H, halogen, —CN, —NO$_2$, —C$_1$-C$_6$alkyl, —OC$_1$-C$_6$alkyl, —SC$_1$-C$_6$alkyl, —S(O)$_2$C$_1$-C$_6$alkyl, —N(R$^6$)(R$^6$), —N(R$^6$)C(=O)C$_1$-C$_6$alkyl, —N(R$^6$)S(O)$_2$C$_1$-C$_6$alkyl, —C(=O)H, —C(=O)OH, —C(=O)—OC$_1$-C$_6$alkyl, —C(=O)C$_1$-C$_6$alkyl, —C(=O)N(R$^6$)(R$^6$), —C(=O)phenyl, —C(=O)naphthyl, —C(=O)Heterocyle, Heterocycle, Heteroaryl, C$_3$-C$_7$-cycloalkyl, phenyl and naphthyl;

wherein —C$_1$-C$_6$alkyl and the alkyl groups of —OC$_1$-C$_6$alkyl, —SC$_1$-C$_6$alkyl, —S(O)$_2$C$_1$-C$_6$alkyl, —N(R$^6$)C(=O)C$_1$-C$_6$alkyl, —N(R$^6$)S(O)$_2$C$_1$-C$_6$alkyl, —C(=O)OC$_1$-C$_6$alkyl, and —C(=O)C$_1$-C$_6$alkyl are optionally substituted with 1-5 halogens and are optionally also substituted with 1-2 groups independently selected from —OH, —OC$_1$-C$_3$alkyl which is optionally substituted with 1-5 halogens, —CF$_3$, —S(O)$_2$C$_1$-C$_3$alkyl, —C(=O)C$_1$-C$_3$alkyl, —OC(=O)C$_1$-C$_6$alkyl, —NHC(=O)CH$_3$, —NHC(=O)—OC$_1$-C$_6$alkyl, —NHS(O)$_2$CH$_3$, —N(R$^6$)(R$^6$), Heterocycle, Heteroaryl, C$_3$-C$_7$-cycloalkyl, phenyl, and naphthyl;

wherein —C(=O)phenyl, —C(=O)naphthyl, —C(=O)Heterocyle, Heterocycle, Heteroaryl, C$_3$-C$_7$-cycloalkyl, phenyl and naphthyl either as $R^1$, $R^2$, $R^3$, $R^4$, or as substituents on $R^1$, $R^2$, $R^3$ and $R^4$ are optionally substituted with 1-4 substituents independently selected from halogen, —CF$_3$, —OCF$_3$, —CN, —NO$_2$, —OH, —C$_1$-C$_3$allyl, —C(=O)C$_1$-C$_3$alkyl, —S(O)$_2$C$_1$-C$_3$alkyl, and —OC$_1$-C$_3$alkyl, wherein said —C$_1$-C$_3$alkyl, —OC$_1$-C$_3$alkyl, —S(O)$_2$C$_1$-C$_3$alkyl, and —C(=O)C$_1$-C$_3$alkyl substituents are optionally substituted with 1-3 halogens; and wherein alternatively one pair of ortho substituents selected from ($R^1$-$R^2$), ($R^2$-$R^1$), ($R^2$-$R^3$), ($R^3$-$R^2$), ($R^3$-$R^4$), and ($R^4$-

R³) may be connected to form a divalent bridging group having a length of 3-5 atoms, wherein said divalent bridging group is selected from —CH₂CH₂CH₂—, —CH₂CH₂CH₂CH₂—, —CH₂CH₂CH₂CH₂CH₂—, —CH₂CH₂O—, —OCH₂CH₂—, —OCH₂CH₂CH₂—, —OCH₂CH₂CH₂CH₂—, —CH₂OCH₂—, —CH₂OCH₂CH₂—, —CH₂OCH₂CH₂CH₂—, —CH₂CH₂OCH₂CH₂—, and —CH₂CH₂S—SCH₂CH₂—, wherein said bridging group is optionally substituted with 1-3 substituent groups independently selected from halogen, —OH, —CN, —NO₂, —C₁-C₃alkyl, —OC₁-C₃alkyl, —SC₁-C₃alkyl, —S(O)₂C₁-C₃alkyl, —CF₃, and —OCF₃; and wherein alternatively the pair of ortho substituents R¹-R² may be connected by the 4-carbon chain —CH=CH—CH=CH— to form a fused phenyl ring at the R¹ and R² positions, or by a 4-atom chain selected from —CH=CH—CH=N—, —N=CH—CH=CH—, —CH=N—CH=CH—, —CH=CH—N=CH—, —CH₂CH₂CH₂C(=O)—, and —C(=O)CH₂CH₂CH₂—, to form a fused pyridinyl ring or a fused cyclohexanone ring at the R¹ and R² positions, wherein said fused phenyl ring, said fused pyridinyl ring, and said fused cyclohexanone ring are optionally substituted with 1-3 substituents independently selected from halogen, —OH, —CN, —NO₂, —C₁-C₃alkyl, —OC₁-C₃alkyl, —SC₁-C₃alkyl, —S(O)₂C₁-C₃alkyl, —CF₃, and —OCF₃; and wherein alternatively the pair of ortho substituents R¹-R² may be connected by a 3-atom chain selected from —CH=CHO—, —OCH=CH—, —CH=CH—S—, —SCH=CH—, —CH=CHN(R⁶)—, —N(R⁶)CH=CH—, —CH₂CH₂C(=O)—, and —C(=O)CH₂CH₂—, to form a five-membered ring fused to the phenyl ring at the R¹ and R² positions, wherein said fused five-membered ring is optionally substituted with 1-3 substituents independently selected from halogen, —OH, —CN, —NO₂, —C₁-C₃alkyl, —OC₁-C₃alkyl, —SC₁-C₃alkyl, —S(O)₂C₁-C₃allyl, —CF₃, and —OCF₃; and R⁶ is selected from the group consisting of H and —C₁-C₆alkyl.

2. The compound of claim 1, or a pharmaceutically acceptable salt, stereoisomer, diastereomer or enantiomer thereof, wherein R¹, R², R³, and R⁴ are independently selected from (1) H; (2) Halogen; (3) —NO₂; (4) —CN; (5) —C₁₋₆alkyl, which is optionally substituted with 1-5 halogens and is optionally also substituted with 1-2 substituents which are independently selected from —OH, —CF₃, —C(=O)C₁-C₃alkyl, and —OC₁₋₃alkyl which is optionally substituted with 1-3 halogens;

(6) —OC₁-C₆alkyl, which is optionally substituted with 1-5 halogens and is optionally also substituted with 1-2 groups independently selected from —CF₃ and —C(=O)C₁-C₃alkyl; (7) —C(=O)C₁-C₃alkyl, which is optionally substituted with 1-5 halogens and is optionally also substituted with 1-2 groups independently selected from —CF₃; (8) C₃-C₇cycloalkyl; (9) phenyl; and (10) Heterocycle, wherein C₃-C₇cycloalkyl, phenyl, and Heterocycle are each optionally substituted with 1-3 substituents independently selected from halogen, —OH, —OC₁₋₃alkyl, CF₃, and —C(=O)C₁-C₃alkyl.

3. The compound of claim 1, or a pharmaceutically acceptable salt, stereoisomer, diastereomer or enantiomer thereof, wherein R¹, R², R³, and R⁴ are each independently selected from H, F, Br, Cl, CH₃, CF₃, —CH₂OH, —CH(OH)CH₃, —C(=O)H, —C(=O)OH, —C(=O)CH₃, —CH₂CH₃, —CH₂CF₃, cyclopropyl, —CN, —OCH₃, —OCF₃, —NO₂, CH(CH₃)₂, n-C₃H₇, n-C₅H₁₁, —C₂F₅, —CHFCH₃, —CHFCF₃, —CF₂CH₃, —CHF₂, —CH₂F, —OCHF₂, —OCH₂F, —OCH₂-phenyl, —C(=O)—OCH₃, —S(O)₂CH₃, —C(=O)NH₂, —CH₂OC(=O)CH₃, —NH₂, —CH₂NH₂, —CH₂N(CH₃)₂, —CH₂NHC(=O)OC(CH₃)₃, —CH₂(1-pyrrolidinyl), and —C(=O)(3,3-difluoro-1-azetidinyl).

4. The compound of claim 3, or a pharmaceutically acceptable salt, stereoisomer, diastereomer or enantiomer thereof, wherein R¹, R², R³, and R⁴ are each independently selected from H, F, Br, Cl, CH₃, CF₃, —CH₂OH, —CH(OH)CH₃, —C(=O)H, —C(=O)OH, —C(=O)CH₃, —CH₂CH₃, —CH₂CF₃, cyclopropyl, —CN, —OCH₃, —OCF₃, and —NO₂.

5. The compound of claim 1, or a pharmaceutically acceptable salt, stereoisomer, diastereomer or enantiomer thereof, wherein R¹ and R² are connected by the 4-carbon chain —CH=CH—CH=CH— to form a fused phenyl ring at the R¹ and R² positions, wherein said fused phenyl ring is optionally substituted with 1-3 substituents independently selected from halogen, —OH, —CN, —NO₂, —C₁-C₃alkyl, —OC₁-C₃alkyl, —SC₁-C₃alkyl, —S(O)₂C₁-C₃alkyl, —CF₃, and —OCF₃.

6. The compound of claim 1, or a pharmaceutically acceptable salt, stereoisomer, diastereomer or enantiomer thereof, wherein Z is —CH₂— and W is selected from the group consisting of —CH₂—, —CF₂—, —CH₂CH₂—, —O—, and —S—.

7. The compound of claim 1, or a pharmaceutically acceptable salt, stereoisomer, diastereomer or enantiomer thereof, wherein A is —CH— or —N—;
B is selected from the group consisting of —S—, —O—, —NH—, and —CH₂—; and
D is —C(=O)—.

8. The compound of claim 1, or a pharmaceutically acceptable salt, stereoisomer, diastereomer or enantiomer thereof, wherein R¹ and R² are connected by a divalent bridging group selected from —CH₂CH₂CH₂—, —CH₂CH₂CH₂CH₂—, —CH₂CH₂O—, —OCH₂CH₂—, —CH₂CH₂S—, —SCH₂CH₂—, —CH₂CH₂C(=O)—, and —C(=O)CH₂CH₂—, forming a 5- or 6-membered fused ring at the R¹ and R² positions, wherein said fused ring at the R¹ and R² positions is optionally substituted with 1-3 substituents independently selected from halogen, —OH, —CN, —NO₂, —C₁-C₃alkyl, —OC₁-C₃alkyl, —SC₁-C₃alkyl, —S(O)₂C₁-C₃alkyl, —CF₃, and —OCF₃.

9. The compound of claim 1 of Formula Ia, or a pharmaceutically acceptable salt, stereoisomer, diastereomer or enantiomer thereof, wherein

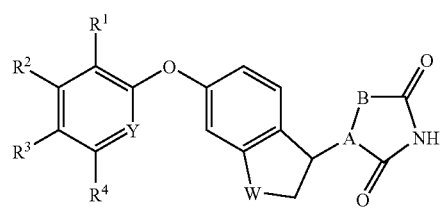

Ia

R¹, R², R³, and R⁴ are each independently selected from H, F, Br, Cl, CH₃, CF₃, —CH₂OH, —CH(OH)CH₃, —C(=O)H, —C(=O)OH, —C(=O)CH₃, —CH₂CH₃, —CH₂CF₃, cyclopropyl, —CN, —OCH₃, —OCF₃, —NO₂, CH(CH₃)₂, n-C₃H₇, n-C₅H₁₁, —C$_2$F$_5$, —CHFCH$_3$, —CHFCF$_3$, —CF$_2$CH$_3$, —CHF$_2$, —CH$_2$F, —OCHF$_2$, —OCH$_2$F, —OCH$_2$-phenyl, —C(=O)OCH$_3$, —S(O)$_2$CH$_3$, —C(=O)NH$_2$, —CH$_2$OC(=O)CH$_3$, —NH$_2$, —CH$_2$NH$_2$, —CH$_2$N(CH$_3$)$_2$, —CH$_2$NHC(=O)OC(CH$_3$)$_3$, —CH$_2$(1-pyrrolidinyl), and —C(=O)(3,3-difluoro-1-azetidinyl);

or alternatively R$^1$ and R$^2$ are connected by a 3- or 4-carbon chain selected from the group consisting of —CH=CH—CH=CH—, —CH$_2$CH$_2$CH$_2$—, —CH$_2$CH$_2$C(=O)—, and —C(=O)CH$_2$CH$_2$— to form a fused phenyl, cyclopentyl or cyclopentanone ring at the R$^1$ and R$^2$ positions, wherein said fused phenyl, cyclopentyl and cyclopentanone rings are optionally substituted with 1-3 substituents independently selected from halogen, —OH, —CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$;

Y is selected from =CH— and =N—;

W is selected from the group consisting of —CH$_2$—, —CF$_2$—, —CH$_2$CH$_2$—, —O—, and —S—

A is —CH— or —N—; and

B is selected from the group consisting of —S—, —O—, —NH—, and —CH$_2$—.

10. The compound of claim 9 of Formula Ia, or a pharmaceutically acceptable salt, stereoisomer, diastereomer or enantiomer thereof, wherein R$^1$ is selected from the group consisting of H, F, Br, Cl, CH$_3$, CF$_3$ and —CH$_2$CH$_3$; R$^2$ is selected from the group consisting of H, CH$_3$, CF$_3$, —CH$_2$CH$_3$, and —OCF$_3$;

or alternatively R$^1$ and R$^2$ are connected by the 4-carbon chain —CH=CH—CH=CH— to form a fused phenyl ring at the R$^1$ and R$^2$ positions;

R$^3$ is selected from the group consisting of H, Cl, CH$_3$, CF$_3$, —CN, and —NO$_2$;

R$^4$ is H or —CH$_3$;

Y is selected from =CH— and =N—;

W is selected from the group consisting of —CH$_2$—, —CH$_2$CH$_2$—, and —S—;

A is —CH— or —N—; and

B is selected from the group consisting of —S—, —O—, and —CH$_2$—.

11. The compound of claim 1 of Formula Ib, or a pharmaceutically acceptable salt, stereoisomer, diastereomer or enantiomer thereof,

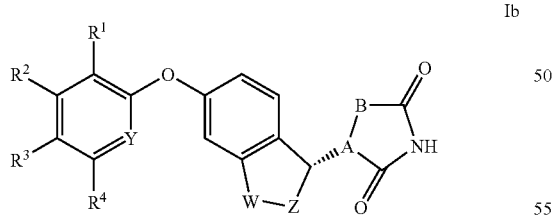

Ib wherein R$^1$, R$^2$, R$^3$, R$^4$, Y, W, Z, A, and B are as defined in claim 1.

12. The compound of claim 11 of Formula Ib, or a pharmaceutically acceptable salt, stereoisomer, diastereomer or enantiomer thereof, wherein R$^1$, R$^2$, R$^3$, and R$^4$ are each independently selected from H, F, Br, Cl, CH$_3$, CF$_3$, —CH$_2$OH, —CH(OH)CH$_3$, —C(=O)H, —C(=O)OH, —C(=O)CH$_3$, —CH$_2$CH$_3$, —CH$_2$CF$_3$, cyclopropyl, —CN, —OCH$_3$, —OCF$_3$, —NO$_2$, CH(CH$_3$)$_2$, n-C$_3$H$_7$, nC$_5$H$_{11}$, —C$_2$F$_5$, —CHFCH$_3$, —CHFCF$_3$, —CF$_2$CH$_3$, —CHF$_2$, —CH$_2$F, —OCHF$_2$, —OCH$_2$F, —OCH$_2$-phenyl, —C(=O)OCH$_3$, —S(O)$_2$CH$_3$, —C(=O)NH$_2$, —CH$_2$OC(=O)CH$_3$, —NH$_2$, —CH$_2$NH$_2$, —CH$_2$N(CH$_3$)$_2$, —CH$_2$NHC(=O)—OC(CH$_3$)$_3$, —CH$_2$(1-pyrrolidinyl), and —C(=O)(3,3-difluoro-1-azetidinyl);

or alternatively R$^1$ and R$^2$ are connected by a 3- or 4-carbon chain selected from the group consisting of —CH=CH—CH=CH—, —CH$_2$CH$_2$CH$_2$—, —CH$_2$CH$_2$C(=O)—, and —C(=O)CH$_2$CH$_2$— to form a fused phenyl, cyclopentyl or cyclopentanone ring at the R$^1$ and R$^2$ positions, wherein said fused phenyl, cyclopentyl and cyclopentanone rings are optionally substituted with 1-3 substituents independently selected from halogen, —OH, —CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$;

Y is selected from =CH— and =N—;

W is selected from the group consisting of —CH$_2$—, —CF$_2$—, —CH$_2$CH$_2$—, —O—, and —S—Z is —CH$_2$—;

A is —CH— or —N—; and

B is selected from the group consisting of —S—, —O—, —NH—, and —CH$_2$—.

13. The compound of claim 1 of Formula I, or a pharmaceutically acceptable salt, stereoisomer, diastereomer or enantiomer thereof, wherein R$^1$, R$^2$, R$^3$, and R$^4$ are each independently selected from H, F, Br, Cl, CH$_3$, CF$_3$, —CH$_2$OH, —CH(OH)CH$_3$, —C(=O)H, —C(=O)OH, —C(=O)CH$_3$, —CH$_2$CH$_3$, —CH$_2$CF$_3$, cyclopropyl, —CN, —OCH$_3$, —OCF$_3$, —NO$_2$, CH(CH$_3$)$_2$, n-C$_3$H$_7$, n-C$_5$H$_{11}$, —C$_2$F$_5$, —CHFCH$_3$, —CHFCF$_3$, —CF$_2$CH$_3$, —OCHF$_2$, —OCH$_2$F, —OCH$_2$-phenyl, —C(=O)OCH$_3$, —S(O)$_2$CH$_3$, —C(=O)NH$_2$, —CH$_2$OC(=O)CH$_3$, —NH$_2$, —CH$_2$NH$_2$, —CH$_2$N(CH$_3$)$_2$, —CH$_2$NHC(=O)OC(CH$_3$)$_3$, —CH$_2$(1-pyrrolidinyl), and —C(=O)(3,3-difluoro-1-azetidinyl);

or alternatively R$^1$ and R$^2$ are connected by a 3- or 4-carbon chain selected from the group consisting of —CH=CH—CH=CH—, —CH$_2$CH$_2$CH$_2$—, —CH$_2$CH$_2$C(=O)—, and —C(=O)CH$_2$CH$_2$— to form a fused phenyl, cyclopentyl or cyclopentanone ring at the R$^1$ and R$^2$ positions, wherein said fused phenyl, cyclopentyl and cyclopentanone rings are optionally substituted with 1-3 substituents independently selected from halogen, —OH, —CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$;

Y is selected from =CH— and =N—;

W is selected from the group consisting of —O—, —S—, and CH$_2$;

Z is selected from the group consisting of —CH$_2$— and —CH$_2$CH$_2$—;

A is —CH— or —N—;

B is selected from the group consisting of —S—, —O—, and —CH$_2$—; and

D is —C(=O).

14. The compound of claim 13 of Formula Ic, or a pharmaceutically acceptable salt thereof, wherein

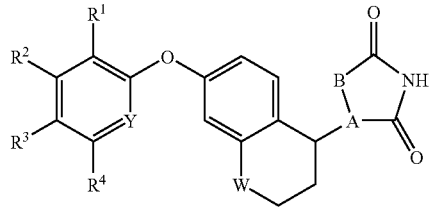

W is selected from the group consisting of —O— and —S—.

15. The compound of claim 14 of Formula Id, or a pharmaceutically acceptable salt, stereoisomer, diastereomer or enantiomer thereof, wherein

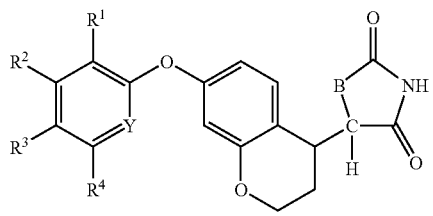

$R^1$, $R^2$, $R^3$, and $R^4$ are each independently selected from H, F, Br, Cl, $CH_3$, $CF_3$, —$CH_2OH$, —$CH(OH)CH_3$, —C(=O)H, —C(=O)OH, —C(=O)$CH_3$, —$CH_2CH_3$, —$CH_2CF_3$, cyclopropyl, —CN, —$OCH_3$, —$OCF_3$, —$NO_2$, $CH(CH_3)_2$, n-$C_3H_7$, n-$C_5H_{11}$, —$C_2F_5$, —$CHFCH_3$, —$CHFCF_3$, —$CF_2CH_3$, —$CHF_2$, —$CH_2F$, —$OCHF_2$, —$OCH_2F$, —$OCH_2$-phenyl, —C(=O)—$OCH_3$, —S(O)$_2CH_3$, —C(=O)$NH_2$, —$CH_2OC(=O)CH_3$, —$NH_2$, —$CH_2NH_2$, —$CH_2N(CH_3)_2$, —$CH_2NHC(=O)OC(CH_3)_3$, —$CH_2$(1-pyrrolidinyl), and —C(=O)(3,3-difluoro-1-azetidinyl);

or alternatively $R^1$ and $R^2$ are connected by a 3- or 4-carbon chain selected from the group consisting of —CH=CH—CH=CH—, —$CH_2CH_2CH_2$—, —$CH_2CH_2C(=O)$—, and —C(=O)$CH_2CH_2$— to form a fused phenyl, cyclopentyl or cyclopentanone ring at the $R^1$ and $R^2$ positions; and B is selected from the group consisting of —S— and —O—.

16. The compound of claim 13, which is selected from the group consisting of the compounds below, or a pharmaceutically acceptable salt, stereoisomer, diastereomer or enantiomer thereof:

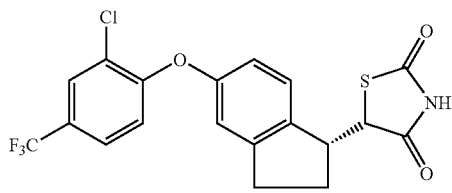

1

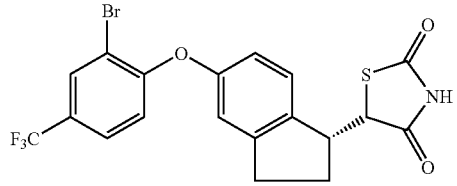

2

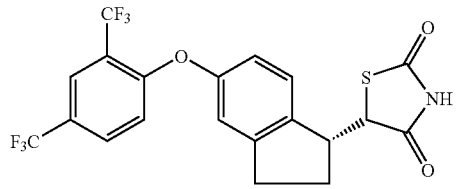

3

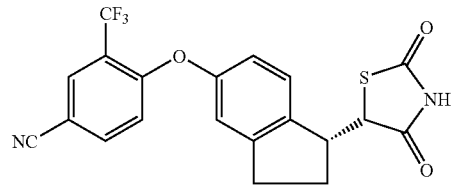

4

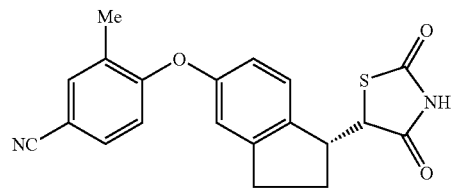

5

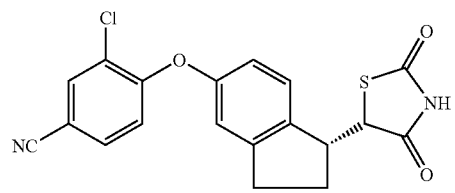

6

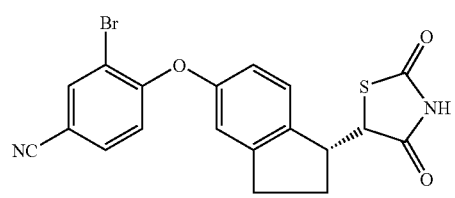

7

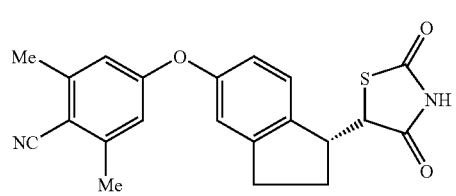

9

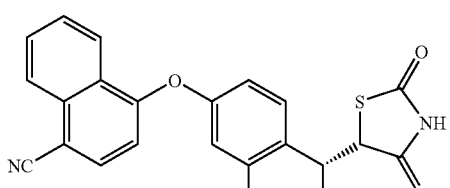

10

-continued
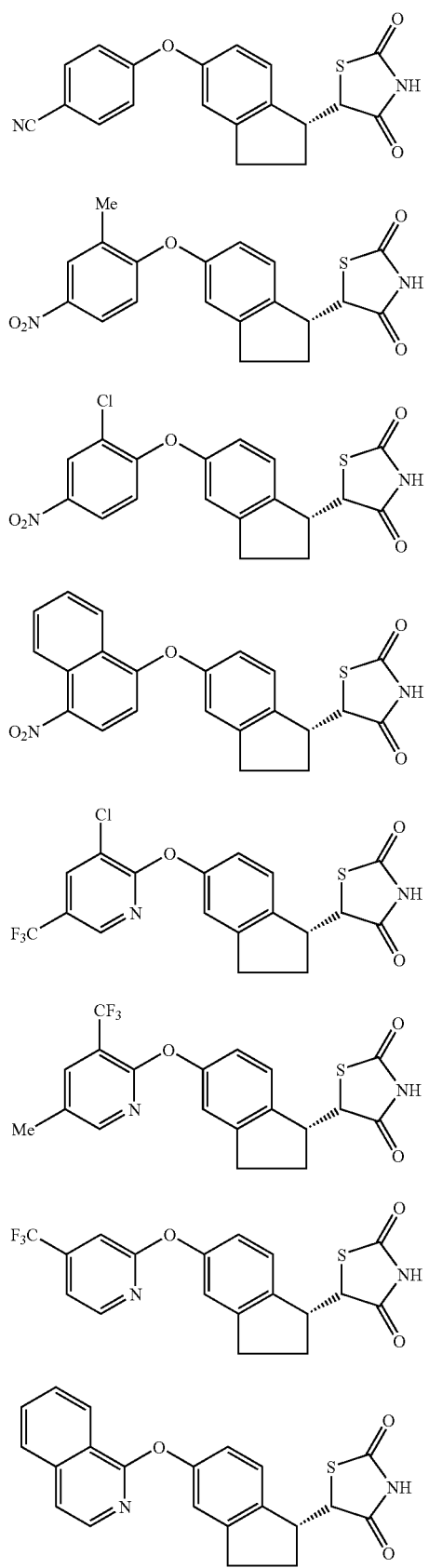
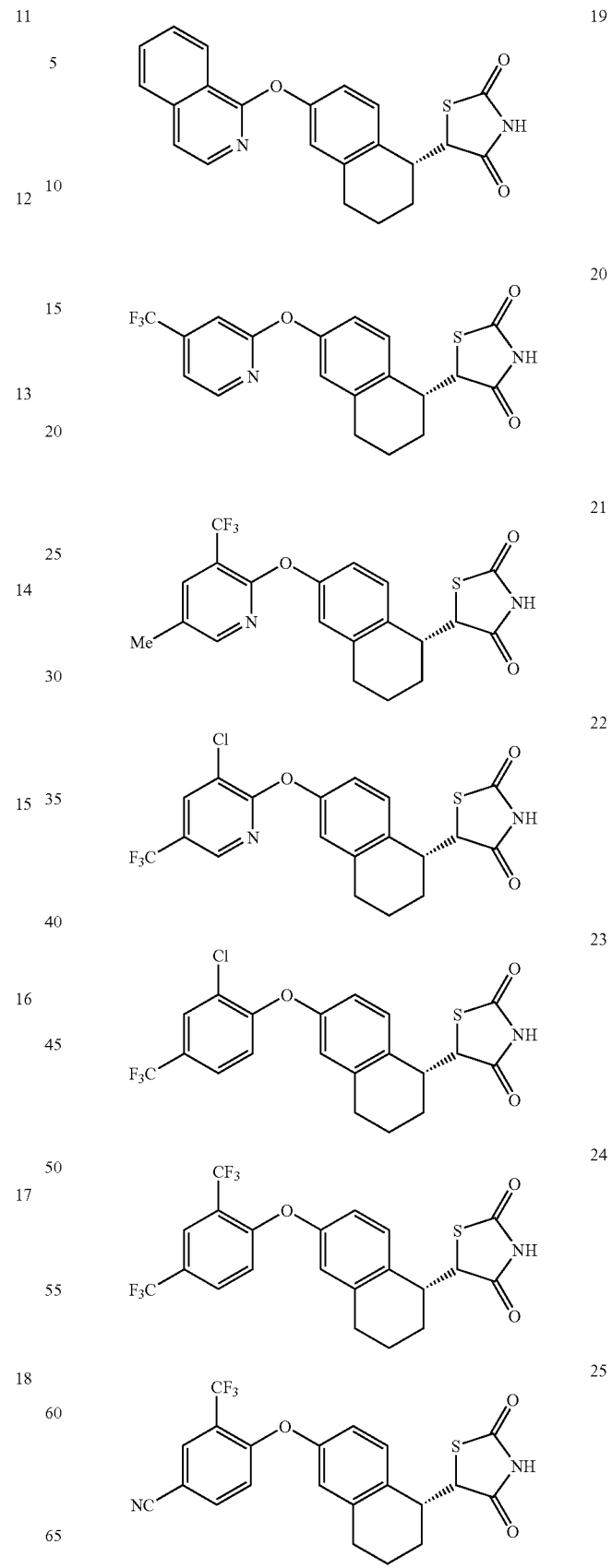

-continued
| | |
|---|---|
| 26 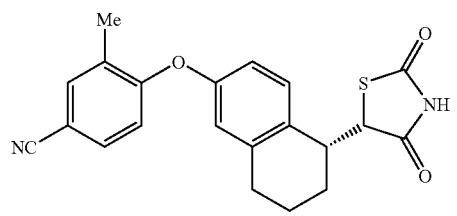 | 33 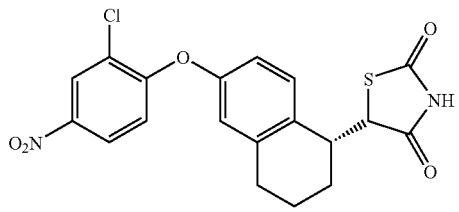 |
| 27 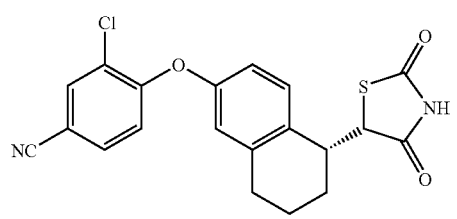 | 34 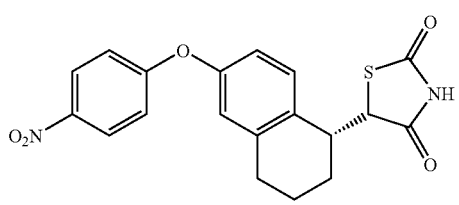 |
| 28 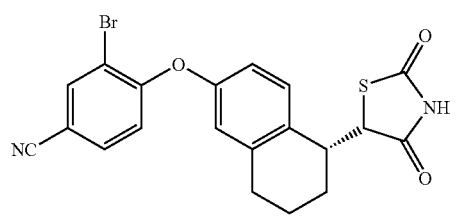 | 35 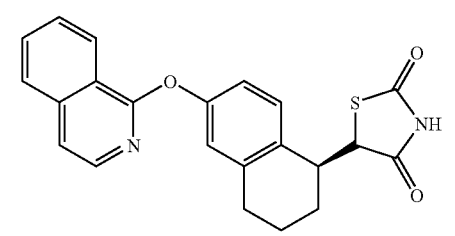 |
| 29 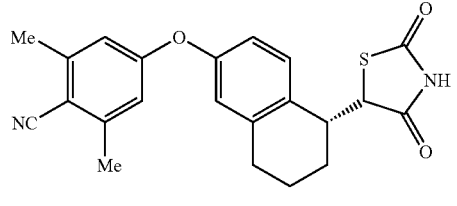 | 36 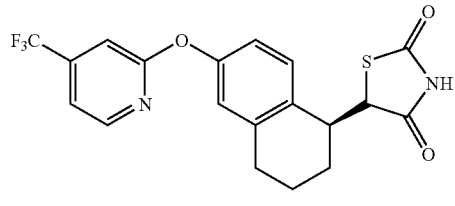 |
| 30 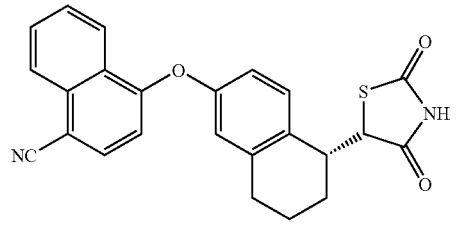 | 36 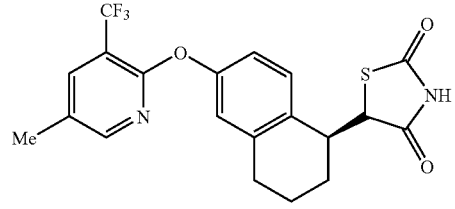 |
| 31 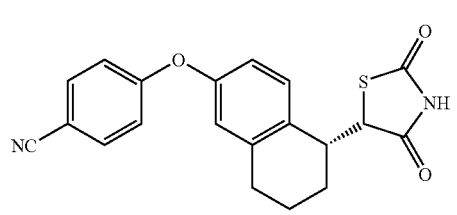 | 37 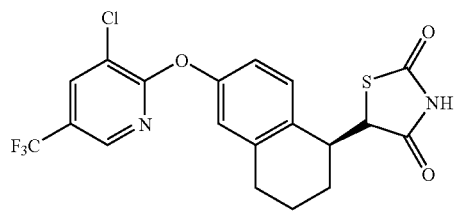 |
| 32 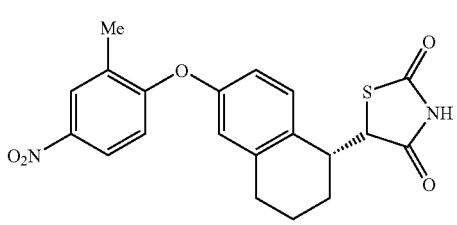 | 38 |

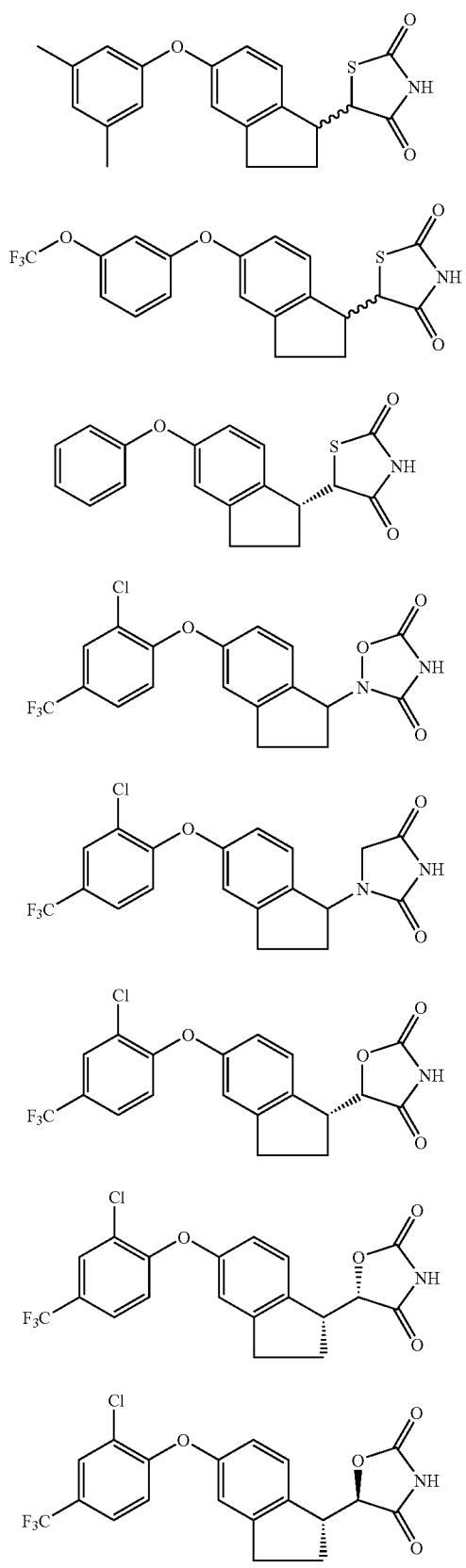
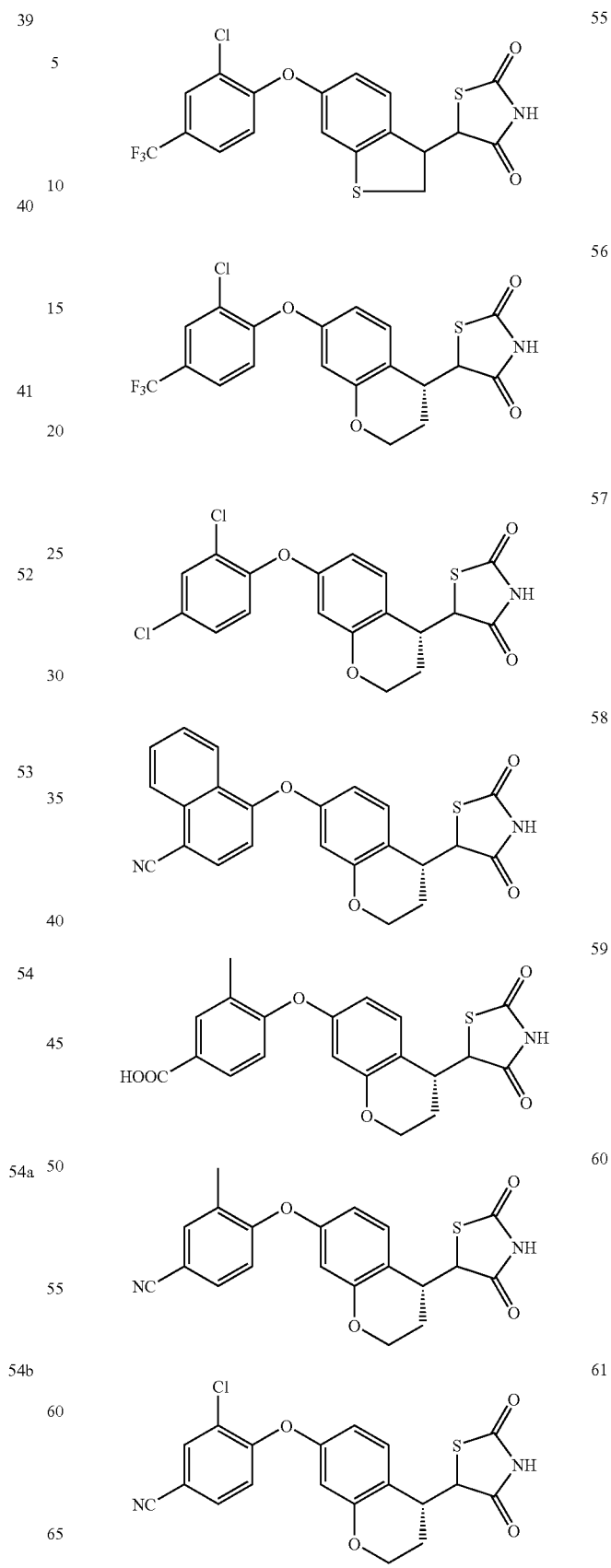

-continued

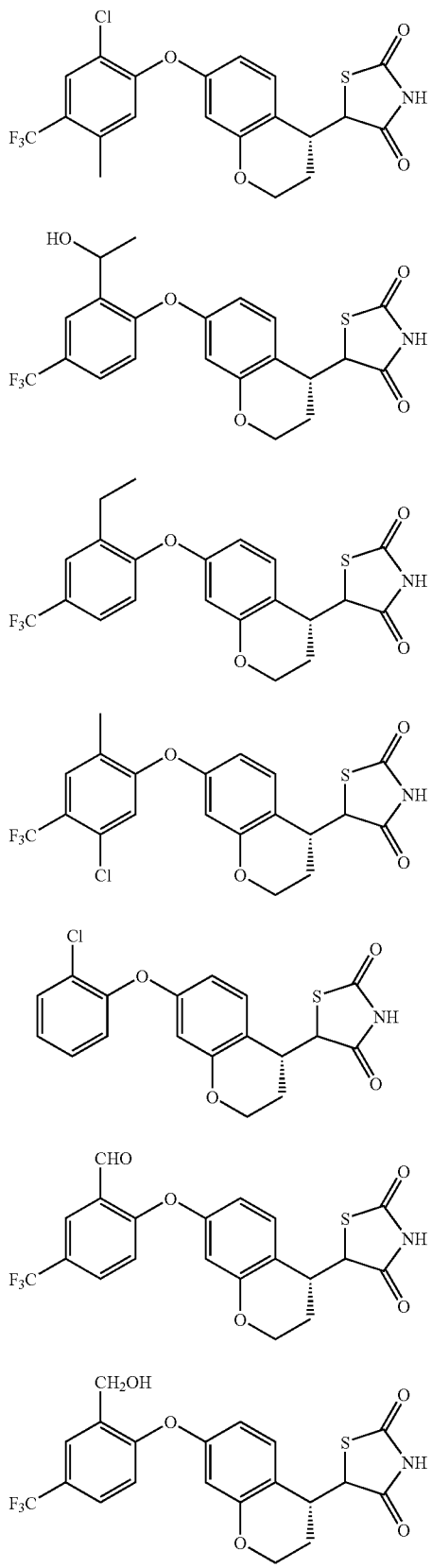

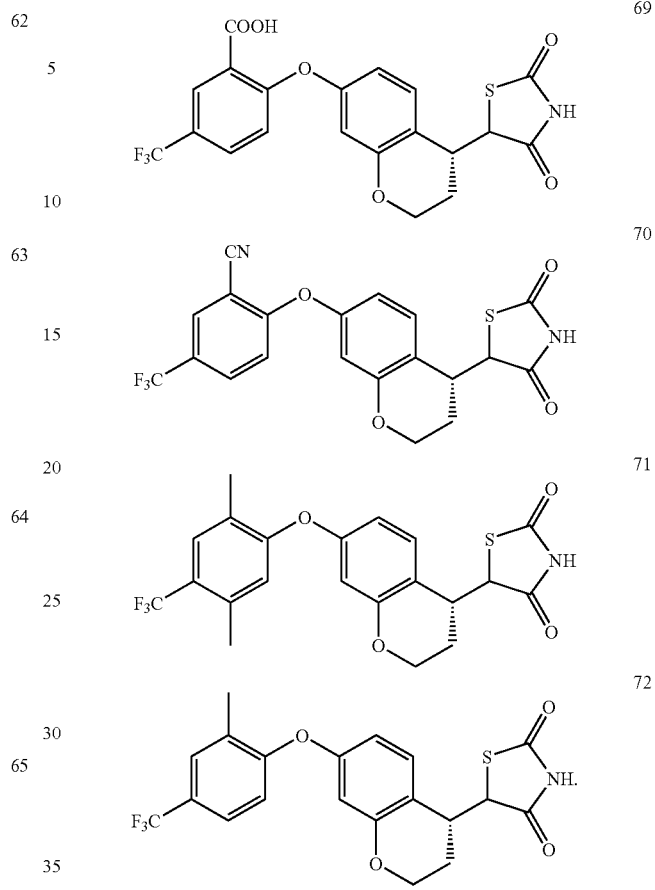

17. The compound of claim 13, which is selected from the group consisting of the compounds selected from (a) and (b) below, or a pharmaceutically acceptable salt, stereoisomer, diastereomer or enantiomer thereof, wherein (a) is a compound having the formula below which is selected from compounds numbered 42-48:

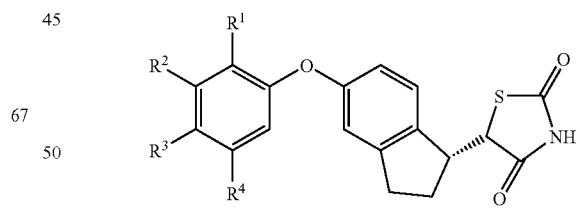

wherein the substituents $R^1$, $R^2$, $R^3$, and $R^4$ for the compounds 42-48 are:

|    | R1 | R2 | R3  | R4 |
|----|----|----|-----|----|
| 42 | H  | H  | H   | H  |
| 43 | H  | Et | H   | H  |
| 44 | Cl | H  | F   | H  |
| 45 | H  | Me | F   | H  |
| 46 | Me | H  | F   | H  |
| 47 | Et | H  | CN  | H  |
| 48 | Me | H  | CF3 | H  | and (b) is a compound having the formula below which is selected from compounds numbered 49-51:

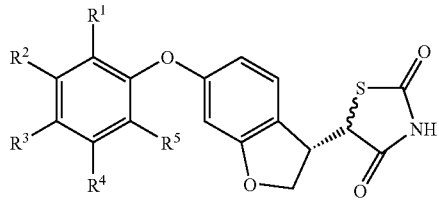

wherein the substituents $R^1$, $R^2$, $R^3$, $R^4$ and $R^5$ for the compounds 49-51 are:

|    | R1 | R2 | R3  | R4 | R5 |
|----|----|----|-----|----|----|
| 49 | Me | H  | CN  | H  | H  |
| 50 | Cl | H  | CF₃ | H  | H  |
| 51 | F  | H  | CN  | H  | H. |

18. The compound of claim 13, which is selected from the group consisting of the compounds listed below, or a pharmaceutically acceptable salt, stereoisomer, diastereomer or enantiomer thereof:

73

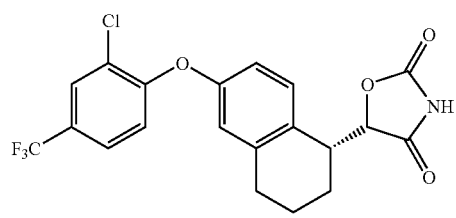

73a

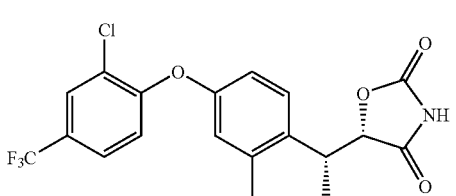

73b

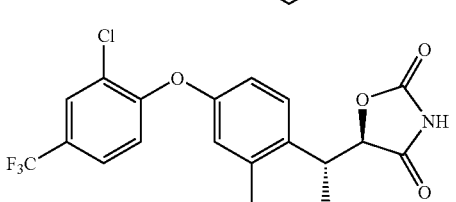

74

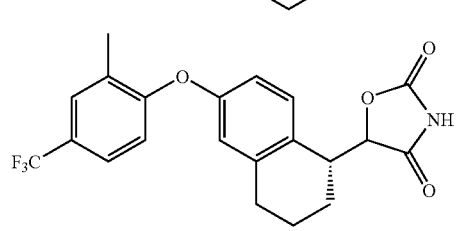

-continued

74a

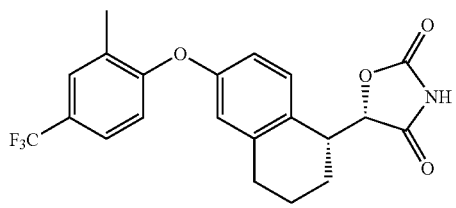

74b

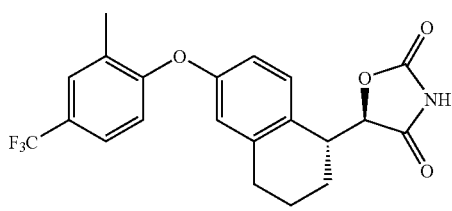

75

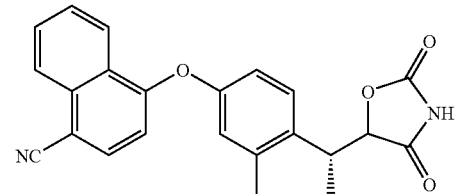

75a

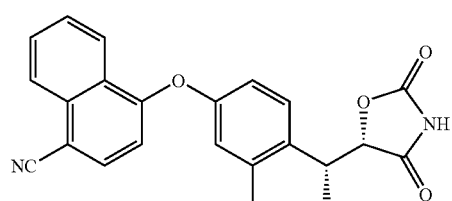

75b

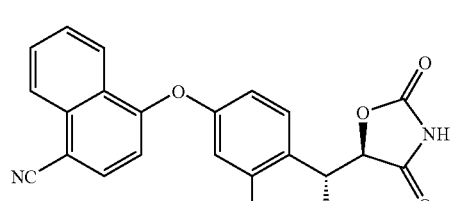

76

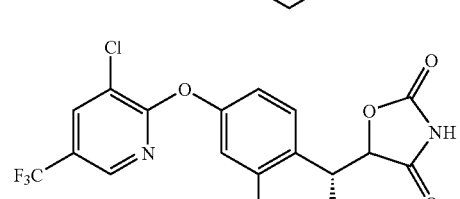

76a

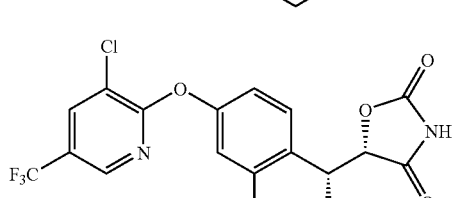

-continued
76b
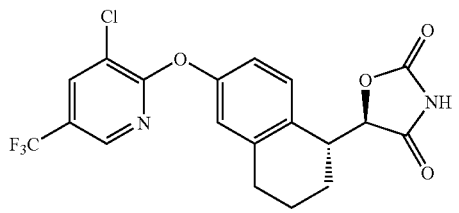
77
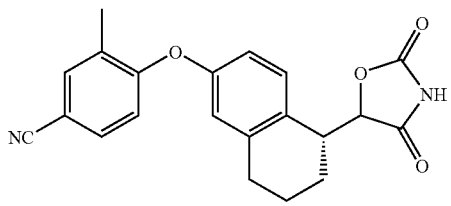
79
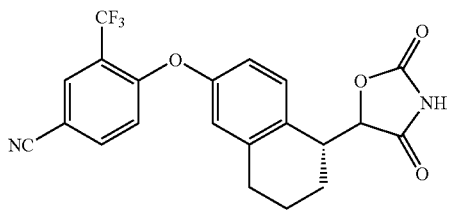
79a
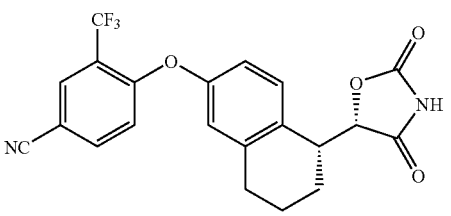
79b
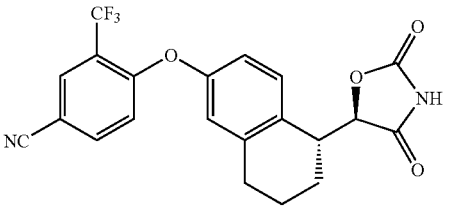
80
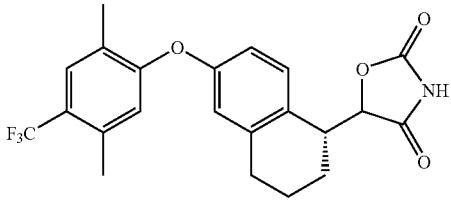
80a
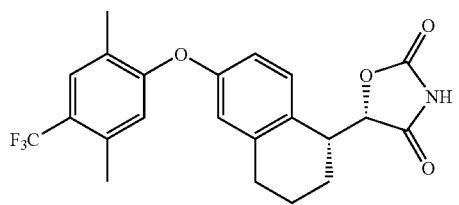
-continued
80b
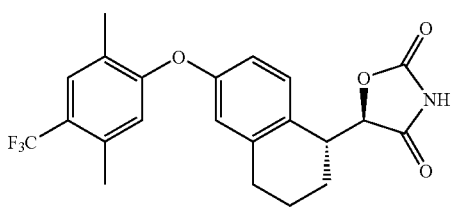
81
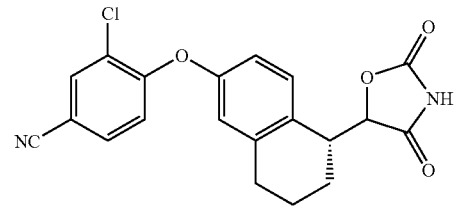
81a
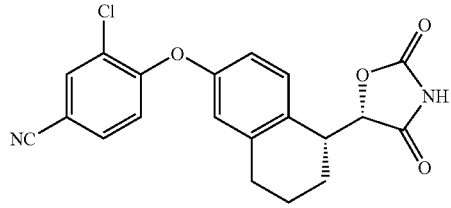
82b
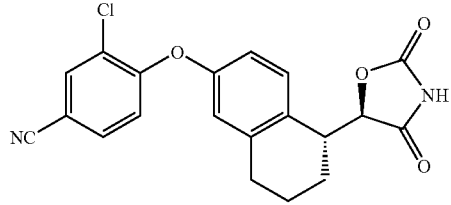
83
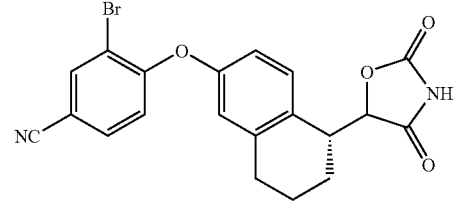
84
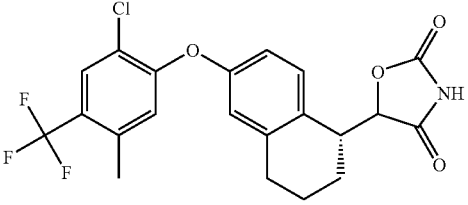
85
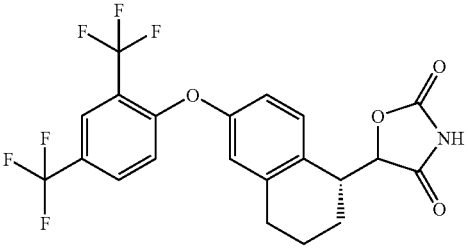

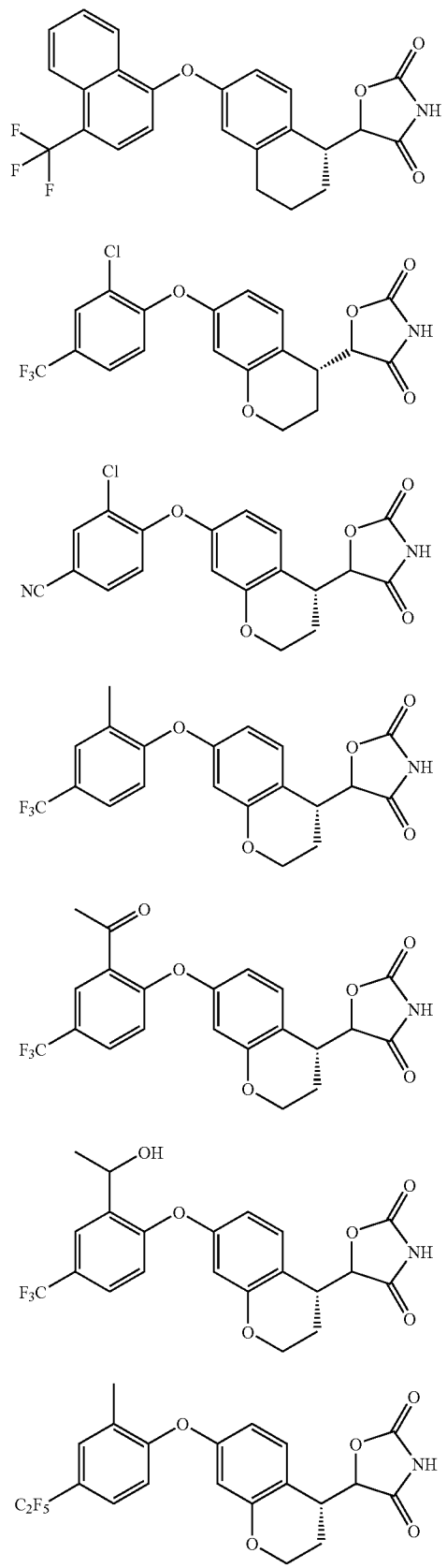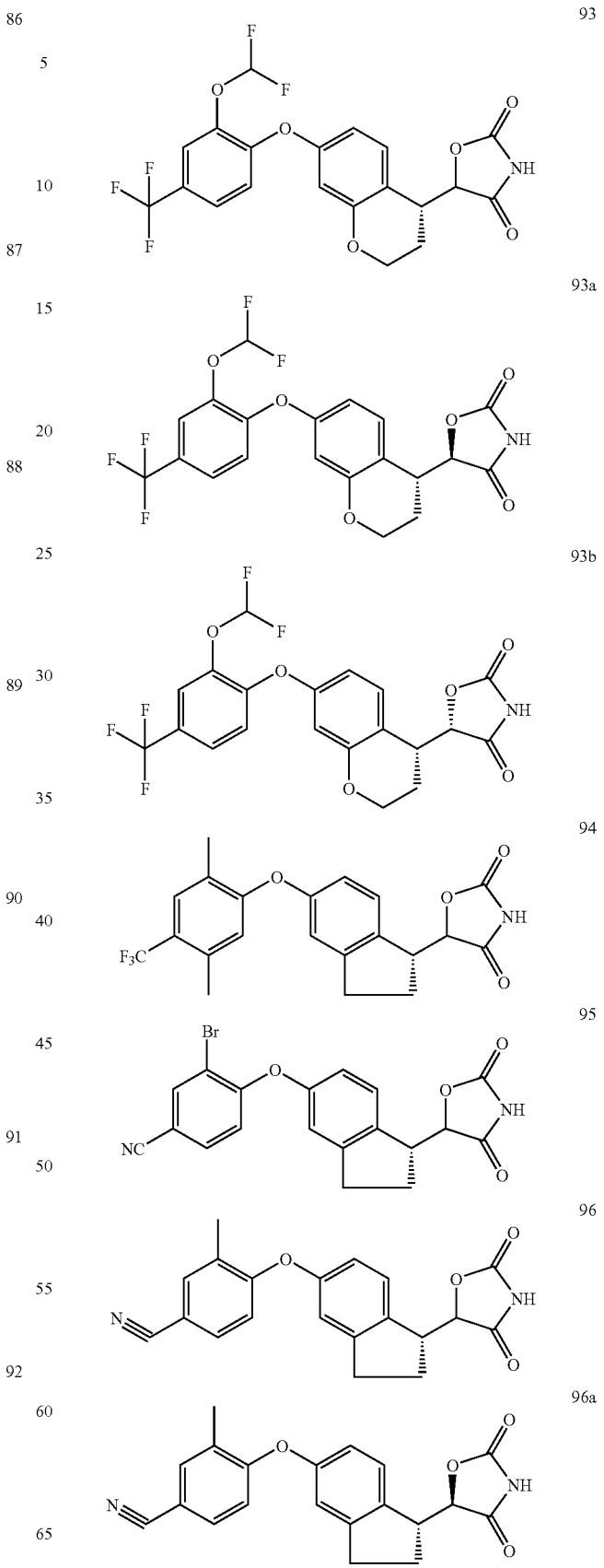

-continued

-continued
| | |
|---|---|
| 103 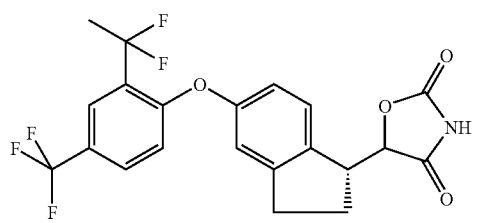 | 110 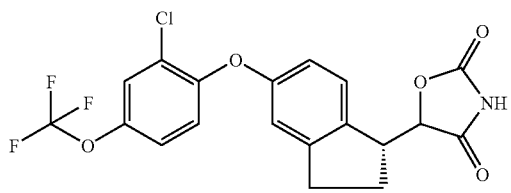 |
| 104 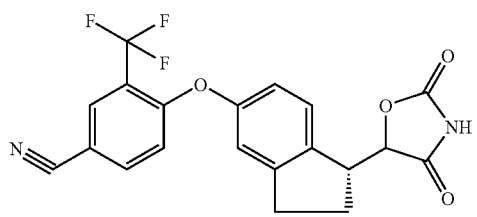 | 111 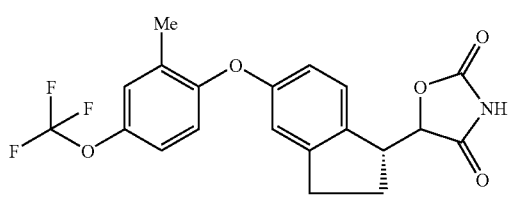 |
| 105 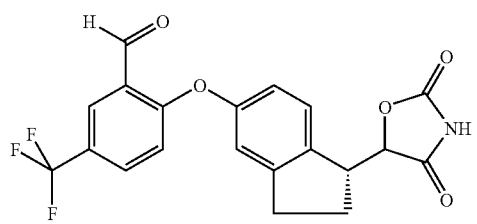 | 112 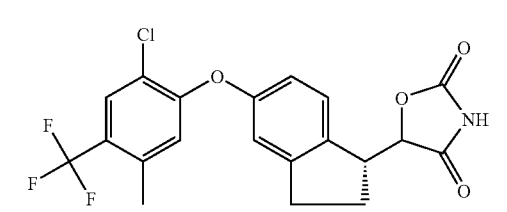 |
| 106 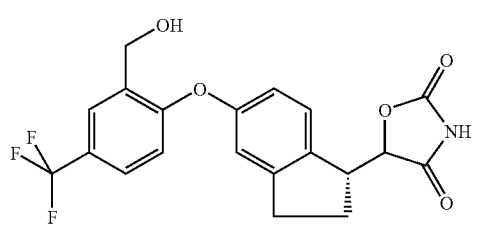 | 113 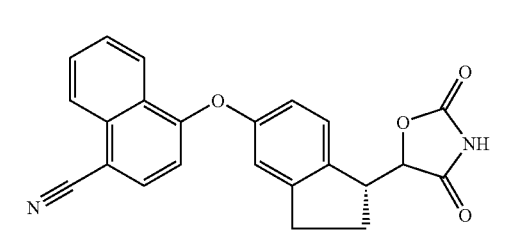 |
| 107 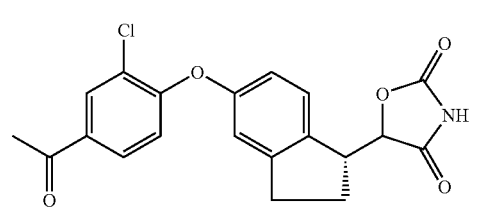 | 113a 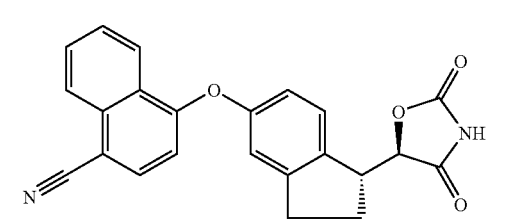 |
| 108 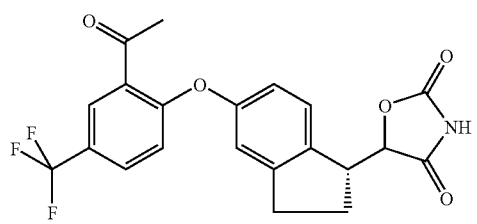 | 113b 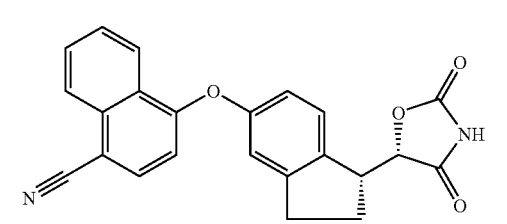 |
| 109 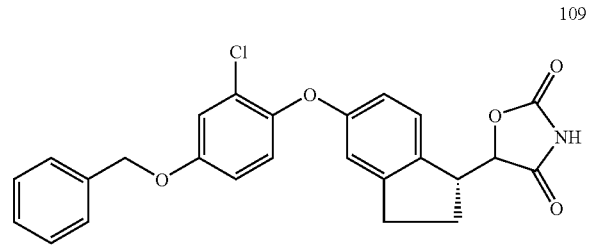 | 114 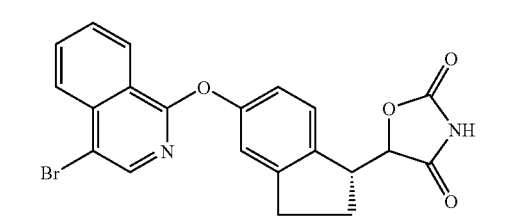 |

| | |
|---|---|
| 115 | 118 |
| 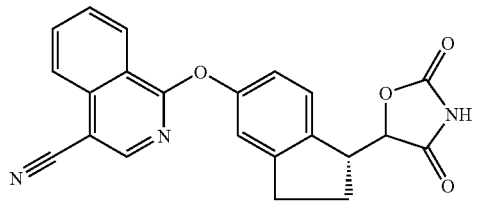 | 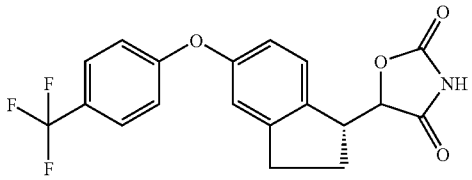 |
| 115a | 119 |
| 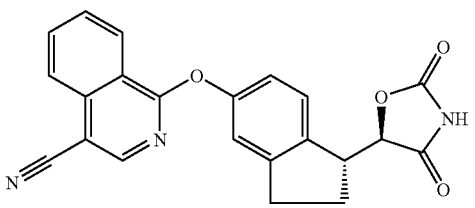 | 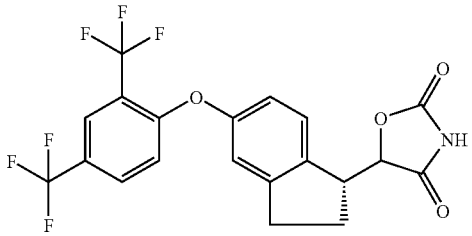 |
| 115b | 119a |
| 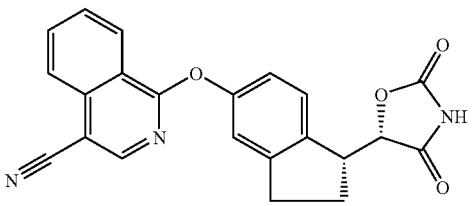 | 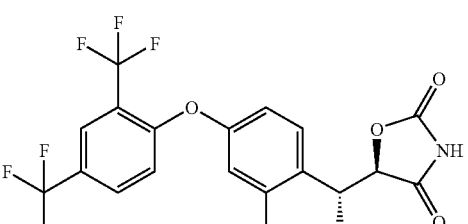 |
| 116 | 119b |
| 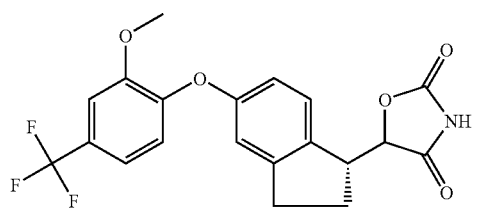 | 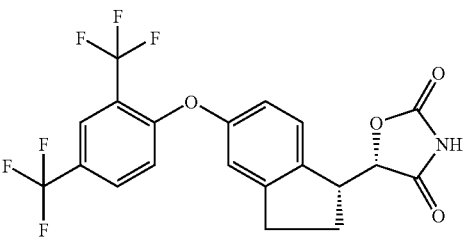 |
| 116a | 120 |
| 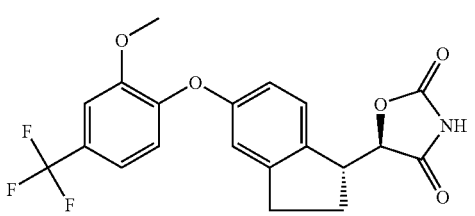 | 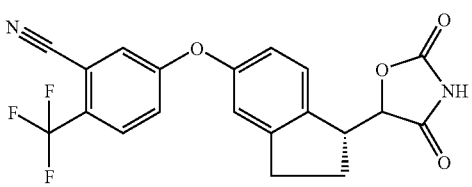 |
| 116b | 121 |
| 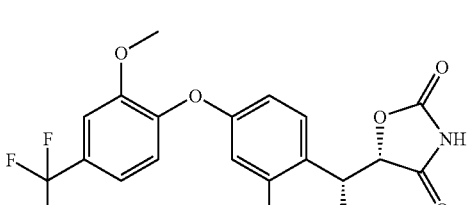 | 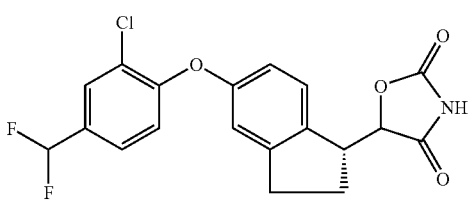 |
| 117 | 122 |
| 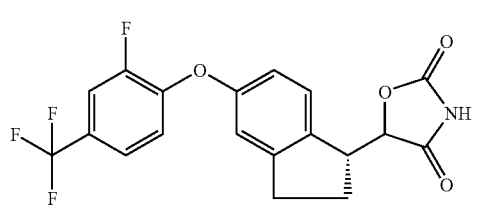 | 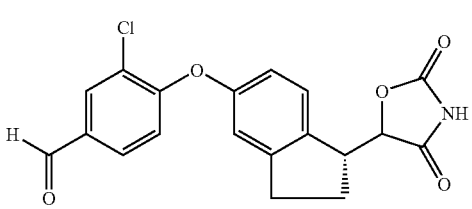 |

-continued
123
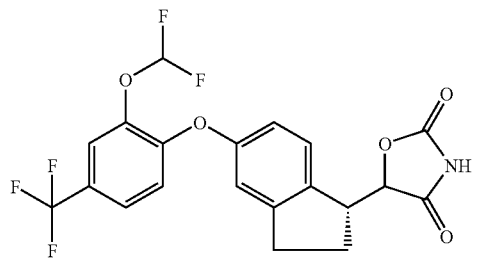
123a
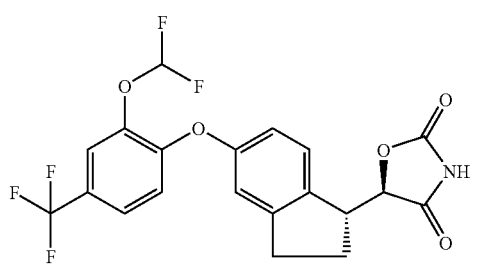
123b
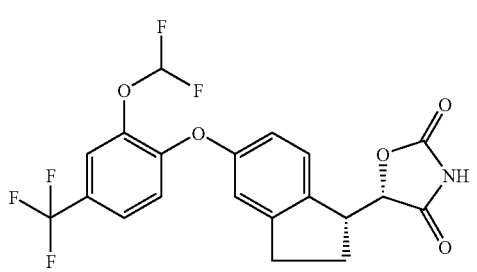
124
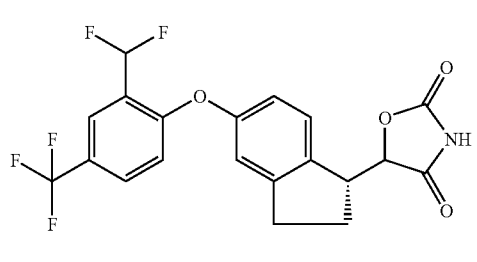
124a
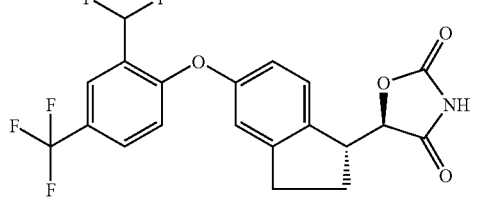
124b
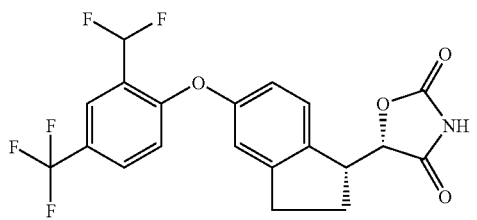
-continued
125
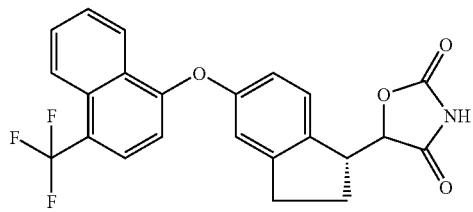
125a
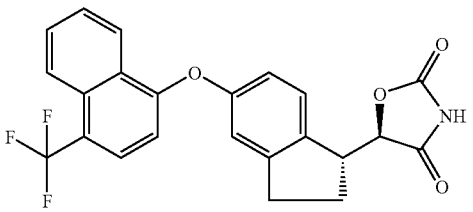
125b
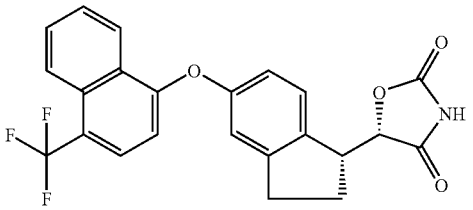
126
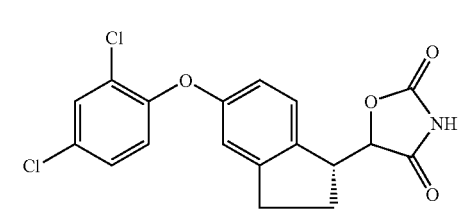
126a
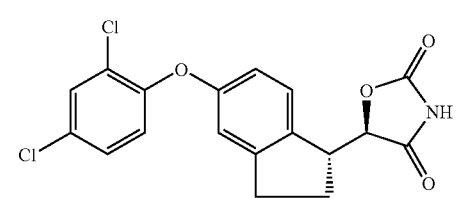
126b
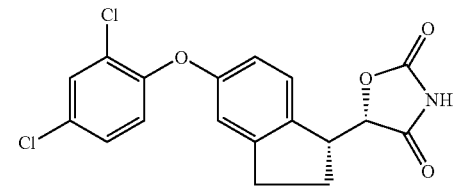
127
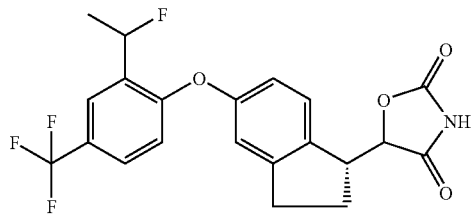

-continued
136
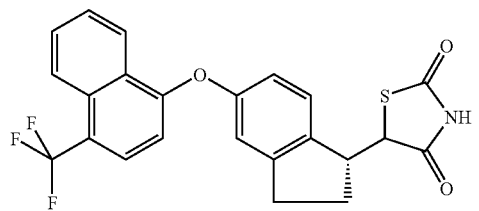
137
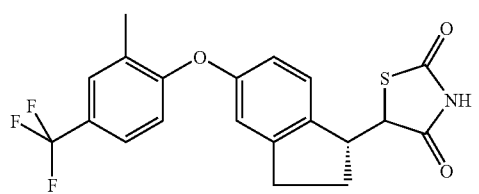
138
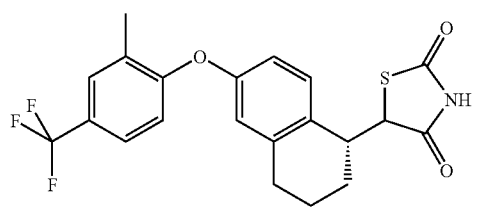
139
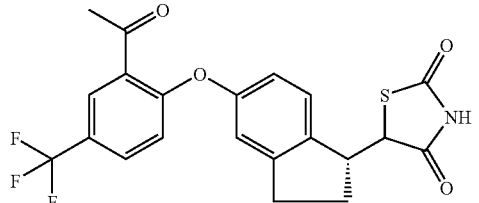
140
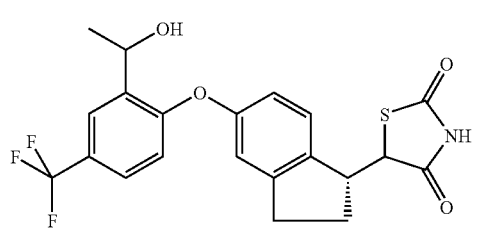
141
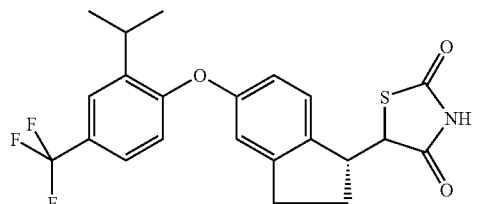
142
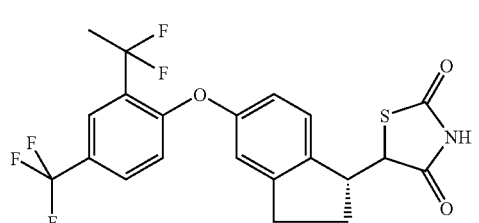
-continued
143
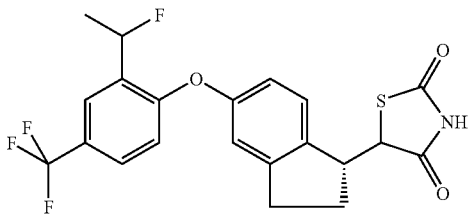
144
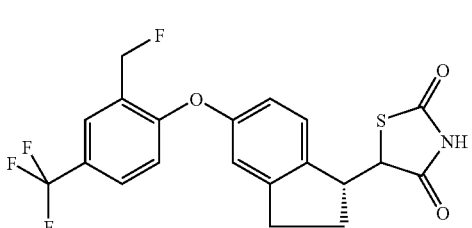
145
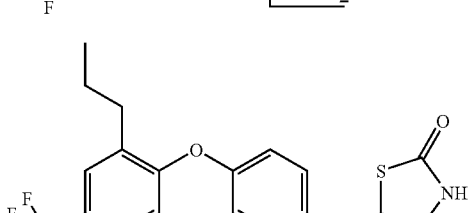
146
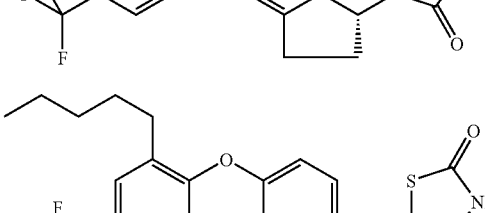
147
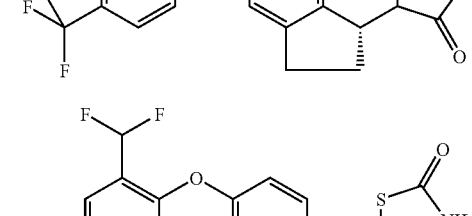
148
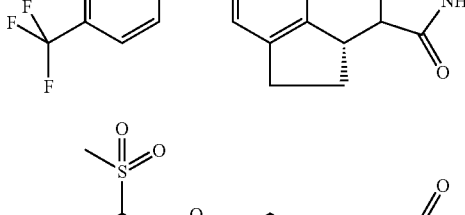
149
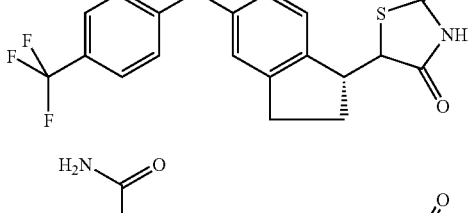

150 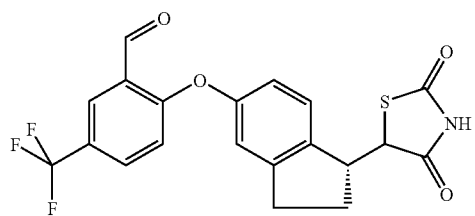
151 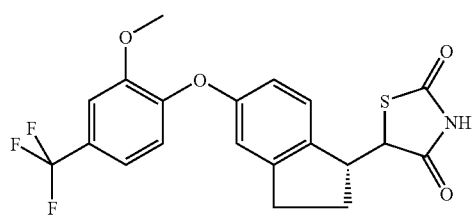
152 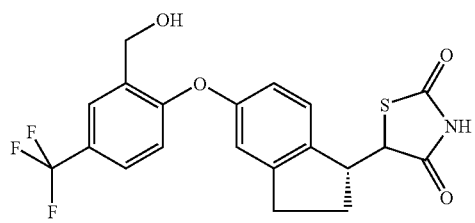
153 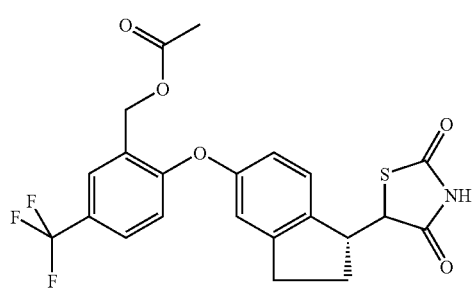
154 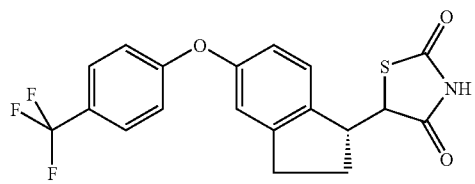
155 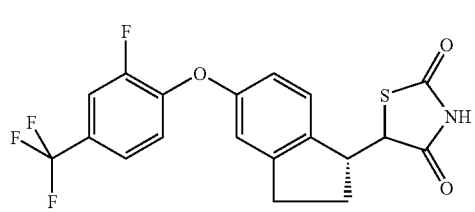
156 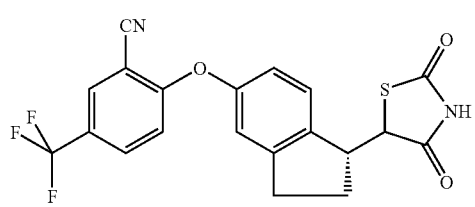
157 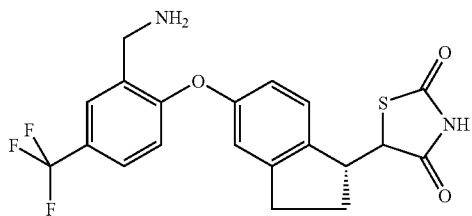
158 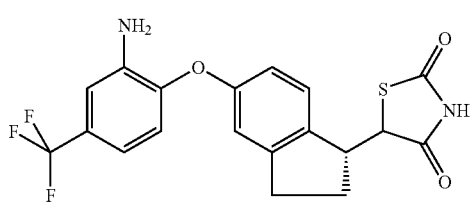
159 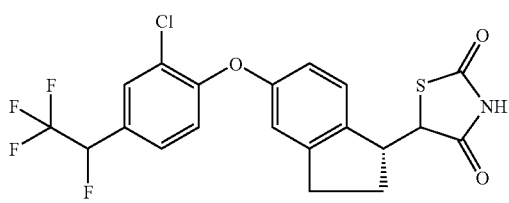
160 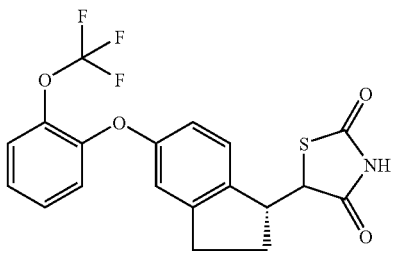
161 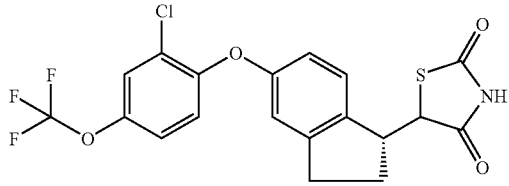
162 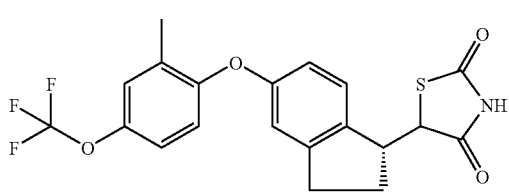
163 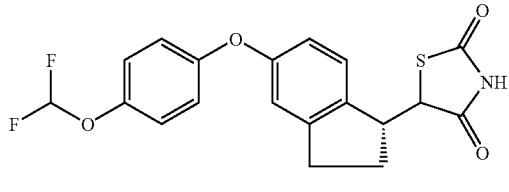

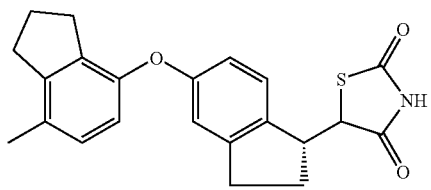
164
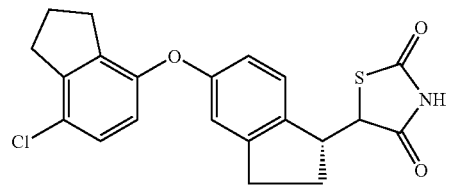
165
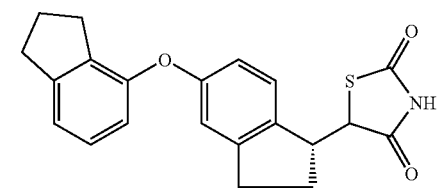
166
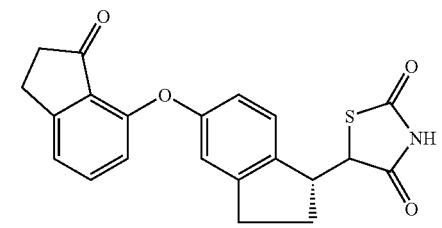
167
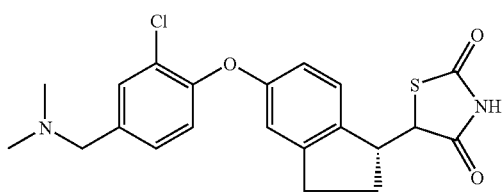
168
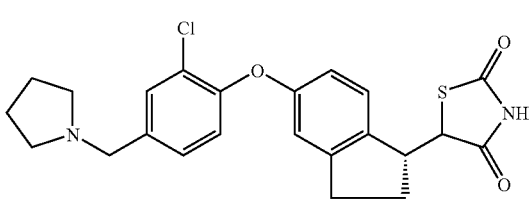
169
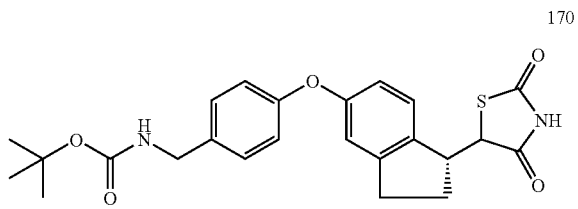
170
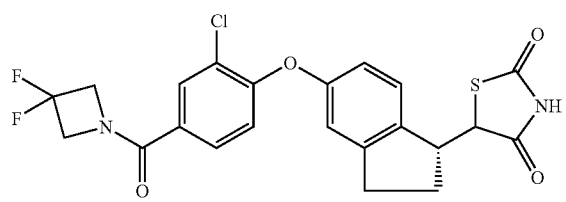
171
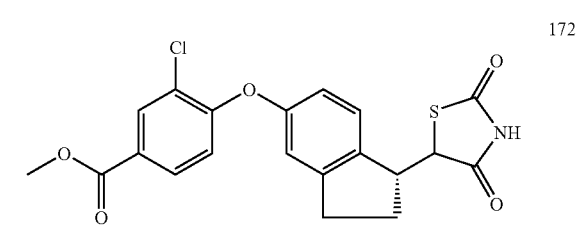
172
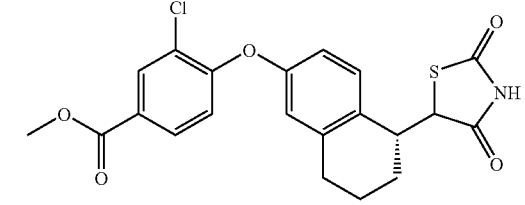
173
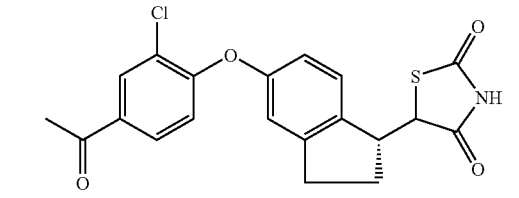
174
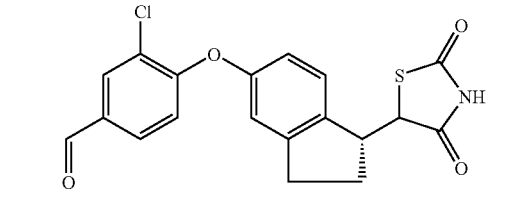
175
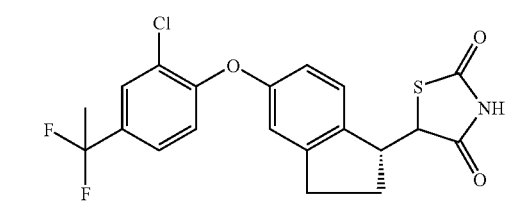
176
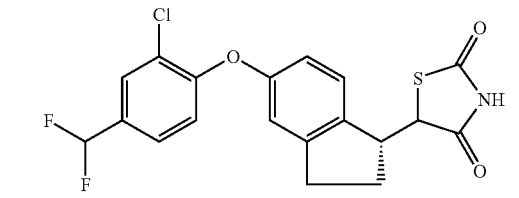
177

-continued

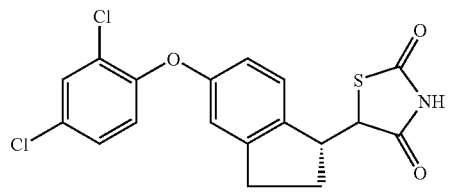

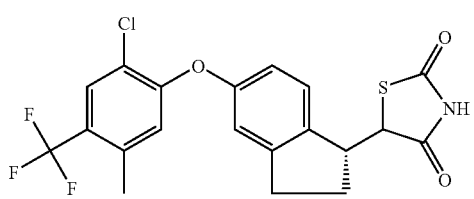

19. A pharmaceutical composition comprising a compound of claim 1, or a pharmaceutically acceptable salt, stereoisomer, diastereomer or enantiomer thereof, and a pharmaceutically acceptable carrier.

20. A method of treating type 2 diabetes mellitus in a patient in need of treatment comprising the administration to the patient of a therapeutically effective amount of a compound of claim 1, or a pharmaceutically acceptable salt, stereoisomer, diastereomer or enantiomer thereof.

* * * * *